(12) United States Patent
Heil et al.

(10) Patent No.: US 10,439,145 B2
(45) Date of Patent: Oct. 8, 2019

(54) COMPOUNDS FOR ELECTRONIC DEVICES

(71) Applicant: Merck Patent GmbH, Darmstadt (DE)

(72) Inventors: Holger Heil, Frankfurt am Main (DE);
Lara-Isabel Rodriguez, Darmstadt (DE); Fabrice Eckes, Darmstadt (DE); Oliver Kaufhold, Darmstadt (DE); Anja Gerhard, Egelsbach (DE); Stefan Riedmueller, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 442 days.

(21) Appl. No.: 14/425,373

(22) PCT Filed: Aug. 6, 2013

(86) PCT No.: PCT/EP2013/002343
§ 371 (c)(1),
(2) Date: Mar. 3, 2015

(87) PCT Pub. No.: WO2014/037077
PCT Pub. Date: Mar. 13, 2014

(65) Prior Publication Data
US 2015/0255720 A1 Sep. 10, 2015

(30) Foreign Application Priority Data
Sep. 4, 2012 (EP) ..................... 12006239

(51) Int. Cl.
*H01L 51/00* (2006.01)
*C07F 7/08* (2006.01)
*C07F 7/18* (2006.01)
*C07C 211/61* (2006.01)
*C07D 307/91* (2006.01)
*C09K 11/06* (2006.01)
*C09K 19/34* (2006.01)
(Continued)

(52) U.S. Cl.
CPC .......... *H01L 51/006* (2013.01); *C07B 59/001* (2013.01); *C07C 209/68* (2013.01); *C07C 211/61* (2013.01); *C07C 217/92* (2013.01); *C07C 229/52* (2013.01); *C07C 255/58* (2013.01); *C07D 209/88* (2013.01); *C07D 307/91* (2013.01); *C07D 471/04* (2013.01); *C07D 487/04* (2013.01); *C07D 493/04* (2013.01); *C07D 495/04* (2013.01); *C07D 519/00* (2013.01); *C07F 7/081* (2013.01); *C07F 7/083* (2013.01); *C07F 7/0807* (2013.01); *C07F 7/0816* (2013.01); *C07F 7/1804* (2013.01); *C07F 9/6568* (2013.01); *C07F 9/65683* (2013.01); *C09K 11/06* (2013.01); *C09K 19/3488* (2013.01); *C09K 19/404* (2013.01); *C09K 19/406* (2013.01); *H01L 51/0061* (2013.01); *H01L 51/0094* (2013.01); *H05B 33/10* (2013.01); *C07B 2200/05* (2013.01); *C07C 2603/18* (2017.05); *C07C 2603/24* (2017.05); *C07C 2603/42* (2017.05); *C07C 2603/48* (2017.05); *C07C 2603/50* (2017.05); *C07C 2603/52* (2017.05); *C07C 2603/54* (2017.05); *C07C 2603/94* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/1096* (2013.01); *H01L 51/0058* (2013.01); *H01L 51/0071* (2013.01); *H01L 51/0072* (2013.01); *H01L 51/0073* (2013.01);
(Continued)

(58) Field of Classification Search
CPC .. C07D 487/04; C07D 519/00; C07D 209/88; C07D 495/04; C07D 471/04; C07D 307/91; C07D 493/04; C07F 9/65683; C07F 7/0807; C07F 7/1852; C07F 7/0818; C07F 9/6568; C07F 7/083; C07F 7/0816; C07F 7/1804; C07F 7/081; C07B 59/001; C07B 2200/05; C07C 217/92; C07C 229/52; C07C 211/61; C07C 209/68; C07C 255/58; C07C 2603/94; C07C 2603/54; C07C 2603/52; C07C 2603/50; C07C 2603/48; C07C 2603/42; C07C 2603/24; C07C 2603/18; C09K 19/3488; C09K 19/404; C09K 19/406; C09K 11/06; C09K 2211/1088; C09K 2211/1096; C09K 2211/1092; C09K 2211/1029; C09K 2211/1014; C09K 2211/1011; C09K 2211/1007; H05B 33/10; H01L 51/0094; H01L 51/0061; H01L 51/006; H01L 51/0073; H01L 51/0074; H01L 51/5012; H01L 51/5072; H01L 51/0058; H01L 51/0071; H01L 51/0072
See application file for complete search history.

(56) References Cited

U.S. PATENT DOCUMENTS 8,766,001 B2 7/2014 Pflumm et al.
8,932,732 B2 1/2015 Buesing et al.
(Continued)

FOREIGN PATENT DOCUMENTS

JP 2009542735 A 12/2009
JP 2011529455 A 12/2011
(Continued)

OTHER PUBLICATIONS

Japanese Office Action for Japanese Application No. 2015-530308, dated Jun. 13, 2017, 7 pages.

*Primary Examiner* — Alexander C Kollias
(74) *Attorney, Agent, or Firm* — Kim IP Law Group PLLC

(57) ABSTRACT

The present invention relates to compounds which are suitable for use in electronic devices, preferably organic electroluminescent devices.

10 Claims, No Drawings

(51) Int. Cl.
  *C09K 19/40* (2006.01)
  *C07C 255/58* (2006.01)
  *C07F 9/6568* (2006.01)
  *C07B 59/00* (2006.01)
  *C07C 217/92* (2006.01)
  *C07C 229/52* (2006.01)
  *C07D 519/00* (2006.01)
  *C07D 209/88* (2006.01)
  *H05B 33/10* (2006.01)
  *C07C 209/68* (2006.01)
  *C07D 471/04* (2006.01)
  *C07D 487/04* (2006.01)
  *C07D 493/04* (2006.01)
  *C07D 495/04* (2006.01)
  *H01L 51/50* (2006.01)

(52) U.S. Cl.
  CPC ...... *H01L 51/0074* (2013.01); *H01L 51/5012* (2013.01); *H01L 51/5072* (2013.01)

(56) References Cited

U.S. PATENT DOCUMENTS

| | | | |
|---|---|---|---|
| 2008/0145708 A1* | 6/2008 | Heil | C07C 17/12 428/704 |
| 2009/0058289 A1* | 3/2009 | Stoessel | C07C 211/54 313/504 |
| 2009/0066225 A1* | 3/2009 | Kimura | C07C 211/58 313/504 |
| 2009/0261717 A1* | 10/2009 | Buesing | C07C 13/62 313/504 |
| 2011/0112275 A1* | 5/2011 | Parham | C09K 11/06 528/396 |
| 2011/0114889 A1 | 5/2011 | Buesing et al. | |
| 2011/0266533 A1* | 11/2011 | Buesing | C07D 219/02 257/40 |
| 2012/0012832 A1* | 1/2012 | Yabunouchi | C07C 211/61 257/40 |

FOREIGN PATENT DOCUMENTS

| | | |
|---|---|---|
| JP | 2012515732 A | 7/2012 |
| KR | 20090131536 A | 12/2009 |
| KR | 20110083442 A | 7/2011 |
| TW | 200815313 A | 4/2008 |
| TW | 200951101 A | 12/2009 |
| WO | 2006100896 A1 | 9/2006 |
| WO | WO-2008/006449 A1 | 1/2008 |
| WO | WO-2010/012328 A1 | 2/2010 |
| WO | 2010106806 A1 | 9/2010 |
| WO | 2011136484 A1 | 11/2011 |
| WO | WO-2011/136484 A1 | 11/2011 |

* cited by examiner

COMPOUNDS FOR ELECTRONIC DEVICES

RELATED APPLICATIONS

This application is a national stage application, filed pursuant to 35 U.S.C. § 371, of PCT/EP2013/002343, filed Aug. 6, 2013, which claims the benefit of European Patent Application No. 12006239.3, filed Sep. 4, 2012, which is incorporated herein by reference in its entirety.

The present invention relates to a compound, to the use of the compound in an electronic device, and to an electronic device comprising the compound.

It is currently of interest to develop compounds with which improved properties of electronic devices in one or more relevant points can be achieved, such as, for example, power efficiency, lifetime or colour coordinates of the emitted light.

In accordance with the present invention, the term electronic device is taken to mean in general electronic devices which comprise organic materials. In particular, these are taken to mean organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices known as OLEDs. The general structure and the functional principle of OLEDs are known to the person skilled in the art and are described, inter alia, in U.S. Pat. Nos. 4,539,507, 5,151,629, EP 0676461 and WO 1998/27136.

Further improvements are still necessary with respect to the performance data of OLEDs, in particular in view of broad commercial use, for example in displays or as light sources. Of particular importance in this connection are the lifetime, the efficiency and the operating voltage of the OLEDs and the colour values achieved. In particular in the case of blue-emitting OLEDs, there is potential for improvement with respect to the lifetime of the devices.

Of major importance in this connection is the choice of compound employed as dopant or as emitting compound in the OLED.

A multiplicity of compounds are known for this purpose from the prior art, in particular arylamines containing one or more condensed aryl groups.

Mention may be made here by way of example of the compounds disclosed in WO 2008/006449 and WO 2010/012328, which are based on an indenofluorene skeleton in which one of the phenyl groups is extended to form a larger aryl group, for example to form a naphthyl or pyrenyl group. The compounds additionally contain an amino group, which represents an optionally substituted diphenylamino group.

Although the compounds disclosed in the above-mentioned applications are valuable functional compounds, they are not yet ideally suited for use as deep-blue emitters in OLEDs. In particular, the constantly increasing demands mean that there is a continuous need for improvement with respect to central device parameters, such as power efficiency and lifetime.

The novel compound defined below achieves this technical object.

The present invention relates to a compound of the formula (I), (II) or (III)

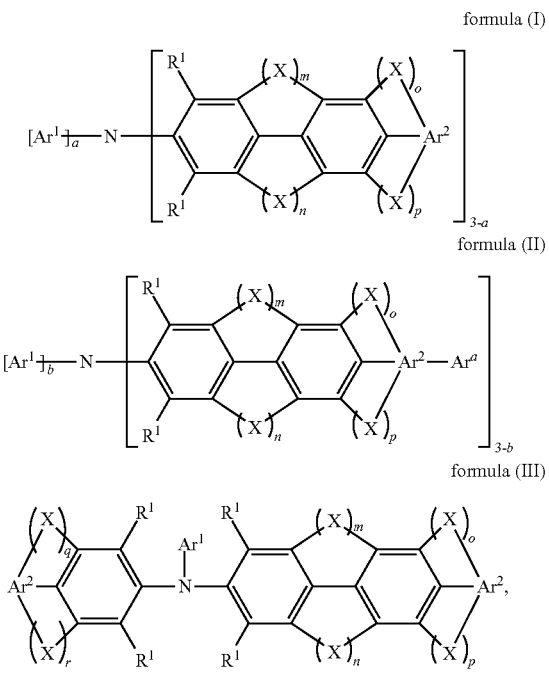

where:

Ar$^1$ is selected on each occurrence, identically or differently, from an aromatic or heteroaromatic ring system having 5 to 30 aromatic ring atoms, which may be substituted by one or more radicals R$^1$;

Ar$^2$ is on each occurrence, identically or differently, an aryl or heteroaryl group having 10 to 30 aromatic ring atoms, which may be substituted by one or more radicals R$^1$;

Ar$^a$ is on each occurrence, identically or differently, an aryl or heteroaryl group having 5 to 30 aromatic ring atoms, which may be substituted by one or more radicals R$^1$;

R$^1$ is on each occurrence, identically or differently, H, D, F, Cl, Br, I, C(=O)R$^2$, CN, Si(R$^2$)$_3$, N(R$^2$)$_2$, NO$_2$, P(=O)(R$^2$)$_2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^2$ and where one or more CH$_2$ groups in the above-mentioned groups may be replaced by —R$^2$C=CR$^2$—, —C≡C—, Si(R$^2$)$_2$, C=O, C=S, C=NR$^2$, —C(=O)O—, —C(=O)NR$^2$—, NR$^2$, P(=O)(R$^2$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^2$, or an aryloxy or heteroaryloxy group having 5 to 30 aromatic ring atoms, which may be substituted by one or more radicals R$^2$, where two or more radicals R$^1$ may be linked to one another and may form a ring;

R$^2$ is on each occurrence, identically or differently, H, D, F, Cl, Br, I, C(=O)R$^3$, CN, Si(R$^3$)$_3$, N(R$^3$)$_2$, NO$_2$, P(=O)(R$^3$)$_2$, S(=O)R$^3$, S(=O)$_2$R$^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by —$R^3C$=$CR^3$—, —C≡C—, $Si(R^3)_2$, C=O, C=S, C=$NR^3$, —C(=O) O—, —C(=O)$NR^3$—, $NR^3$, P(=O)($R^3$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form a ring;

$R^3$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^3$ here may be linked to one another and form a ring;

X is on each occurrence, identically or differently, $BR^1$, $C(R^1)_2$, $C(R^1)_2$—$C(R^1)_2$, $Si(R^1)_2$, $Si(R^1)_2$—$Si(R^1)_2$, C=O, C=$NR^1$, C=$C(R^1)_2$, C(=O)N($R^1$), O, S, S=O, $SO_2$, $NR^1$, $PR^1$ or P(=O)$R^1$;

a is equal to 0 or 1;

b is equal to 0, 1 or 2;

m, n, o, p, q and r are on each occurrence, identically or differently, 0 or 1; where, in the case where they are 0, a group $R^1$ is bonded instead at the relevant positions to which the corresponding group X is bonded;

where the sum of m and n is equal to 1 or 2, and the sum of o and p is equal to 1 or 2, and the sum of q and r is equal to 1 or 2.

The compound is highly suitable for use in OLEDs. In particular, it is suitable for use as deep-blue-emitting emitter compound. In particular, it results, on use in OLEDs, in an improvement with respect to the lifetime of the devices and/or the power efficiency.

General definitions of terms which apply for the purposes of the present application are given below.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is intended, for the purposes of the present application, to be taken to mean, inter alia, that the two radicals are linked to one another by a chemical bond. This is illustrated by the following scheme:

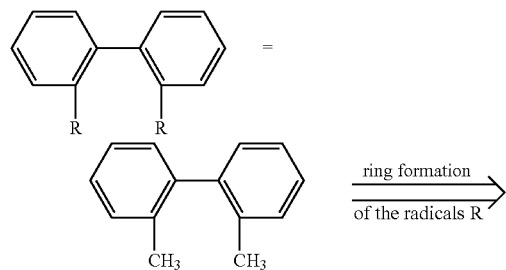

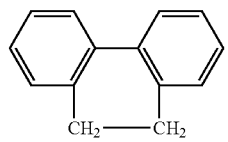

Furthermore, however, the above-mentioned formulation is also intended to be taken to mean that, in the case where one of the two radicals represents hydrogen, the second radical is bonded to the position to which the hydrogen atom was bonded, with formation of a ring. This is intended to be illustrated by the following scheme:

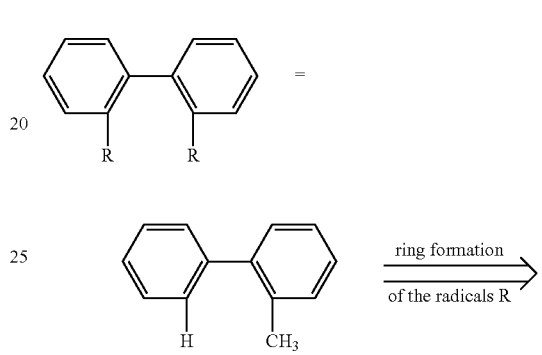

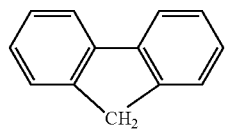

Ar$^1$ is preferably selected on each occurrence, identically or differently, from an aromatic or heteroaromatic ring system having 5 to 24 aromatic ring atoms, which may be substituted by one or more radicals R$^1$. Ar$^1$ is particularly preferably an aromatic or heteroaromatic ring system having 6 to 18 aromatic ring atoms, which may be substituted by one or more radicals R$^1$.

Ar$^1$ is furthermore preferably an aryl or heteroaryl group having 6 to 16 aromatic ring atoms which is substituted by one or more radicals R$^1$.

Ar$^1$ is very particularly preferably selected on each occurrence, identically or differently, from phenyl, naphthyl, anthracenyl, phenanthrenyl, pyrenyl, triphenylenyl, chrysenyl, biphenyl, terphenyl, fluorenyl, spirobifluorenyl, carbazolyl, dibenzofuranyl, dibenzothiophenyl or silafluorenyl, each of which may be substituted by one or more radicals R$^1$.

Ar$^1$ is furthermore preferably selected identically on each occurrence in a formula.

Ar$^2$ is preferably selected on each occurrence, identically or differently, from an aryl group having 10 to 22 aromatic ring atoms, which may be substituted by one or more radicals R$^1$, particularly preferably from an aryl group having 10 to 18 aromatic ring atoms, which may be substituted by one or more radicals R$^1$.

Ar$^2$ is very particularly preferably selected from the following groups of the formulae (Ar$^2$-a) to (Ar$^2$-h):

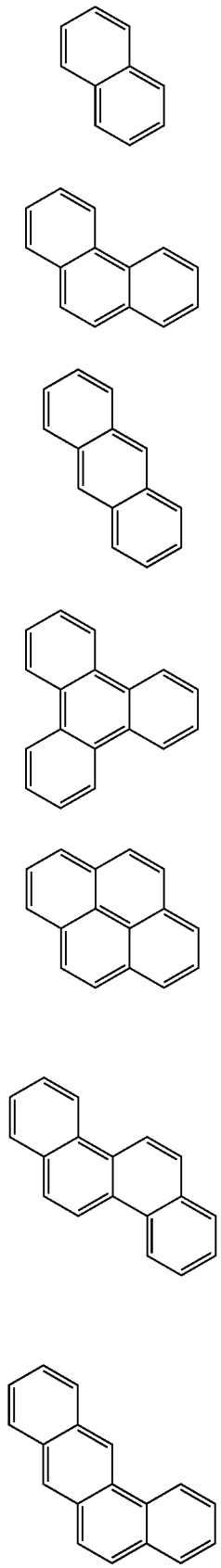

formula (Ar²-a)

formula (Ar²-b)

formula (Ar²-c)

formula (Ar²-d)

formula (Ar²-e)

formula (Ar²-f)

formula (Ar²-g)

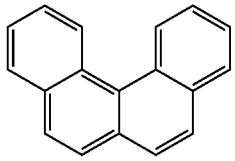

formula (Ar²-h)

where the bonding positions to the radical of the formula may be at any desired positions and where the groups may be substituted by one or more radicals $R^1$. The bridge X with $Ar^2$ and the phenyl group preferably forms a five- or six-membered ring, particularly preferably a five-membered ring.

$Ar^2$ is furthermore preferably selected identically on each occurrence.

For the compounds of the formula (III), it is preferred for the group $Ar^2$ to be substituted by one or more groups $R^1$ selected from an aromatic or heteroaromatic ring system having 5 to 30 aromatic ring atoms, which may be substituted by one or more radicals $R^2$. The group $Ar^2$ on the left in formula (III) is particularly preferably substituted by one or more groups $R^1$ selected from an aromatic or heteroaromatic ring system having 5 to 30 aromatic ring atoms, which may be substituted by one or more radicals $R^2$. The substituents $R^1$ of the group $Ar^2$, in particular of the left-hand group $Ar^2$ in formula (III), are particularly preferably aryl or heteroaryl groups having 6 to 16 aromatic ring atoms, which may be substituted by one or more radicals $R^2$.

The group $Ar^a$ is preferably on each occurrence, identically or differently, an aryl or heteroaryl group having 5 to 18 aromatic ring atoms, particularly preferably 5 to 14 aromatic ring atoms, very particularly preferably 5 to 10 aromatic ring atoms, where $Ar^a$ may be substituted by one or more radicals $R^1$.

It is furthermore preferred for $Ar^a$ to represent an aryl group having 6 to 18 aromatic ring atoms, particularly preferably 6 to 14 aromatic ring atoms and very particularly preferably 6 to 10 aromatic ring atoms, where $Ar^a$ may be substituted by one or more radicals $R^1$.

$Ar^a$ is furthermore preferably selected identically on each occurrence.

The group X is preferably on each occurrence, identically or differently, $C(R^1)_2$, $C(R^1)_2$—$C(R^1)_2$, $Si(R^1)_2$, $Si(R^1)_2$—$Si(R^1)_2$, O, S, $NR^1$ or $PR^1$. X is particularly preferably on each occurrence, identically or differently, $C(R^1)_2$ or $Si(R^1)_2$, very particularly preferably $C(R^1)_2$.

$R^1$ is preferably on each occurrence, identically or differently, H, D, F, CN, $Si(R^2)_3$, $N(R^2)_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^2$ and where one or more $CH_2$ groups in the above-mentioned groups may be replaced by —C≡C—, —$R^2$C=C$R^2$—, $Si(R^2)_2$, C=O, C=$NR^2$, —$NR^2$—, —O—, —S—, —C(=O)O— or —C(=O)$NR^2$—, or an aromatic or heteroaromatic ring system having 5 to 20 aromatic ring atoms, which may in each case be substituted by one or more radicals $R^2$, where two or more radicals $R^1$ may be linked to one another and may form a ring.

$R^1$ is particularly preferably selected on each occurrence, identically or differently, from H, D, F, CN, $Si(R^2)_3$, a straight-chain alkyl group having 1 to 8 C atoms or a branched or cyclic alkyl group having 3 to 8 C atoms, where the alkyl groups may each be substituted by one or more

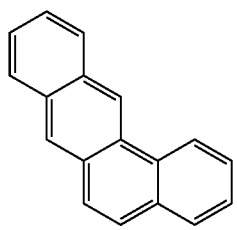

radicals $R^2$ and where one or more $CH_2$ groups in the alkyl groups may be replaced by —C≡C—, —$R^2$C=C$R^2$—, Si($R^2$)$_2$, C=O or —O—, or an aryl or heteroaryl group having 6 to 16 aromatic ring atoms, which may in each case be substituted by one or more radicals $R^2$.

$R^1$ which is bonded to groups X, in particular groups X which represent C($R^1$)$_2$, is preferably selected on each occurrence, identically or differently, from alkyl groups having 1 to 10 C atoms, which may be substituted by one or more radicals $R^2$, and aromatic or heteroaromatic ring systems having 6 to 12 aromatic ring atoms, which may be substituted by one or more radicals $R^2$. Two radicals $R^1$ which are bonded to the same group X, in particular in the case of groups X which represent C($R^1$)$_2$, may form a ring with one another.

$R^2$ is preferably on each occurrence, identically or differently, H, D, F, CN, Si($R^3$)$_3$, N($R^3$)$_2$, a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by —C≡C—, —$R^3$C=C$R^3$—, Si($R^3$)$_2$, C=O, C=N$R^3$, —N$R^3$—, —O—, —S—, —C(=O)O— or —C(=O)N$R^3$—, or an aromatic or heteroaromatic ring system having 5 to 20 aromatic ring atoms, which may in each case be substituted by one or more radicals $R^3$, where two or more radicals $R^2$ may be linked to one another and may form a ring.

$R^2$ is particularly preferably selected on each occurrence, identically or differently, from H, D, F, CN, a straight-chain alkyl group having 1 to 8 C atoms or a branched or cyclic alkyl group having 3 to 8 C atoms, where the alkyl groups may each be substituted by one or more radicals $R^2$ and where one or more $CH_2$ groups in the alkyl groups may be replaced by —C≡C—, —$R^3$C=C$R^3$—, Si($R^3$)$_2$, C=O or —O—, or an aryl or heteroaryl group having 6 to 16 aromatic ring atoms, which may in each case be substituted by one or more radicals $R^3$.

It is furthermore preferred for a to be equal to 1.

It is furthermore preferred for b to be equal to 2.

It is furthermore preferred for the sum of m and n to be equal to 1.

It is furthermore preferred for the sum of o and p to be equal to 1.

It is furthermore preferred for the sum of q and r to be equal to 1.

It is furthermore preferred for m and p to be equal to 1 and for n and o to be equal to 0.

It is furthermore preferred for n and o to be equal to 1 and for m and p to be equal to 0.

Preferred embodiments of formula (I) conform to the following formulae (I-1) to (I-12):

formula (I-1)

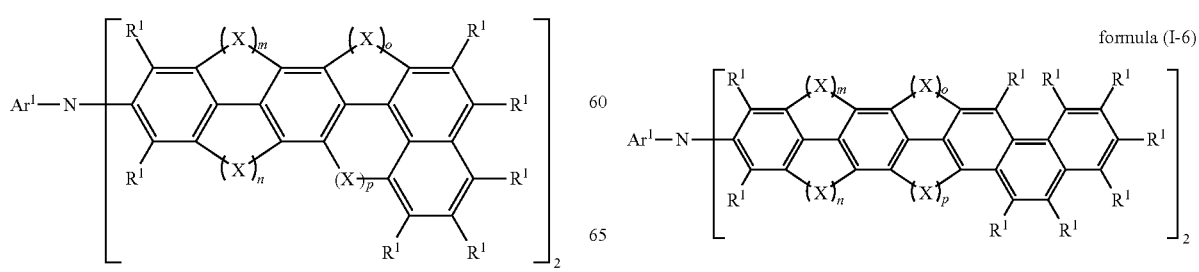

formula (I-2)

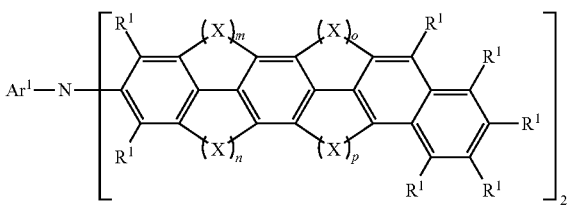

formula (I-3)

formula (I-4)

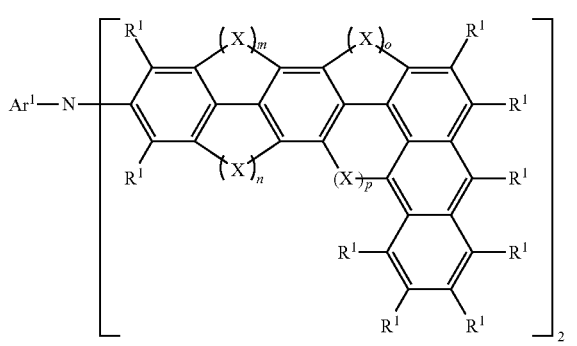

formula (I-5)

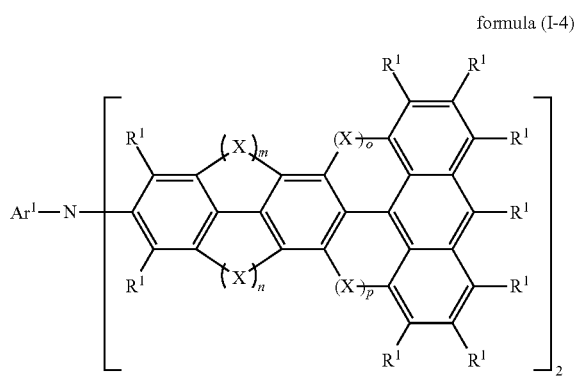

formula (I-6)

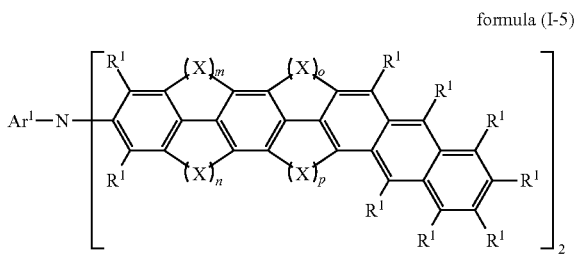

-continued

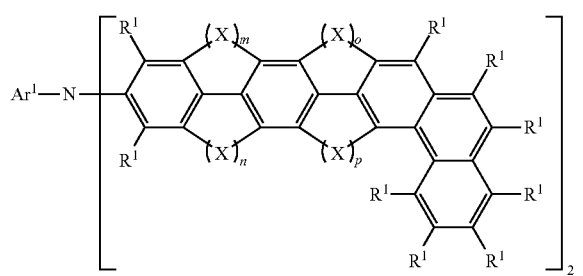
formula (I-7)

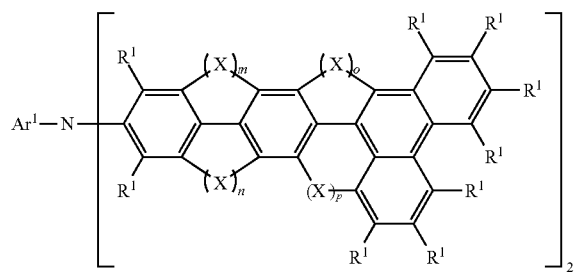
formula (I-8)

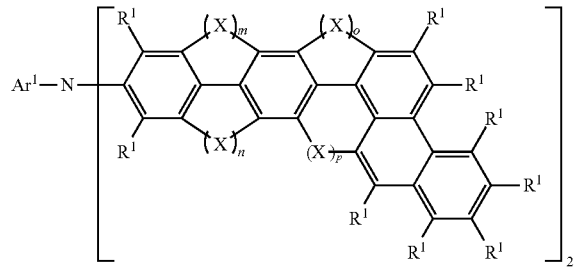
formula (I-9)

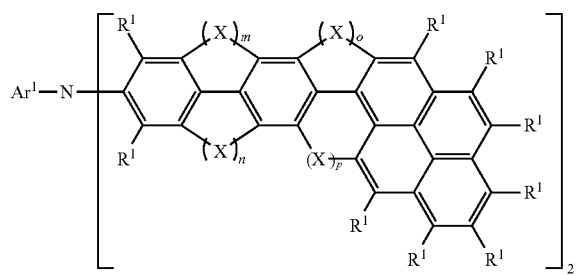
formula (I-10)

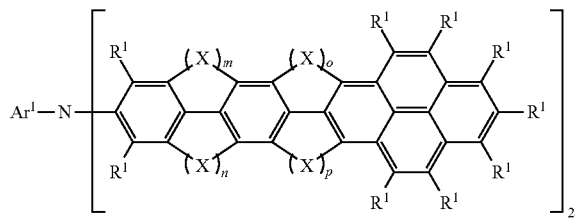
formula (I-11)

-continued

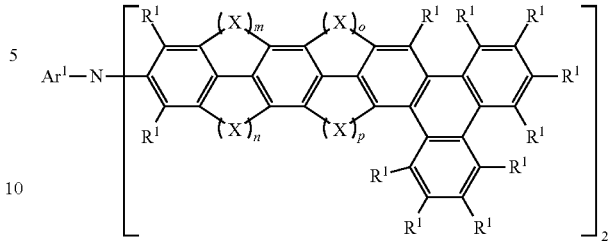
formula (I-12)

where the symbols and indices occurring are as defined above. The preferred embodiments indicated above for the symbols and indices preferably apply.

It is preferred in the above formulae for m and p to be equal to 1 and for n and o to be equal to 0. Alternatively, it is preferred in the above formulae for n and o to be equal to 1 and for m and p to be equal to 0.

Preferred embodiments of formula (II) conform to the following formulae (II-1) to (II-12):

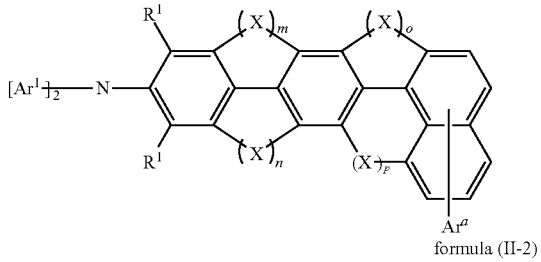
formula (II-1)

formula (II-2)

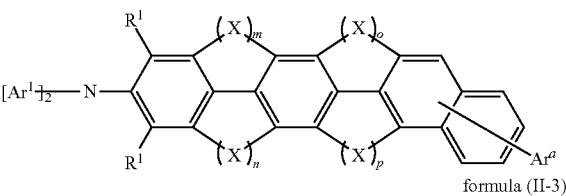
formula (II-3)

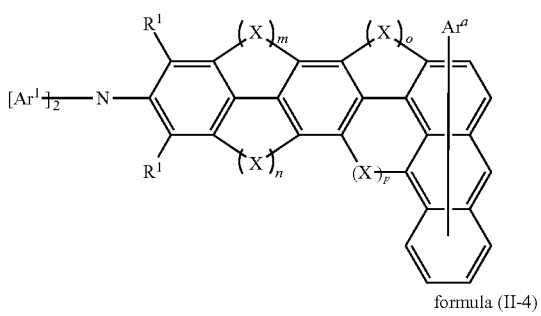
formula (II-4)

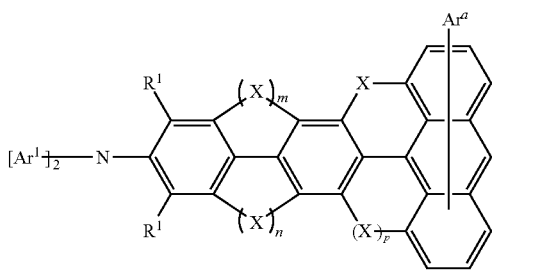

formula (II-5)

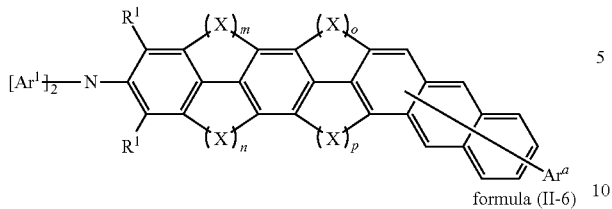

formula (II-6)

formula (II-7)

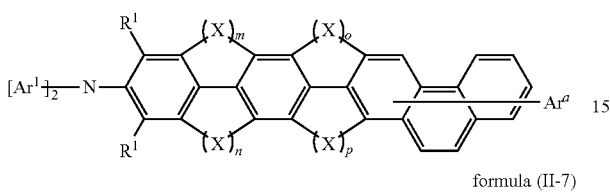

formula (II-8)

formula (II-9)

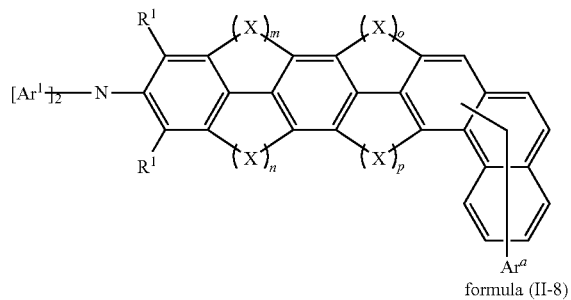

formula (II-10)

formula (II-11)

formula (II-12)

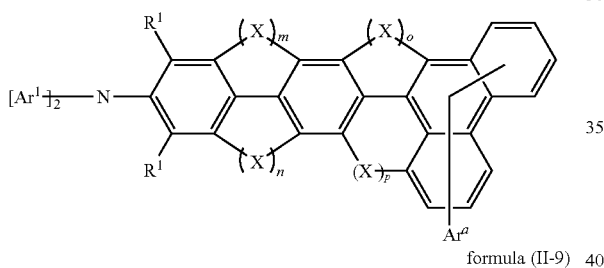

where the symbols and indices occurring are as defined above and where $Ar^a$ can be bonded to the terminal aryl group at any desired free position and where the terminal aryl group may be substituted by groups $R^1$ at each of the other free positions.

The preferred embodiments indicated above for the symbols and indices, in particular those for $Ar^a$, preferably apply.

It is preferred in the above formulae for m and p to be equal to 1 and for n and o to be equal to 0. Alternatively, it is preferred for in above formulae for n and o to be equal to 1 and for m and p to be equal to 0.

Preferred embodiments of formula (III) conform to the following formulae (III-1) to (III-4):

formula (III-1)

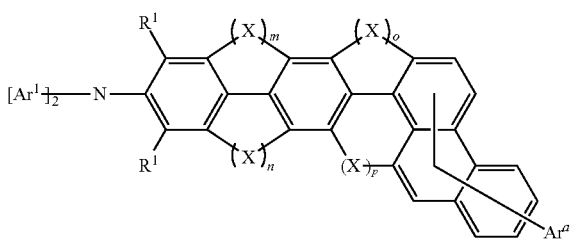

-continued

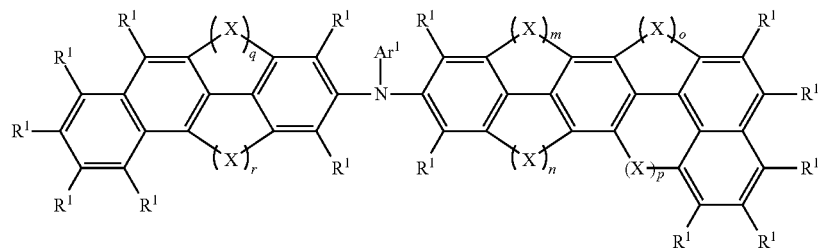

formula (III-2)

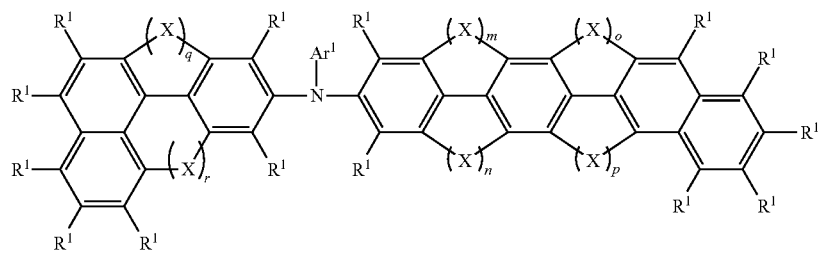

formula (III-3)

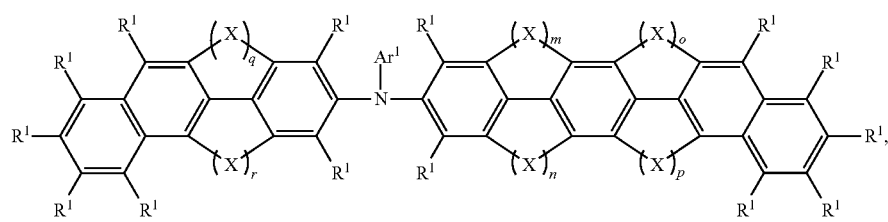

formula (III-4)

where the symbols and indices occurring are as defined above. The preferred embodiments indicated above for the symbols and indices preferably apply.

Of the formulae (III-1) to (III-4) depicted, particular preference is given to formula (III-1).

It is preferred for the above-mentioned formulae for m and p to be equal to 1 and for n and o to be equal to 0. Alternatively, it is preferred for in above formulae for n and o to be equal to 1 and for m and p to be equal to 0. It is furthermore preferred for in above formulae for q to be equal to 0 and for r to be equal to 1. Alternatively, it is preferred for the above-mentioned formulae for q to be equal to 1 and for r to be equal to 0.

It is furthermore preferred for the above-mentioned formulae for at least one of the groups $R^1$ depicted, preferably at least one of the groups $R^1$ on the unit to the left of the nitrogen atom, to be selected from aromatic or heteroaromatic ring systems having 5 to 30 aromatic ring atoms, which may be substituted by one or more radicals $R^2$, particularly preferably from aryl or heteroaryl groups having 6 to 16 aromatic ring atoms, which may be substituted by one or more radicals $R^2$.

Compounds of the formulae (I) and (II) particularly preferably conform to the following formulae:

| Formula | Parent structure | $Ar^1$ (optionally substituted by one or more $R^1$) | $Ar^a$ (optionally substituted by one or more $R^1$) | m | n | o | p |
|---|---|---|---|---|---|---|---|
| (I-1-1) | Formula (I-1) | Phenyl | — | 1 | 0 | 1 | 0 |
| (I-1-2) | " | " | — | 1 | 0 | 0 | 1 |
| (I-1-3) | " | " | — | 0 | 1 | 1 | 0 |
| (I-1-4) | " | " | — | 0 | 1 | 0 | 1 |
| (I-1-5) | " | Naphthyl | — | 1 | 0 | 1 | 0 |
| (I-1-6) | " | " | — | 1 | 0 | 0 | 1 |
| (I-1-7) | " | " | — | 0 | 1 | 1 | 0 |
| (I-1-8) | " | " | — | 0 | 1 | 0 | 1 |
| (I-1-9) | " | Fluorenyl | — | 1 | 0 | 1 | 0 |
| (I-1-10) | " | " | — | 1 | 0 | 0 | 1 |
| (I-1-11) | " | " | — | 0 | 1 | 1 | 0 |
| (I-1-12) | " | " | — | 0 | 1 | 0 | 1 |
| (I-1-13) | " | Dibenzofuranyl | — | 1 | 0 | 1 | 0 |
| (I-1-14) | " | " | — | 1 | 0 | 0 | 1 |
| (I-1-15) | " | " | — | 0 | 1 | 1 | 0 |
| (I-1-16) | " | " | — | 0 | 1 | 0 | 1 |
| (I-1-17) | " | Dibenzothiophenyl | — | 1 | 0 | 1 | 0 |
| (I-1-18) | " | " | — | 1 | 0 | 0 | 1 |
| (I-1-19) | " | " | — | 0 | 1 | 1 | 0 |
| (I-1-20) | " | " | — | 0 | 1 | 0 | 1 |

-continued

| Formula | Parent structure | Ar$^1$ (optionally substituted by one or more R$^1$) | Ar$^a$ (optionally substituted by one or more R$^1$) | m | n | o | p |
|---|---|---|---|---|---|---|---|
| (I-2-1) | Formula (I-2) | Phenyl | — | 1 | 0 | 1 | 0 |
| (I-2-2) | " | " | — | 1 | 0 | 0 | 1 |
| (I-2-3) | " | " | — | 0 | 1 | 1 | 0 |
| (I-2-4) | " | " | — | 0 | 1 | 0 | 1 |
| (I-2-5) | " | Naphthyl | — | 1 | 0 | 1 | 0 |
| (I-2-6) | " | " | — | 1 | 0 | 0 | 1 |
| (I-2-7) | " | " | — | 0 | 1 | 1 | 0 |
| (I-2-8) | " | " | — | 0 | 1 | 0 | 1 |
| (I-2-9) | " | Fluorenyl | — | 1 | 0 | 1 | 0 |
| (I-2-10) | " | " | — | 1 | 0 | 0 | 1 |
| (I-2-11) | " | " | — | 0 | 1 | 1 | 0 |
| (I-2-12) | " | " | — | 0 | 1 | 0 | 1 |
| (I-2-13) | " | Dibenzofuranyl | — | 1 | 0 | 1 | 0 |
| (I-2-14) | " | " | — | 1 | 0 | 0 | 1 |
| (I-2-15) | " | " | — | 0 | 1 | 1 | 0 |
| (I-2-16) | " | " | — | 0 | 1 | 0 | 1 |
| (I-2-17) | " | Dibenzothiophenyl | — | 1 | 0 | 1 | 0 |
| (I-2-18) | " | " | — | 1 | 0 | 0 | 1 |
| (I-2-19) | " | " | — | 0 | 1 | 1 | 0 |
| (I-2-20) | " | " | — | 0 | 1 | 0 | 1 |
| (I-3-1) | Formula (I-3) | Phenyl | — | 1 | 0 | 1 | 0 |
| (I-3-2) | " | " | — | 1 | 0 | 0 | 1 |
| (I-3-3) | " | " | — | 0 | 1 | 1 | 0 |
| (I-3-4) | " | " | — | 0 | 1 | 0 | 1 |
| (I-3-5) | " | Naphthyl | — | 1 | 0 | 1 | 0 |
| (I-3-6) | " | " | — | 1 | 0 | 0 | 1 |
| (I-3-7) | " | " | — | 0 | 1 | 1 | 0 |
| (I-3-8) | " | " | — | 0 | 1 | 0 | 1 |
| (I-3-9) | " | Fluorenyl | — | 1 | 0 | 1 | 0 |
| (I-3-10) | " | " | — | 1 | 0 | 0 | 1 |
| (I-3-11) | " | " | — | 0 | 1 | 1 | 0 |
| (I-3-12) | " | " | — | 0 | 1 | 0 | 1 |
| (I-3-13) | " | Dibenzofuranyl | — | 1 | 0 | 1 | 0 |
| (I-3-14) | " | " | — | 1 | 0 | 0 | 1 |
| (I-3-15) | " | " | — | 0 | 1 | 1 | 0 |
| (I-3-16) | " | " | — | 0 | 1 | 0 | 1 |
| (I-3-17) | " | Dibenzothiophenyl | — | 1 | 0 | 1 | 0 |
| (I-3-18) | " | " | — | 1 | 0 | 0 | 1 |
| (I-3-19) | " | " | — | 0 | 1 | 1 | 0 |
| (I-3-20) | " | " | — | 0 | 1 | 0 | 1 |
| (I-4-1) | Formula (I-4) | Phenyl | — | 1 | 0 | 1 | 0 |
| (I-4-2) | " | " | — | 1 | 0 | 0 | 1 |
| (I-4-3) | " | " | — | 0 | 1 | 1 | 0 |
| (I-4-4) | " | " | — | 0 | 1 | 0 | 1 |
| (I-4-5) | " | Naphthyl | — | 1 | 0 | 1 | 0 |
| (I-4-6) | " | " | — | 1 | 0 | 0 | 1 |
| (I-4-7) | " | " | — | 0 | 1 | 1 | 0 |
| (I-4-8) | " | " | — | 0 | 1 | 0 | 1 |
| (I-4-9) | " | Fluorenyl | — | 1 | 0 | 1 | 0 |
| (I-4-10) | " | " | — | 1 | 0 | 0 | 1 |
| (I-4-11) | " | " | — | 0 | 1 | 1 | 0 |
| (I-4-12) | " | " | — | 0 | 1 | 0 | 1 |
| (I-4-13) | " | Dibenzofuranyl | — | 1 | 0 | 1 | 0 |
| (I-4-14) | " | " | — | 1 | 0 | 0 | 1 |
| (I-4-15) | " | " | — | 0 | 1 | 1 | 0 |
| (I-4-16) | " | " | — | 0 | 1 | 0 | 1 |
| (I-4-17) | " | Dibenzothiophenyl | — | 1 | 0 | 1 | 0 |
| (I-4-18) | " | " | — | 1 | 0 | 0 | 1 |
| (I-4-19) | " | " | — | 0 | 1 | 1 | 0 |
| (I-4-20) | " | " | — | 0 | 1 | 0 | 1 |
| (I-5-1) | Formula (I-5) | Phenyl | — | 1 | 0 | 1 | 0 |
| (I-5-2) | " | " | — | 1 | 0 | 0 | 1 |
| (I-5-3) | " | " | — | 0 | 1 | 1 | 0 |
| (I-5-4) | " | " | — | 0 | 1 | 0 | 1 |
| (I-5-5) | " | Naphthyl | — | 1 | 0 | 1 | 0 |
| (I-5-6) | " | " | — | 1 | 0 | 0 | 1 |
| (I-5-7) | " | " | — | 0 | 1 | 1 | 0 |
| (I-5-8) | " | " | — | 0 | 1 | 0 | 1 |
| (I-5-9) | " | Fluorenyl | — | 1 | 0 | 1 | 0 |
| (I-5-10) | " | " | — | 1 | 0 | 0 | 1 |
| (I-5-11) | " | " | — | 0 | 1 | 1 | 0 |
| (I-5-12) | " | " | — | 0 | 1 | 0 | 1 |
| (I-5-13) | " | Dibenzofuranyl | — | 1 | 0 | 1 | 0 |
| (I-5-14) | " | " | — | 1 | 0 | 0 | 1 |
| (I-5-15) | " | " | — | 0 | 1 | 1 | 0 |

-continued

| Formula | Parent structure | Ar¹ (optionally substituted by one or more R¹) | Ar^a (optionally substituted by one or more R¹) | m | n | o | p |
|---|---|---|---|---|---|---|---|
| (I-5-16) | " | " | — | 0 | 1 | 0 | 1 |
| (I-5-17) | " | Dibenzothiophenyl | — | 1 | 0 | 1 | 0 |
| (I-5-18) | " | " | — | 1 | 0 | 0 | 1 |
| (I-5-19) | " | " | — | 0 | 1 | 1 | 0 |
| (I-5-20) | " | " | — | 0 | 1 | 0 | 1 |
| (I-6-1) | Formula (I-6) | Phenyl | — | 1 | 0 | 1 | 0 |
| (I-6-2) | " | " | — | 1 | 0 | 0 | 1 |
| (I-6-3) | " | " | — | 0 | 1 | 1 | 0 |
| (I-6-4) | " | " | — | 0 | 1 | 0 | 1 |
| (I-6-5) | " | Naphthyl | — | 1 | 0 | 1 | 0 |
| (I-6-6) | " | " | — | 1 | 0 | 0 | 1 |
| (I-6-7) | " | " | — | 0 | 1 | 1 | 0 |
| (I-6-8) | " | " | — | 0 | 1 | 0 | 1 |
| (I-6-9) | " | Fluorenyl | — | 1 | 0 | 1 | 0 |
| (I-6-10) | " | " | — | 1 | 0 | 0 | 1 |
| (I-6-11) | " | " | — | 0 | 1 | 1 | 0 |
| (I-6-12) | " | " | — | 0 | 1 | 0 | 1 |
| (I-6-13) | " | Dibenzofuranyl | — | 1 | 0 | 1 | 0 |
| (I-6-14) | " | " | — | 1 | 0 | 0 | 1 |
| (I-6-15) | " | " | — | 0 | 1 | 1 | 0 |
| (I-6-16) | " | " | — | 0 | 1 | 0 | 1 |
| (I-6-17) | " | Dibenzothiophenyl | — | 1 | 0 | 1 | 0 |
| (I-6-18) | " | " | — | 1 | 0 | 0 | 1 |
| (I-6-19) | " | " | — | 0 | 1 | 1 | 0 |
| (I-6-20) | " | " | — | 0 | 1 | 0 | 1 |
| (I-7-1) | Formula (I-7) | Phenyl | — | 1 | 0 | 1 | 0 |
| (I-7-2) | " | " | — | 1 | 0 | 0 | 1 |
| (I-7-3) | " | " | — | 0 | 1 | 1 | 0 |
| (I-7-4) | " | " | — | 0 | 1 | 0 | 1 |
| (I-7-5) | " | Naphthyl | — | 1 | 0 | 1 | 0 |
| (I-7-6) | " | " | — | 1 | 0 | 0 | 1 |
| (I-7-7) | " | " | — | 0 | 1 | 1 | 0 |
| (I-7-8) | " | " | — | 0 | 1 | 0 | 1 |
| (I-7-9) | " | Fluorenyl | — | 1 | 0 | 1 | 0 |
| (I-7-10) | " | " | — | 1 | 0 | 0 | 1 |
| (I-7-11) | " | " | — | 0 | 1 | 1 | 0 |
| (I-7-12) | " | " | — | 0 | 1 | 0 | 1 |
| (I-7-13) | " | Dibenzofuranyl | — | 1 | 0 | 1 | 0 |
| (I-7-14) | " | " | — | 1 | 0 | 0 | 1 |
| (I-7-15) | " | " | — | 0 | 1 | 1 | 0 |
| (I-7-16) | " | " | — | 0 | 1 | 0 | 1 |
| (I-7-17) | " | Dibenzothiophenyl | — | 1 | 0 | 1 | 0 |
| (I-7-18) | " | " | — | 1 | 0 | 0 | 1 |
| (I-7-19) | " | " | — | 0 | 1 | 1 | 0 |
| (I-7-20) | " | " | — | 0 | 1 | 0 | 1 |
| (I-8-1) | Formula (I-8) | Phenyl | — | 1 | 0 | 1 | 0 |
| (I-8-2) | " | " | — | 1 | 0 | 0 | 1 |
| (I-8-3) | " | " | — | 0 | 1 | 1 | 0 |
| (I-8-4) | " | " | — | 0 | 1 | 0 | 1 |
| (I-8-5) | " | Naphthyl | — | 1 | 0 | 1 | 0 |
| (I-8-6) | " | " | — | 1 | 0 | 0 | 1 |
| (I-8-7) | " | " | — | 0 | 1 | 1 | 0 |
| (I-8-8) | " | " | — | 0 | 1 | 0 | 1 |
| (I-8-9) | " | Fluorenyl | — | 1 | 0 | 1 | 0 |
| (I-8-10) | " | " | — | 1 | 0 | 0 | 1 |
| (I-8-11) | " | " | — | 0 | 1 | 1 | 0 |
| (I-8-12) | " | " | — | 0 | 1 | 0 | 1 |
| (I-8-13) | " | Dibenzofuranyl | — | 1 | 0 | 1 | 0 |
| (I-8-14) | " | " | — | 1 | 0 | 0 | 1 |
| (I-8-15) | " | " | — | 0 | 1 | 1 | 0 |
| (I-8-16) | " | " | — | 0 | 1 | 0 | 1 |
| (I-8-17) | " | Dibenzothiophenyl | — | 1 | 0 | 1 | 0 |
| (I-8-18) | " | " | — | 1 | 0 | 0 | 1 |
| (I-8-19) | " | " | — | 0 | 1 | 1 | 0 |
| (I-8-20) | " | " | — | 0 | 1 | 0 | 1 |
| (I-9-1) | Formula (I-9) | Phenyl | — | 1 | 0 | 1 | 0 |
| (I-9-2) | " | " | — | 1 | 0 | 0 | 1 |
| (I-9-3) | " | " | — | 0 | 1 | 1 | 0 |
| (I-9-4) | " | " | — | 0 | 1 | 0 | 1 |
| (I-9-5) | " | Naphthyl | — | 1 | 0 | 1 | 0 |
| (I-9-6) | " | " | — | 1 | 0 | 0 | 1 |
| (I-9-7) | " | " | — | 0 | 1 | 1 | 0 |
| (I-9-8) | " | " | — | 0 | 1 | 0 | 1 |
| (I-9-9) | " | Fluorenyl | — | 1 | 0 | 1 | 0 |
| (I-9-10) | " | " | — | 1 | 0 | 0 | 1 |

-continued

| Formula | Parent structure | Ar¹ (optionally substituted by one or more R¹) | Ar^a (optionally substituted by one or more R¹) | m | n | o | p |
|---|---|---|---|---|---|---|---|
| (I-9-11) | " | " | — | 0 | 1 | 1 | 0 |
| (I-9-12) | " | " | — | 0 | 1 | 0 | 1 |
| (I-9-13) | " | Dibenzofuranyl | — | 1 | 0 | 1 | 0 |
| (I-9-14) | " | " | — | 1 | 0 | 0 | 1 |
| (I-9-15) | " | " | — | 0 | 1 | 1 | 0 |
| (I-9-16) | " | " | — | 0 | 1 | 0 | 1 |
| (I-9-17) | " | Dibenzothiophenyl | — | 1 | 0 | 1 | 0 |
| (I-9-18) | " | " | — | 1 | 0 | 0 | 1 |
| (I-9-19) | " | " | — | 0 | 1 | 1 | 0 |
| (I-9-20) | " | " | — | 0 | 1 | 0 | 1 |
| (I-10-1) | Formula (I-10) | Phenyl | — | 1 | 0 | 1 | 0 |
| (I-10-2) | " | " | — | 1 | 0 | 0 | 1 |
| (I-10-3) | " | " | — | 0 | 1 | 1 | 0 |
| (I-10-4) | " | " | — | 0 | 1 | 0 | 1 |
| (I-10-5) | " | Naphthyl | — | 1 | 0 | 1 | 0 |
| (I-10-6) | " | " | — | 1 | 0 | 0 | 1 |
| (I-10-7) | " | " | — | 0 | 1 | 1 | 0 |
| (I-10-8) | " | " | — | 0 | 1 | 0 | 1 |
| (I-10-9) | " | Fluorenyl | — | 1 | 0 | 1 | 0 |
| (I-10-10) | " | " | — | 1 | 0 | 0 | 1 |
| (I-10-11) | " | " | — | 0 | 1 | 1 | 0 |
| (I-10-12) | " | " | — | 0 | 1 | 0 | 1 |
| (I-10-13) | " | Dibenzofuranyl | — | 1 | 0 | 1 | 0 |
| (I-10-14) | " | " | — | 1 | 0 | 0 | 1 |
| (I-10-15) | " | " | — | 0 | 1 | 1 | 0 |
| (I-10-16) | " | " | — | 0 | 1 | 0 | 1 |
| (I-10-17) | " | Dibenzothiophenyl | — | 1 | 0 | 1 | 0 |
| (I-10-18) | " | " | — | 1 | 0 | 0 | 1 |
| (I-10-19) | " | " | — | 0 | 1 | 1 | 0 |
| (I-10-20) | " | " | — | 0 | 1 | 0 | 1 |
| (I-11-1) | Formula (I-11) | Phenyl | — | 1 | 0 | 1 | 0 |
| (I-11-2) | " | " | — | 1 | 0 | 0 | 1 |
| (I-11-3) | " | " | — | 0 | 1 | 1 | 0 |
| (I-11-4) | " | " | — | 0 | 1 | 0 | 1 |
| (I-11-5) | " | Naphthyl | — | 1 | 0 | 1 | 0 |
| (I-11-6) | " | " | — | 1 | 0 | 0 | 1 |
| (I-11-7) | " | " | — | 0 | 1 | 1 | 0 |
| (I-11-8) | " | " | — | 0 | 1 | 0 | 1 |
| (I-11-9) | " | Fluorenyl | — | 1 | 0 | 1 | 0 |
| (I-11-10) | " | " | — | 1 | 0 | 0 | 1 |
| (I-11-11) | " | " | — | 0 | 1 | 1 | 0 |
| (I-11-12) | " | " | — | 0 | 1 | 0 | 1 |
| (I-11-13) | " | Dibenzofuranyl | — | 1 | 0 | 1 | 0 |
| (I-11-14) | " | " | — | 1 | 0 | 0 | 1 |
| (I-11-15) | " | " | — | 0 | 1 | 1 | 0 |
| (I-11-16) | " | " | — | 0 | 1 | 0 | 1 |
| (I-11-17) | " | Dibenzothiophenyl | — | 1 | 0 | 1 | 0 |
| (I-11-18) | " | " | — | 1 | 0 | 0 | 1 |
| (I-11-19) | " | " | — | 0 | 1 | 1 | 0 |
| (I-11-20) | " | " | — | 0 | 1 | 0 | 1 |
| (I-12-1) | Formula (I-12) | Phenyl | — | 1 | 0 | 1 | 0 |
| (I-12-2) | " | " | — | 1 | 0 | 0 | 1 |
| (I-12-3) | " | " | — | 0 | 1 | 1 | 0 |
| (I-12-4) | " | " | — | 0 | 1 | 0 | 1 |
| (I-12-5) | " | Naphthyl | — | 1 | 0 | 1 | 0 |
| (I-12-6) | " | " | — | 1 | 0 | 0 | 1 |
| (I-12-7) | " | " | — | 0 | 1 | 1 | 0 |
| (I-12-8) | " | " | — | 0 | 1 | 0 | 1 |
| (I-12-9) | " | Fluorenyl | — | 1 | 0 | 1 | 0 |
| (I-12-10) | " | " | — | 1 | 0 | 0 | 1 |
| (I-12-11) | " | " | — | 0 | 1 | 1 | 0 |
| (I-12-12) | " | " | — | 0 | 1 | 0 | 1 |
| (I-12-13) | " | Dibenzofuranyl | — | 1 | 0 | 1 | 0 |
| (I-12-14) | " | " | — | 1 | 0 | 0 | 1 |
| (I-12-15) | " | " | — | 0 | 1 | 1 | 0 |
| (I-12-16) | " | " | — | 0 | 1 | 0 | 1 |
| (I-12-17) | " | Dibenzothiophenyl | — | 1 | 0 | 1 | 0 |
| (I-12-18) | " | " | — | 1 | 0 | 0 | 1 |
| (I-12-19) | " | " | — | 0 | 1 | 1 | 0 |
| (I-12-20) | " | " | — | 0 | 1 | 0 | 1 |
| (II-1-1) | Formula (II-1) | Phenyl | Phenyl | 1 | 0 | 1 | 0 |
| (II-1-2) | " | " | " | 1 | 0 | 0 | 1 |
| (II-1-3) | " | " | " | 0 | 1 | 1 | 0 |
| (II-1-4) | " | " | " | 0 | 1 | 0 | 1 |
| (II-1-5) | " | " | Naphthyl | 1 | 0 | 1 | 0 |

| Formula | Parent structure | Ar¹ (optionally substituted by one or more $R^1$) | $Ar^a$ (optionally substituted by one or more $R^1$) | m | n | o | p |
|---|---|---|---|---|---|---|---|
| (II-1-6) | " | " | " | 1 | 0 | 0 | 1 |
| (II-1-7) | " | " | " | 0 | 1 | 1 | 0 |
| (II-1-8) | " | " | " | 0 | 1 | 0 | 1 |
| (II-1-9) | " | Naphthyl | Phenyl | 1 | 0 | 1 | 0 |
| (II-1-10) | " | " | " | 1 | 0 | 0 | 1 |
| (II-1-11) | " | " | " | 0 | 1 | 1 | 0 |
| (II-1-12) | " | " | " | 0 | 1 | 0 | 1 |
| (II-1-13) | " | " | Naphthyl | 1 | 0 | 1 | 0 |
| (II-1-14) | " | " | " | 1 | 0 | 0 | 1 |
| (II-1-15) | " | " | " | 0 | 1 | 1 | 0 |
| (II-1-16) | " | " | " | 0 | 1 | 0 | 1 |
| (II-1-17) | " | Fluorenyl | Phenyl | 1 | 0 | 1 | 0 |
| (II-1-18) | " | " | " | 1 | 0 | 0 | 1 |
| (II-1-19) | " | " | " | 0 | 1 | 1 | 0 |
| (II-1-20) | " | " | " | 0 | 1 | 0 | 1 |
| (II-1-21) | " | " | Naphthyl | 1 | 0 | 1 | 0 |
| (II-1-22) | " | " | " | 1 | 0 | 0 | 1 |
| (II-1-23) | " | " | " | 0 | 1 | 1 | 0 |
| (II-1-24) | " | " | " | 0 | 1 | 0 | 1 |
| (II-1-25) | " | Dibenzofuranyl | Phenyl | 1 | 0 | 1 | 0 |
| (II-1-26) | " | " | " | 1 | 0 | 0 | 1 |
| (II-1-27) | " | " | " | 0 | 1 | 1 | 0 |
| (II-1-28) | " | " | " | 0 | 1 | 0 | 1 |
| (II-1-29) | " | " | Naphthyl | 1 | 0 | 1 | 0 |
| (II-1-30) | " | " | " | 1 | 0 | 0 | 1 |
| (II-1-31) | " | " | " | 0 | 1 | 1 | 0 |
| (II-1-32) | " | " | " | 0 | 1 | 0 | 1 |
| (II-1-33) | " | Dibenzothiophenyl | Phenyl | 1 | 0 | 1 | 0 |
| (II-1-34) | " | " | " | 1 | 0 | 0 | 1 |
| (II-1-35) | " | " | " | 0 | 1 | 1 | 0 |
| (II-1-36) | " | " | " | 0 | 1 | 0 | 1 |
| (II-1-37) | " | " | Naphthyl | 1 | 0 | 1 | 0 |
| (II-1-38) | " | " | " | 1 | 0 | 0 | 1 |
| (II-1-39) | " | " | " | 0 | 1 | 1 | 0 |
| (II-1-40) | " | " | " | 0 | 1 | 0 | 1 |
| (II-2-1) | Formula (II-2) | Phenyl | Phenyl | 1 | 0 | 1 | 0 |
| (II-2-2) | " | " | " | 1 | 0 | 0 | 1 |
| (II-2-3) | " | " | " | 0 | 1 | 1 | 0 |
| (II-2-4) | " | " | " | 0 | 1 | 0 | 1 |
| (II-2-5) | " | " | Naphthyl | 1 | 0 | 1 | 0 |
| (II-2-6) | " | " | " | 1 | 0 | 0 | 1 |
| (II-2-7) | " | " | " | 0 | 1 | 1 | 0 |
| (II-2-8) | " | " | " | 0 | 1 | 0 | 1 |
| (II-2-9) | " | Naphthyl | Phenyl | 1 | 0 | 1 | 0 |
| (II-2-10) | " | " | " | 1 | 0 | 0 | 1 |
| (II-2-11) | " | " | " | 0 | 1 | 1 | 0 |
| (II-2-12) | " | " | " | 0 | 1 | 0 | 1 |
| (II-2-13) | " | " | Naphthyl | 1 | 0 | 1 | 0 |
| (II-2-14) | " | " | " | 1 | 0 | 0 | 1 |
| (II-2-15) | " | " | " | 0 | 1 | 1 | 0 |
| (II-2-16) | " | " | " | 0 | 1 | 0 | 1 |
| (II-2-17) | " | Fluorenyl | Phenyl | 1 | 0 | 1 | 0 |
| (II-2-18) | " | " | " | 1 | 0 | 0 | 1 |
| (II-2-19) | " | " | " | 0 | 1 | 1 | 0 |
| (II-2-20) | " | " | " | 0 | 1 | 0 | 1 |
| (II-2-21) | " | " | Naphthyl | 1 | 0 | 1 | 0 |
| (II-2-22) | " | " | " | 1 | 0 | 0 | 1 |
| (II-2-23) | " | " | " | 0 | 1 | 1 | 0 |
| (II-2-24) | " | " | " | 0 | 1 | 0 | 1 |
| (II-2-25) | " | Dibenzofuranyl | Phenyl | 1 | 0 | 1 | 0 |
| (II-2-26) | " | " | " | 1 | 0 | 0 | 1 |
| (II-2-27) | " | " | " | 0 | 1 | 1 | 0 |
| (II-2-28) | " | " | " | 0 | 1 | 0 | 1 |
| (II-2-29) | " | " | Naphthyl | 1 | 0 | 1 | 0 |
| (II-2-30) | " | " | " | 1 | 0 | 0 | 1 |
| (II-2-31) | " | " | " | 0 | 1 | 1 | 0 |
| (II-2-32) | " | " | " | 0 | 1 | 0 | 1 |
| (II-2-33) | " | Dibenzothiophenyl | Phenyl | 1 | 0 | 1 | 0 |
| (II-2-34) | " | " | " | 1 | 0 | 0 | 1 |
| (II-2-35) | " | " | " | 0 | 1 | 1 | 0 |
| (II-2-36) | " | " | " | 0 | 1 | 0 | 1 |
| (II-2-37) | " | " | Naphthyl | 1 | 0 | 1 | 0 |
| (II-2-38) | " | " | " | 1 | 0 | 0 | 1 |
| (II-2-39) | " | " | " | 0 | 1 | 1 | 0 |
| (II-2-40) | " | " | " | 0 | 1 | 0 | 1 |

-continued

| Formula | Parent structure | Ar¹ (optionally substituted by one or more R¹) | Ar$^a$ (optionally substituted by one or more R¹) | m | n | o | p |
|---|---|---|---|---|---|---|---|
| (II-3-1) | Formula (II-3) | Phenyl | Phenyl | 1 | 0 | 1 | 0 |
| (II-3-2) | " | " | " | 1 | 0 | 0 | 1 |
| (II-3-3) | " | " | " | 0 | 1 | 1 | 0 |
| (II-3-4) | " | " | " | 0 | 1 | 0 | 1 |
| (II-3-5) | " | " | Naphthyl | 1 | 0 | 1 | 0 |
| (II-3-6) | " | " | " | 1 | 0 | 0 | 1 |
| (II-3-7) | " | " | " | 0 | 1 | 1 | 0 |
| (II-3-8) | " | " | " | 0 | 1 | 0 | 1 |
| (II-3-9) | " | Naphthyl | Phenyl | 1 | 0 | 1 | 0 |
| (II-3-10) | " | " | " | 1 | 0 | 0 | 1 |
| (II-3-11) | " | " | " | 0 | 1 | 1 | 0 |
| (II-3-12) | " | " | " | 0 | 1 | 0 | 1 |
| (II-3-13) | " | " | Naphthyl | 1 | 0 | 1 | 0 |
| (II-3-14) | " | " | " | 1 | 0 | 0 | 1 |
| (II-3-15) | " | " | " | 0 | 1 | 1 | 0 |
| (II-3-16) | " | " | " | 0 | 1 | 0 | 1 |
| (II-3-17) | " | Fluorenyl | Phenyl | 1 | 0 | 1 | 0 |
| (II-3-18) | " | " | " | 1 | 0 | 0 | 1 |
| (II-3-19) | " | " | " | 0 | 1 | 1 | 0 |
| (II-3-20) | " | " | " | 0 | 1 | 0 | 1 |
| (II-3-21) | " | " | Naphthyl | 1 | 0 | 1 | 0 |
| (II-3-22) | " | " | " | 1 | 0 | 0 | 1 |
| (II-3-23) | " | " | " | 0 | 1 | 1 | 0 |
| (II-3-24) | " | " | " | 0 | 1 | 0 | 1 |
| (II-3-25) | " | Dibenzofuranyl | Phenyl | 1 | 0 | 1 | 0 |
| (II-3-26) | " | " | " | 1 | 0 | 0 | 1 |
| (II-3-27) | " | " | " | 0 | 1 | 1 | 0 |
| (II-3-28) | " | " | " | 0 | 1 | 0 | 1 |
| (II-3-29) | " | " | Naphthyl | 1 | 0 | 1 | 0 |
| (II-3-30) | " | " | " | 1 | 0 | 0 | 1 |
| (II-3-31) | " | " | " | 0 | 1 | 1 | 0 |
| (II-3-32) | " | " | " | 0 | 1 | 0 | 1 |
| (II-3-33) | " | Dibenzothiophenyl | Phenyl | 1 | 0 | 1 | 0 |
| (II-3-34) | " | " | " | 1 | 0 | 0 | 1 |
| (II-3-35) | " | " | " | 0 | 1 | 1 | 0 |
| (II-3-36) | " | " | " | 0 | 1 | 0 | 1 |
| (II-3-37) | " | " | Naphthyl | 1 | 0 | 1 | 0 |
| (II-3-38) | " | " | " | 1 | 0 | 0 | 1 |
| (II-3-39) | " | " | " | 0 | 1 | 1 | 0 |
| (II-3-40) | " | " | " | 0 | 1 | 0 | 1 |
| (II-4-1) | Formula (II-4) | Phenyl | Phenyl | 1 | 0 | 1 | 0 |
| (II-4-2) | " | " | " | 1 | 0 | 0 | 1 |
| (II-4-3) | " | " | " | 0 | 1 | 1 | 0 |
| (II-4-4) | " | " | " | 0 | 1 | 0 | 1 |
| (II-4-5) | " | " | Naphthyl | 1 | 0 | 1 | 0 |
| (II-4-6) | " | " | " | 1 | 0 | 0 | 1 |
| (II-4-7) | " | " | " | 0 | 1 | 1 | 0 |
| (II-4-8) | " | " | " | 0 | 1 | 0 | 1 |
| (II-4-9) | " | Naphthyl | Phenyl | 1 | 0 | 1 | 0 |
| (II-4-10) | " | " | " | 1 | 0 | 0 | 1 |
| (II-4-11) | " | " | " | 0 | 1 | 1 | 0 |
| (II-4-12) | " | " | " | 0 | 1 | 0 | 1 |
| (II-4-13) | " | " | Naphthyl | 1 | 0 | 1 | 0 |
| (II-4-14) | " | " | " | 1 | 0 | 0 | 1 |
| (II-4-15) | " | " | " | 0 | 1 | 1 | 0 |
| (II-4-16) | " | " | " | 0 | 1 | 0 | 1 |
| (II-4-17) | " | Fluorenyl | Phenyl | 1 | 0 | 1 | 0 |
| (II-4-18) | " | " | " | 1 | 0 | 0 | 1 |
| (II-4-19) | " | " | " | 0 | 1 | 1 | 0 |
| (II-4-20) | " | " | " | 0 | 1 | 0 | 1 |
| (II-4-21) | " | " | Naphthyl | 1 | 0 | 1 | 0 |
| (II-4-22) | " | " | " | 1 | 0 | 0 | 1 |
| (II-4-23) | " | " | " | 0 | 1 | 1 | 0 |
| (II-4-24) | " | " | " | 0 | 1 | 0 | 1 |
| (II-4-25) | " | Dibenzofuranyl | Phenyl | 1 | 0 | 1 | 0 |
| (II-4-26) | " | " | " | 1 | 0 | 0 | 1 |
| (II-4-27) | " | " | " | 0 | 1 | 1 | 0 |
| (II-4-28) | " | " | " | 0 | 1 | 0 | 1 |
| (II-4-29) | " | " | Naphthyl | 1 | 0 | 1 | 0 |
| (II-4-30) | " | " | " | 1 | 0 | 0 | 1 |
| (II-4-31) | " | " | " | 0 | 1 | 1 | 0 |
| (II-4-32) | " | " | " | 0 | 1 | 0 | 1 |
| (II-4-33) | " | Dibenzothiophenyl | Phenyl | 1 | 0 | 1 | 0 |
| (II-4-34) | " | " | " | 1 | 0 | 0 | 1 |
| (II-4-35) | " | " | " | 0 | 1 | 1 | 0 |

-continued

| Formula | Parent structure | Ar¹ (optionally substituted by one or more R¹) | Arᵃ (optionally substituted by one or more R¹) | m | n | o | p |
|---|---|---|---|---|---|---|---|
| (II-4-36) | " | " | " | 0 | 1 | 0 | 1 |
| (II-4-37) | " | " | Naphthyl | 1 | 0 | 1 | 0 |
| (II-4-38) | " | " | " | 1 | 0 | 0 | 1 |
| (II-4-39) | " | " | " | 0 | 1 | 1 | 0 |
| (II-4-40) | " | " | " | 0 | 1 | 0 | 1 |
| (II-5-1) | Formula (II-5) | Phenyl | Phenyl | 1 | 0 | 1 | 0 |
| (II-5-2) | " | " | " | 1 | 0 | 0 | 1 |
| (II-5-3) | " | " | " | 0 | 1 | 1 | 0 |
| (II-5-4) | " | " | " | 0 | 1 | 0 | 1 |
| (II-5-5) | " | " | Naphthyl | 1 | 0 | 1 | 0 |
| (II-5-6) | " | " | " | 1 | 0 | 0 | 1 |
| (II-5-7) | " | " | " | 0 | 1 | 1 | 0 |
| (II-5-8) | " | " | " | 0 | 1 | 0 | 1 |
| (II-5-9) | " | Naphthyl | Phenyl | 1 | 0 | 1 | 0 |
| (II-5-10) | " | " | " | 1 | 0 | 0 | 1 |
| (II-5-11) | " | " | " | 0 | 1 | 1 | 0 |
| (II-5-12) | " | " | " | 0 | 1 | 0 | 1 |
| (II-5-13) | " | " | Naphthyl | 1 | 0 | 1 | 0 |
| (II-5-14) | " | " | " | 1 | 0 | 0 | 1 |
| (II-5-15) | " | " | " | 0 | 1 | 1 | 0 |
| (II-5-16) | " | " | " | 0 | 1 | 0 | 1 |
| (II-5-17) | " | Fluorenyl | Phenyl | 1 | 0 | 1 | 0 |
| (II-5-18) | " | " | " | 1 | 0 | 0 | 1 |
| (II-5-19) | " | " | " | 0 | 1 | 1 | 0 |
| (II-5-20) | " | " | " | 0 | 1 | 0 | 1 |
| (II-5-21) | " | " | Naphthyl | 1 | 0 | 1 | 0 |
| (II-5-22) | " | " | " | 1 | 0 | 0 | 1 |
| (II-5-23) | " | " | " | 0 | 1 | 1 | 0 |
| (II-5-24) | " | " | " | 0 | 1 | 0 | 1 |
| (II-5-25) | " | Dibenzofuranyl | Phenyl | 1 | 0 | 1 | 0 |
| (II-5-26) | " | " | " | 1 | 0 | 0 | 1 |
| (II-5-27) | " | " | " | 0 | 1 | 1 | 0 |
| (II-5-28) | " | " | " | 0 | 1 | 0 | 1 |
| (II-5-29) | " | " | Naphthyl | 1 | 0 | 1 | 0 |
| (II-5-30) | " | " | " | 1 | 0 | 0 | 1 |
| (II-5-31) | " | " | " | 0 | 1 | 1 | 0 |
| (II-5-32) | " | " | " | 0 | 1 | 0 | 1 |
| (II-5-33) | " | Dibenzothiophenyl | Phenyl | 1 | 0 | 1 | 0 |
| (II-5-34) | " | " | " | 1 | 0 | 0 | 1 |
| (II-5-35) | " | " | " | 0 | 1 | 1 | 0 |
| (II-5-36) | " | " | " | 0 | 1 | 0 | 1 |
| (II-5-37) | " | " | Naphthyl | 1 | 0 | 1 | 0 |
| (II-5-38) | " | " | " | 1 | 0 | 0 | 1 |
| (II-5-39) | " | " | " | 0 | 1 | 1 | 0 |
| (II-5-40) | " | " | " | 0 | 1 | 0 | 1 |
| (II-6-1) | Formula (II-6) | Phenyl | Phenyl | 1 | 0 | 1 | 0 |
| (II-6-2) | " | " | " | 1 | 0 | 0 | 1 |
| (II-6-3) | " | " | " | 0 | 1 | 1 | 0 |
| (II-6-4) | " | " | " | 0 | 1 | 0 | 1 |
| (II-6-5) | " | " | Naphthyl | 1 | 0 | 1 | 0 |
| (II-6-6) | " | " | " | 1 | 0 | 0 | 1 |
| (II-6-7) | " | " | " | 0 | 1 | 1 | 0 |
| (II-6-8) | " | " | " | 0 | 1 | 0 | 1 |
| (II-6-9) | " | Naphthyl | Phenyl | 1 | 0 | 1 | 0 |
| (II-6-10) | " | " | " | 1 | 0 | 0 | 1 |
| (II-6-11) | " | " | " | 0 | 1 | 1 | 0 |
| (II-6-12) | " | " | " | 0 | 1 | 0 | 1 |
| (II-6-13) | " | " | Naphthyl | 1 | 0 | 1 | 0 |
| (II-6-14) | " | " | " | 1 | 0 | 0 | 1 |
| (II-6-15) | " | " | " | 0 | 1 | 1 | 0 |
| (II-6-16) | " | " | " | 0 | 1 | 0 | 1 |
| (II-6-17) | " | Fluorenyl | Phenyl | 1 | 0 | 1 | 0 |
| (II-6-18) | " | " | " | 1 | 0 | 0 | 1 |
| (II-6-19) | " | " | " | 0 | 1 | 1 | 0 |
| (II-6-20) | " | " | " | 0 | 1 | 0 | 1 |
| (II-6-21) | " | " | Naphthyl | 1 | 0 | 1 | 0 |
| (II-6-22) | " | " | " | 1 | 0 | 0 | 1 |
| (II-6-23) | " | " | " | 0 | 1 | 1 | 0 |
| (II-6-24) | " | " | " | 0 | 1 | 0 | 1 |
| (II-6-25) | " | Dibenzofuranyl | Phenyl | 1 | 0 | 1 | 0 |
| (II-6-26) | " | " | " | 1 | 0 | 0 | 1 |
| (II-6-27) | " | " | " | 0 | 1 | 1 | 0 |
| (II-6-28) | " | " | " | 0 | 1 | 0 | 1 |
| (II-6-29) | " | " | Naphthyl | 1 | 0 | 1 | 0 |
| (II-6-30) | " | " | " | 1 | 0 | 0 | 1 |

| Formula | Parent structure | Ar¹ (optionally substituted by one or more R¹) | Ar² (optionally substituted by one or more R¹) | m | n | o | p |
|---|---|---|---|---|---|---|---|
| (II-6-31) | " | " | " | 0 | 1 | 1 | 0 |
| (II-6-32) | " | " | " | 0 | 1 | 0 | 1 |
| (II-6-33) | " | Dibenzothiophenyl | Phenyl | 1 | 0 | 1 | 0 |
| (II-6-34) | " | " | " | 1 | 0 | 0 | 1 |
| (II-6-35) | " | " | " | 0 | 1 | 1 | 0 |
| (II-6-36) | " | " | " | 0 | 1 | 0 | 1 |
| (II-6-37) | " | " | Naphthyl | 1 | 0 | 1 | 0 |
| (II-6-38) | " | " | " | 1 | 0 | 0 | 1 |
| (II-6-39) | " | " | " | 0 | 1 | 1 | 0 |
| (II-6-40) | " | " | " | 0 | 1 | 0 | 1 |
| (II-7-1) | Formula (II-7) | Phenyl | Phenyl | 1 | 0 | 1 | 0 |
| (II-7-2) | " | " | " | 1 | 0 | 0 | 1 |
| (II-7-3) | " | " | " | 0 | 1 | 1 | 0 |
| (II-7-4) | " | " | " | 0 | 1 | 0 | 1 |
| (II-7-5) | " | " | Naphthyl | 1 | 0 | 1 | 0 |
| (II-7-6) | " | " | " | 1 | 0 | 0 | 1 |
| (II-7-7) | " | " | " | 0 | 1 | 1 | 0 |
| (II-7-8) | " | " | " | 0 | 1 | 0 | 1 |
| (II-7-9) | " | Naphthyl | Phenyl | 1 | 0 | 1 | 0 |
| (II-7-10) | " | " | " | 1 | 0 | 0 | 1 |
| (II-7-11) | " | " | " | 0 | 1 | 1 | 0 |
| (II-7-12) | " | " | " | 0 | 1 | 0 | 1 |
| (II-7-13) | " | " | Naphthyl | 1 | 0 | 1 | 0 |
| (II-7-14) | " | " | " | 1 | 0 | 0 | 1 |
| (II-7-15) | " | " | " | 0 | 1 | 1 | 0 |
| (II-7-16) | " | " | " | 0 | 1 | 0 | 1 |
| (II-7-17) | " | Fluorenyl | Phenyl | 1 | 0 | 1 | 0 |
| (II-7-18) | " | " | " | 1 | 0 | 0 | 1 |
| (II-7-19) | " | " | " | 0 | 1 | 1 | 0 |
| (II-7-20) | " | " | " | 0 | 1 | 0 | 1 |
| (II-7-21) | " | " | Naphthyl | 1 | 0 | 1 | 0 |
| (II-7-22) | " | " | " | 1 | 0 | 0 | 1 |
| (II-7-23) | " | " | " | 0 | 1 | 1 | 0 |
| (II-7-24) | " | " | " | 0 | 1 | 0 | 1 |
| (II-8-1) | Formula (II-8) | Phenyl | Phenyl | 1 | 0 | 1 | 0 |
| (II-8-2) | " | " | " | 1 | 0 | 0 | 1 |
| (II-8-3) | " | " | " | 0 | 1 | 1 | 0 |
| (II-8-4) | " | " | " | 0 | 1 | 0 | 1 |
| (II-8-5) | " | " | Naphthyl | 1 | 0 | 1 | 0 |
| (II-8-6) | " | " | " | 1 | 0 | 0 | 1 |
| (II-8-7) | " | " | " | 0 | 1 | 1 | 0 |
| (II-8-8) | " | " | " | 0 | 1 | 0 | 1 |
| (II-8-9) | " | Naphthyl | Phenyl | 1 | 0 | 1 | 0 |
| (II-8-10) | " | " | " | 1 | 0 | 0 | 1 |
| (II-8-11) | " | " | " | 0 | 1 | 1 | 0 |
| (II-8-12) | " | " | " | 0 | 1 | 0 | 1 |
| (II-8-13) | " | " | Naphthyl | 1 | 0 | 1 | 0 |
| (II-8-14) | " | " | " | 1 | 0 | 0 | 1 |
| (II-8-15) | " | " | " | 0 | 1 | 1 | 0 |
| (II-8-16) | " | " | " | 0 | 1 | 0 | 1 |
| (II-8-17) | " | Fluorenyl | Phenyl | 1 | 0 | 1 | 0 |
| (II-8-18) | " | " | " | 1 | 0 | 0 | 1 |
| (II-8-19) | " | " | " | 0 | 1 | 1 | 0 |
| (II-8-20) | " | " | " | 0 | 1 | 0 | 1 |
| (II-8-21) | " | " | Naphthyl | 1 | 0 | 1 | 0 |
| (II-8-22) | " | " | " | 1 | 0 | 0 | 1 |
| (II-8-23) | " | " | " | 0 | 1 | 1 | 0 |
| (II-8-24) | " | " | " | 0 | 1 | 0 | 1 |
| (II-8-25) | " | Dibenzofuranyl | Phenyl | 1 | 0 | 1 | 0 |
| (II-8-26) | " | " | " | 1 | 0 | 0 | 1 |
| (II-8-27) | " | " | " | 0 | 1 | 1 | 0 |
| (II-8-28) | " | " | " | 0 | 1 | 0 | 1 |
| (II-8-29) | " | " | Naphthyl | 1 | 0 | 1 | 0 |
| (II-8-30) | " | " | " | 1 | 0 | 0 | 1 |
| (II-8-31) | " | " | " | 0 | 1 | 1 | 0 |
| (II-8-32) | " | " | " | 0 | 1 | 0 | 1 |
| (II-8-33) | " | Dibenzothiophenyl | Phenyl | 1 | 0 | 1 | 0 |
| (II-8-34) | " | " | " | 1 | 0 | 0 | 1 |
| (II-8-35) | " | " | " | 0 | 1 | 1 | 0 |
| (II-8-36) | " | " | " | 0 | 1 | 0 | 1 |
| (II-8-37) | " | " | Naphthyl | 1 | 0 | 1 | 0 |
| (II-8-38) | " | " | " | 1 | 0 | 0 | 1 |
| (II-8-39) | " | " | " | 0 | 1 | 1 | 0 |
| (II-8-40) | " | " | " | 0 | 1 | 0 | 1 |
| (II-9-1) | Formula (II-9) | Phenyl | Phenyl | 1 | 0 | 1 | 0 |

-continued

| Formula | Parent structure | Ar¹ (optionally substituted by one or more R¹) | Ar^a (optionally substituted by one or more R¹) | m | n | o | p |
|---|---|---|---|---|---|---|---|
| (II-9-2) | " | " | " | 1 | 0 | 0 | 1 |
| (II-9-3) | " | " | " | 0 | 1 | 1 | 0 |
| (II-9-4) | " | " | " | 0 | 1 | 0 | 1 |
| (II-9-5) | " | " | Naphthyl | 1 | 0 | 1 | 0 |
| (II-9-6) | " | " | " | 1 | 0 | 0 | 1 |
| (II-9-7) | " | " | " | 0 | 1 | 1 | 0 |
| (II-9-8) | " | " | " | 0 | 1 | 0 | 1 |
| (II-9-9) | " | Naphthyl | Phenyl | 1 | 0 | 1 | 0 |
| (II-9-10) | " | " | " | 1 | 0 | 0 | 1 |
| (II-9-11) | " | " | " | 0 | 1 | 1 | 0 |
| (II-9-12) | " | " | " | 0 | 1 | 0 | 1 |
| (II-9-13) | " | " | Naphthyl | 1 | 0 | 1 | 0 |
| (II-9-14) | " | " | " | 1 | 0 | 0 | 1 |
| (II-9-15) | " | " | " | 0 | 1 | 1 | 0 |
| (II-9-16) | " | " | " | 0 | 1 | 0 | 1 |
| (II-9-17) | " | Fluorenyl | Phenyl | 1 | 0 | 1 | 0 |
| (II-9-18) | " | " | " | 1 | 0 | 0 | 1 |
| (II-9-19) | " | " | " | 0 | 1 | 1 | 0 |
| (II-9-20) | " | " | " | 0 | 1 | 0 | 1 |
| (II-9-21) | " | " | Naphthyl | 1 | 0 | 1 | 0 |
| (II-9-22) | " | " | " | 1 | 0 | 0 | 1 |
| (II-9-23) | " | " | " | 0 | 1 | 1 | 0 |
| (II-9-24) | " | " | " | 0 | 1 | 0 | 1 |
| (II-10-1) | Formula (II-10) | Phenyl | Phenyl | 1 | 0 | 1 | 0 |
| (II-10-2) | " | " | " | 1 | 0 | 0 | 1 |
| (II-10-3) | " | " | " | 0 | 1 | 1 | 0 |
| (II-10-4) | " | " | " | 0 | 1 | 0 | 1 |
| (II-10-5) | " | " | Naphthyl | 1 | 0 | 1 | 0 |
| (II-10-6) | " | " | " | 1 | 0 | 0 | 1 |
| (II-10-7) | " | " | " | 0 | 1 | 1 | 0 |
| (II-10-8) | " | " | " | 0 | 1 | 0 | 1 |
| (II-10-9) | " | Naphthyl | Phenyl | 1 | 0 | 1 | 0 |
| (II-10-10) | " | " | " | 1 | 0 | 0 | 1 |
| (II-10-11) | " | " | " | 0 | 1 | 1 | 0 |
| (II-10-12) | " | " | " | 0 | 1 | 0 | 1 |
| (II-10-13) | " | " | Naphthyl | 1 | 0 | 1 | 0 |
| (II-10-14) | " | " | " | 1 | 0 | 0 | 1 |
| (II-10-15) | " | " | " | 0 | 1 | 1 | 0 |
| (II-10-16) | " | " | " | 0 | 1 | 0 | 1 |
| (II-10-17) | " | Fluorenyl | Phenyl | 1 | 0 | 1 | 0 |
| (II-10-18) | " | " | " | 1 | 0 | 0 | 1 |
| (II-10-19) | " | " | " | 0 | 1 | 1 | 0 |
| (II-10-20) | " | " | " | 0 | 1 | 0 | 1 |
| (II-10-21) | " | " | Naphthyl | 1 | 0 | 1 | 0 |
| (II-10-22) | " | " | " | 1 | 0 | 0 | 1 |
| (II-10-23) | " | " | " | 0 | 1 | 1 | 0 |
| (II-10-24) | " | " | " | 0 | 1 | 0 | 1 |
| (II-10-25) | " | Dibenzofuranyl | Phenyl | 1 | 0 | 1 | 0 |
| (II-10-26) | " | " | " | 1 | 0 | 0 | 1 |
| (II-10-27) | " | " | " | 0 | 1 | 1 | 0 |
| (II-10-28) | " | " | " | 0 | 1 | 0 | 1 |
| (II-10-29) | " | " | Naphthyl | 1 | 0 | 1 | 0 |
| (II-10-30) | " | " | " | 1 | 0 | 0 | 1 |
| (II-10-31) | " | " | " | 0 | 1 | 1 | 0 |
| (II-10-32) | " | " | " | 0 | 1 | 0 | 1 |
| (II-10-33) | " | Dibenzothiophenyl | Phenyl | 1 | 0 | 1 | 0 |
| (II-10-34) | " | " | " | 1 | 0 | 0 | 1 |
| (II-10-35) | " | " | " | 0 | 1 | 1 | 0 |
| (II-10-36) | " | " | " | 0 | 1 | 0 | 1 |
| (II-10-37) | " | " | Naphthyl | 1 | 0 | 1 | 0 |
| (II-10-38) | " | " | " | 1 | 0 | 0 | 1 |
| (II-10-39) | " | " | " | 0 | 1 | 1 | 0 |
| (II-10-40) | " | " | " | 0 | 1 | 0 | 1 |
| (II-11-1) | Formula (II-11) | Phenyl | Phenyl | 1 | 0 | 1 | 0 |
| (II-11-2) | " | " | " | 1 | 0 | 0 | 1 |
| (II-11-3) | " | " | " | 0 | 1 | 1 | 0 |
| (II-11-4) | " | " | " | 0 | 1 | 0 | 1 |
| (II-11-5) | " | " | Naphthyl | 1 | 0 | 1 | 0 |
| (II-11-6) | " | " | " | 1 | 0 | 0 | 1 |
| (II-11-7) | " | " | " | 0 | 1 | 1 | 0 |
| (II-11-8) | " | " | " | 0 | 1 | 0 | 1 |
| (II-11-9) | " | Naphthyl | Phenyl | 1 | 0 | 1 | 0 |
| (II-11-10) | " | " | " | 1 | 0 | 0 | 1 |
| (II-11-11) | " | " | " | 0 | 1 | 1 | 0 |
| (II-11-12) | " | " | " | 0 | 1 | 0 | 1 |

-continued

| Formula | Parent structure | Ar¹ (optionally substituted by one or more R¹) | Ar^a (optionally substituted by one or more R¹) | m | n | o | p |
|---|---|---|---|---|---|---|---|
| (II-11-13) | " | " | Naphthyl | 1 | 0 | 1 | 0 |
| (II-11-14) | " | " | " | 1 | 0 | 0 | 1 |
| (II-11-15) | " | " | " | 0 | 1 | 1 | 0 |
| (II-11-16) | " | " | " | 0 | 1 | 0 | 1 |
| (II-11-17) | " | Fluorenyl | Phenyl | 1 | 0 | 1 | 0 |
| (II-11-18) | " | " | " | 1 | 0 | 0 | 1 |
| (II-11-19) | " | " | " | 0 | 1 | 1 | 0 |
| (II-11-20) | " | " | " | 0 | 1 | 0 | 1 |
| (II-11-21) | " | " | Naphthyl | 1 | 0 | 1 | 0 |
| (II-11-22) | " | " | " | 1 | 0 | 0 | 1 |
| (II-11-23) | " | " | " | 0 | 1 | 1 | 0 |
| (II-11-24) | " | " | " | 0 | 1 | 0 | 1 |
| (II-11-25) | " | Dibenzofuranyl | Phenyl | 1 | 0 | 1 | 0 |
| (II-11-26) | " | " | " | 1 | 0 | 0 | 1 |
| (II-11-27) | " | " | " | 0 | 1 | 1 | 0 |
| (II-11-28) | " | " | " | 0 | 1 | 0 | 1 |
| (II-11-29) | " | " | Naphthyl | 1 | 0 | 1 | 0 |
| (II-11-30) | " | " | " | 1 | 0 | 0 | 1 |
| (II-11-31) | " | " | " | 0 | 1 | 1 | 0 |
| (II-11-32) | " | " | " | 0 | 1 | 0 | 1 |
| (II-11-33) | " | Dibenzothiophenyl | Phenyl | 1 | 0 | 1 | 0 |
| (II-11-34) | " | " | " | 1 | 0 | 0 | 1 |
| (II-11-35) | " | " | " | 0 | 1 | 1 | 0 |
| (II-11-36) | " | " | " | 0 | 1 | 0 | 1 |
| (II-11-37) | " | " | Naphthyl | 1 | 0 | 1 | 0 |
| (II-11-38) | " | " | " | 1 | 0 | 0 | 1 |
| (II-11-39) | " | " | " | 0 | 1 | 1 | 0 |
| (II-11-40) | " | " | " | 0 | 1 | 0 | 1 |
| (II-12-1) | Formula (II-12) | Phenyl | Phenyl | 1 | 0 | 1 | 0 |
| (II-12-2) | " | " | " | 1 | 0 | 0 | 1 |
| (II-12-3) | " | " | " | 0 | 1 | 1 | 0 |
| (II-12-4) | " | " | " | 0 | 1 | 0 | 1 |
| (II-12-5) | " | " | Naphthyl | 1 | 0 | 1 | 0 |
| (II-12-6) | " | " | " | 1 | 0 | 0 | 1 |
| (II-12-7) | " | " | " | 0 | 1 | 1 | 0 |
| (II-12-8) | " | " | " | 0 | 1 | 0 | 1 |
| (II-12-9) | " | Naphthyl | Phenyl | 1 | 0 | 1 | 0 |
| (II-12-10) | " | " | " | 1 | 0 | 0 | 1 |
| (II-12-11) | " | " | " | 0 | 1 | 1 | 0 |
| (II-12-12) | " | " | " | 0 | 1 | 0 | 1 |
| (II-12-13) | " | " | Naphthyl | 1 | 0 | 1 | 0 |
| (II-12-14) | " | " | " | 1 | 0 | 0 | 1 |
| (II-12-15) | " | " | " | 0 | 1 | 1 | 0 |
| (II-12-16) | " | " | " | 0 | 1 | 0 | 1 |
| (II-12-17) | " | Fluorenyl | Phenyl | 1 | 0 | 1 | 0 |
| (II-12-18) | " | " | " | 1 | 0 | 0 | 1 |
| (II-12-19) | " | " | " | 0 | 1 | 1 | 0 |
| (II-12-20) | " | " | " | 0 | 1 | 0 | 1 |
| (II-12-21) | " | " | Naphthyl | 1 | 0 | 1 | 0 |
| (II-12-22) | " | " | " | 1 | 0 | 0 | 1 |
| (II-12-23) | " | " | " | 0 | 1 | 1 | 0 |
| (II-12-24) | " | " | " | 0 | 1 | 0 | 1 |
| (II-12-25) | " | Dibenzofuranyl | Phenyl | 1 | 0 | 1 | 0 |
| (II-12-26) | " | " | " | 1 | 0 | 0 | 1 |
| (II-12-27) | " | " | " | 0 | 1 | 1 | 0 |
| (II-12-28) | " | " | " | 0 | 1 | 0 | 1 |
| (II-12-29) | " | " | Naphthyl | 1 | 0 | 1 | 0 |
| (II-12-30) | " | " | " | 1 | 0 | 0 | 1 |
| (II-12-31) | " | " | " | 0 | 1 | 1 | 0 |
| (II-12-32) | " | " | " | 0 | 1 | 0 | 1 |
| (II-12-33) | " | Dibenzothiophenyl | Phenyl | 1 | 0 | 1 | 0 |
| (II-12-34) | " | " | " | 1 | 0 | 0 | 1 |
| (II-12-35) | " | " | " | 0 | 1 | 1 | 0 |
| (II-12-36) | " | " | " | 0 | 1 | 0 | 1 |
| (II-12-37) | " | " | Naphthyl | 1 | 0 | 1 | 0 |
| (II-12-38) | " | " | " | 1 | 0 | 0 | 1 |
| (II-12-39) | " | " | " | 0 | 1 | 1 | 0 |
| (II-12-40) | " | " | " | 0 | 1 | 0 | 1 |

Compounds of the formula (III) particularly preferably conform to the following formulae:

| Formula | Parent structure | Ar¹ (optionally substituted by one or more R¹) | m | n | o | p | q | r |
|---|---|---|---|---|---|---|---|---|
| (III-1-1) | Formula (III-1) | Phenyl | 1 | 0 | 1 | 0 | 1 | 0 |
| (III-1-2) | " | " | 1 | 0 | 0 | 1 | 1 | 0 |
| (III-1-3) | " | " | 0 | 1 | 1 | 0 | 1 | 0 |
| (III-1-4) | " | " | 0 | 1 | 0 | 1 | 1 | 0 |
| (III-1-5) | " | " | 1 | 0 | 1 | 0 | 0 | 1 |
| (III-1-6) | " | " | 1 | 0 | 0 | 1 | 0 | 1 |
| (III-1-7) | " | " | 0 | 1 | 1 | 0 | 0 | 1 |
| (III-1-8) | " | " | 0 | 1 | 0 | 1 | 0 | 1 |
| (III-1-9) | " | Naphthyl | 1 | 0 | 1 | 0 | 1 | 0 |
| (III-1-10) | " | " | 1 | 0 | 0 | 1 | 1 | 0 |
| (III-1-11) | " | " | 0 | 1 | 1 | 0 | 1 | 0 |
| (III-1-12) | " | " | 0 | 1 | 0 | 1 | 1 | 0 |
| (III-1-13) | " | " | 1 | 0 | 1 | 0 | 0 | 1 |
| (III-1-14) | " | " | 1 | 0 | 0 | 1 | 0 | 1 |
| (III-1-15) | " | " | 0 | 1 | 1 | 0 | 0 | 1 |
| (III-1-16) | " | " | 0 | 1 | 0 | 1 | 0 | 1 |
| (III-1-17) | " | Fluorenyl | 1 | 0 | 1 | 0 | 1 | 0 |
| (III-1-18) | " | " | 1 | 0 | 0 | 1 | 1 | 0 |
| (III-1-19) | " | " | 0 | 1 | 1 | 0 | 1 | 0 |
| (III-1-20) | " | " | 0 | 1 | 0 | 1 | 1 | 0 |
| (III-1-21) | " | " | 1 | 0 | 1 | 0 | 0 | 1 |
| (III-1-22) | " | " | 1 | 0 | 0 | 1 | 0 | 1 |
| (III-1-23) | " | " | 0 | 1 | 1 | 0 | 0 | 1 |
| (III-1-24) | " | " | 0 | 1 | 0 | 1 | 0 | 1 |
| (III-1-25) | " | Dibenzofuranyl | 1 | 0 | 1 | 0 | 1 | 0 |
| (III-1-26) | " | " | 1 | 0 | 0 | 1 | 1 | 0 |
| (III-1-27) | " | " | 0 | 1 | 1 | 0 | 1 | 0 |
| (III-1-28) | " | " | 0 | 1 | 0 | 1 | 1 | 0 |
| (III-1-29) | " | " | 1 | 0 | 1 | 0 | 0 | 1 |
| (III-1-30) | " | " | 1 | 0 | 0 | 1 | 0 | 1 |
| (III-1-31) | " | " | 0 | 1 | 1 | 0 | 0 | 1 |
| (III-1-32) | " | " | 0 | 1 | 0 | 1 | 0 | 1 |
| (III-1-33) | " | Dibenzothiophenyl | 1 | 0 | 1 | 0 | 1 | 0 |
| (III-1-34) | " | " | 1 | 0 | 0 | 1 | 1 | 0 |
| (III-1-35) | " | " | 0 | 1 | 1 | 0 | 1 | 0 |
| (III-1-36) | " | " | 0 | 1 | 0 | 1 | 1 | 0 |
| (III-1-37) | " | " | 1 | 0 | 1 | 0 | 0 | 1 |
| (III-1-38) | " | " | 1 | 0 | 0 | 1 | 0 | 1 |
| (III-1-39) | " | " | 0 | 1 | 1 | 0 | 0 | 1 |
| (III-1-40) | " | " | 0 | 1 | 0 | 1 | 0 | 1 |
| (III-2-1) | Formula (III-2) | Phenyl | 1 | 0 | 1 | 0 | 1 | 0 |
| (III-2-2) | " | " | 1 | 0 | 0 | 1 | 1 | 0 |
| (III-2-3) | " | " | 0 | 1 | 1 | 0 | 1 | 0 |
| (III-2-4) | " | " | 0 | 1 | 0 | 1 | 1 | 0 |
| (III-2-5) | " | " | 1 | 0 | 1 | 0 | 0 | 1 |
| (III-2-6) | " | " | 1 | 0 | 0 | 1 | 0 | 1 |
| (III-2-7) | " | " | 0 | 1 | 1 | 0 | 0 | 1 |
| (III-2-8) | " | " | 0 | 1 | 0 | 1 | 0 | 1 |
| (III-2-9) | " | Naphthyl | 1 | 0 | 1 | 0 | 1 | 0 |
| (III-2-10) | " | " | 1 | 0 | 0 | 1 | 1 | 0 |
| (III-2-11) | " | " | 0 | 1 | 1 | 0 | 1 | 0 |
| (III-2-12) | " | " | 0 | 1 | 0 | 1 | 1 | 0 |
| (III-2-13) | " | " | 1 | 0 | 1 | 0 | 0 | 1 |
| (III-2-14) | " | " | 1 | 0 | 0 | 1 | 0 | 1 |
| (III-2-15) | " | " | 0 | 1 | 1 | 0 | 0 | 1 |
| (III-2-16) | " | " | 0 | 1 | 0 | 1 | 0 | 1 |
| (III-2-17) | " | Fluorenyl | 1 | 0 | 1 | 0 | 1 | 0 |
| (III-2-18) | " | " | 1 | 0 | 0 | 1 | 1 | 0 |
| (III-2-19) | " | " | 0 | 1 | 1 | 0 | 1 | 0 |
| (III-2-20) | " | " | 0 | 1 | 0 | 1 | 1 | 0 |
| (III-2-21) | " | " | 1 | 0 | 1 | 0 | 0 | 1 |
| (III-2-22) | " | " | 1 | 0 | 0 | 1 | 0 | 1 |
| (III-2-23) | " | " | 0 | 1 | 1 | 0 | 0 | 1 |
| (III-2-24) | " | " | 0 | 1 | 0 | 1 | 0 | 1 |
| (III-2-25) | " | Dibenzofuranyl | 1 | 0 | 1 | 0 | 1 | 0 |
| (III-2-26) | " | " | 1 | 0 | 0 | 1 | 1 | 0 |
| (III-2-27) | " | " | 0 | 1 | 1 | 0 | 1 | 0 |
| (III-2-28) | " | " | 0 | 1 | 0 | 1 | 1 | 0 |
| (III-2-29) | " | " | 1 | 0 | 1 | 0 | 0 | 1 |
| (III-2-30) | " | " | 1 | 0 | 0 | 1 | 0 | 1 |
| (III-2-31) | " | " | 0 | 1 | 1 | 0 | 0 | 1 |
| (III-2-32) | " | " | 0 | 1 | 0 | 1 | 0 | 1 |
| (III-2-33) | " | Dibenzothiophenyl | 1 | 0 | 1 | 0 | 1 | 0 |
| (III-2-34) | " | " | 1 | 0 | 0 | 1 | 1 | 0 |

-continued

| Formula | Parent structure | Ar¹ (optionally substituted by one or more R¹) | m | n | o | p | q | r |
|---|---|---|---|---|---|---|---|---|
| (III-2-35) | " | " | 0 | 1 | 1 | 0 | 1 | 0 |
| (III-2-36) | " | " | 0 | 1 | 0 | 1 | 1 | 0 |
| (III-2-37) | " | " | 1 | 0 | 1 | 0 | 0 | 1 |
| (III-2-38) | " | " | 1 | 0 | 0 | 1 | 0 | 1 |
| (III-2-39) | " | " | 0 | 1 | 1 | 0 | 0 | 1 |
| (III-2-40) | " | " | 0 | 1 | 0 | 1 | 0 | 1 |
| (III-3-1) | Formula (III-3) | Phenyl | 1 | 0 | 1 | 0 | 1 | 0 |
| (III-3-2) | " | " | 1 | 0 | 0 | 1 | 1 | 0 |
| (III-3-3) | " | " | 0 | 1 | 1 | 0 | 1 | 0 |
| (III-3-4) | " | " | 0 | 1 | 0 | 1 | 1 | 0 |
| (III-3-5) | " | " | 1 | 0 | 1 | 0 | 0 | 1 |
| (III-3-6) | " | " | 1 | 0 | 0 | 1 | 0 | 1 |
| (III-3-7) | " | " | 0 | 1 | 1 | 0 | 0 | 1 |
| (III-3-8) | " | " | 0 | 1 | 0 | 1 | 0 | 1 |
| (III-3-9) | " | Naphthyl | 1 | 0 | 1 | 0 | 1 | 0 |
| (III-3-10) | " | " | 1 | 0 | 0 | 1 | 1 | 0 |
| (III-3-11) | " | " | 0 | 1 | 1 | 0 | 1 | 0 |
| (III-3-12) | " | " | 0 | 1 | 0 | 1 | 1 | 0 |
| (III-3-13) | " | " | 1 | 0 | 1 | 0 | 0 | 1 |
| (III-3-14) | " | " | 1 | 0 | 0 | 1 | 0 | 1 |
| (III-3-15) | " | " | 0 | 1 | 1 | 0 | 0 | 1 |
| (III-3-16) | " | " | 0 | 1 | 0 | 1 | 0 | 1 |
| (III-3-17) | " | Fluorenyl | 1 | 0 | 1 | 0 | 1 | 0 |
| (III-3-18) | " | " | 1 | 0 | 0 | 1 | 1 | 0 |
| (III-3-19) | " | " | 0 | 1 | 1 | 0 | 1 | 0 |
| (III-3-20) | " | " | 0 | 1 | 0 | 1 | 1 | 0 |
| (III-3-21) | " | " | 1 | 0 | 1 | 0 | 0 | 1 |
| (III-3-22) | " | " | 1 | 0 | 0 | 1 | 0 | 1 |
| (III-3-23) | " | " | 0 | 1 | 1 | 0 | 0 | 1 |
| (III-3-24) | " | " | 0 | 1 | 0 | 1 | 0 | 1 |
| (III-3-25) | " | Dibenzofuranyl | 1 | 0 | 1 | 0 | 1 | 0 |
| (III-3-26) | " | " | 1 | 0 | 0 | 1 | 1 | 0 |
| (III-3-27) | " | " | 0 | 1 | 1 | 0 | 1 | 0 |
| (III-3-28) | " | " | 0 | 1 | 0 | 1 | 1 | 0 |
| (III-3-29) | " | " | 1 | 0 | 1 | 0 | 0 | 1 |
| (III-3-30) | " | " | 1 | 0 | 0 | 1 | 0 | 1 |
| (III-3-31) | " | " | 0 | 1 | 1 | 0 | 0 | 1 |
| (III-3-32) | " | " | 0 | 1 | 0 | 1 | 0 | 1 |
| (III-3-33) | " | Dibenzothiophenyl | 1 | 0 | 1 | 0 | 1 | 0 |
| (III-3-34) | " | " | 1 | 0 | 0 | 1 | 1 | 0 |
| (III-3-35) | " | " | 0 | 1 | 1 | 0 | 1 | 0 |
| (III-3-36) | " | " | 0 | 1 | 0 | 1 | 1 | 0 |
| (III-3-37) | " | " | 1 | 0 | 1 | 0 | 0 | 1 |
| (III-3-38) | " | " | 1 | 0 | 0 | 1 | 0 | 1 |
| (III-3-39) | " | " | 0 | 1 | 1 | 0 | 0 | 1 |
| (III-3-40) | " | " | 0 | 1 | 0 | 1 | 0 | 1 |
| (III-4-1) | Formula (III-4) | Phenyl | 1 | 0 | 1 | 0 | 1 | 0 |
| (III-4-2) | " | " | 1 | 0 | 0 | 1 | 1 | 0 |
| (III-4-3) | " | " | 0 | 1 | 1 | 0 | 1 | 0 |
| (III-4-4) | " | " | 0 | 1 | 0 | 1 | 1 | 0 |
| (III-4-5) | " | " | 1 | 0 | 1 | 0 | 0 | 1 |
| (III-4-6) | " | " | 1 | 0 | 0 | 1 | 0 | 1 |
| (III-4-7) | " | " | 0 | 1 | 1 | 0 | 0 | 1 |
| (III-4-8) | " | " | 0 | 1 | 0 | 1 | 0 | 1 |
| (III-4-9) | " | Naphthyl | 1 | 0 | 1 | 0 | 1 | 0 |
| (III-4-10) | " | " | 1 | 0 | 0 | 1 | 1 | 0 |
| (III-4-11) | " | " | 0 | 1 | 1 | 0 | 1 | 0 |
| (III-4-12) | " | " | 0 | 1 | 0 | 1 | 1 | 0 |
| (III-4-13) | " | " | 1 | 0 | 1 | 0 | 0 | 1 |
| (III-4-14) | " | " | 1 | 0 | 0 | 1 | 0 | 1 |
| (III-4-15) | " | " | 0 | 1 | 1 | 0 | 0 | 1 |
| (III-4-16) | " | " | 0 | 1 | 0 | 1 | 0 | 1 |
| (III-4-17) | " | Fluorenyl | 1 | 0 | 1 | 0 | 1 | 0 |
| (III-4-18) | " | " | 1 | 0 | 0 | 1 | 1 | 0 |
| (III-4-19) | " | " | 0 | 1 | 1 | 0 | 1 | 0 |
| (III-4-20) | " | " | 0 | 1 | 0 | 1 | 1 | 0 |
| (III-4-21) | " | " | 1 | 0 | 1 | 0 | 0 | 1 |
| (III-4-22) | " | " | 1 | 0 | 0 | 1 | 0 | 1 |
| (III-4-23) | " | " | 0 | 1 | 1 | 0 | 0 | 1 |
| (III-4-24) | " | " | 0 | 1 | 0 | 1 | 0 | 1 |
| (III-4-25) | " | Dibenzofuranyl | 1 | 0 | 1 | 0 | 1 | 0 |
| (III-4-26) | " | " | 1 | 0 | 0 | 1 | 1 | 0 |
| (III-4-27) | " | " | 0 | 1 | 1 | 0 | 1 | 0 |
| (III-4-28) | " | " | 0 | 1 | 0 | 1 | 1 | 0 |
| (III-4-29) | " | " | 1 | 0 | 1 | 0 | 0 | 1 |

-continued
| Formula | Parent structure | Ar¹ (optionally substituted by one or more R¹) | m | n | o | p | q | r |
|---|---|---|---|---|---|---|---|---|
| (III-4-30) | " | " | 1 | 0 | 0 | 1 | 0 | 1 |
| (III-4-31) | " | " | 0 | 1 | 1 | 0 | 0 | 1 |
| (III-4-32) | " | " | 0 | 1 | 0 | 1 | 0 | 1 |
| (III-4-33) | " | Dibenzothiophenyl | 1 | 0 | 1 | 0 | 1 | 0 |
| (III-4-34) | " | " | 1 | 0 | 0 | 1 | 1 | 0 |
| (III-4-35) | " | " | 0 | 1 | 1 | 0 | 1 | 0 |
| (III-4-36) | " | " | 0 | 1 | 0 | 1 | 1 | 0 |
| (III-4-37) | " | " | 1 | 0 | 1 | 0 | 0 | 1 |
| (III-4-38) | " | " | 1 | 0 | 0 | 1 | 0 | 1 |
| (III-4-39) | " | " | 0 | 1 | 1 | 0 | 0 | 1 |
| (III-4-40) | " | " | 0 | 1 | 0 | 1 | 0 | 1 |
Examples of compounds according to the invention are shown in the following table.
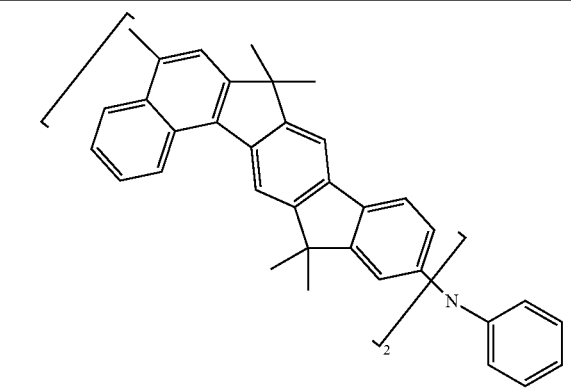
(1)
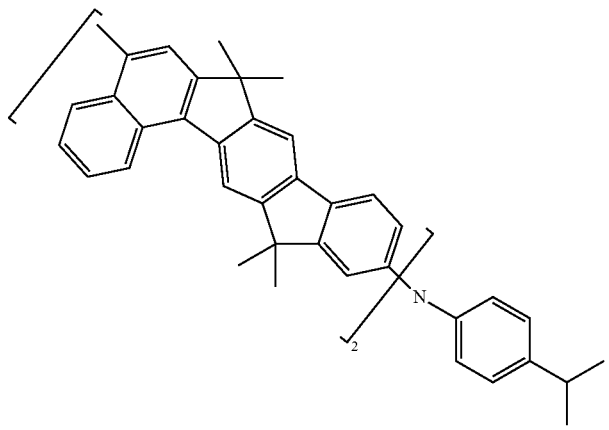
(2)
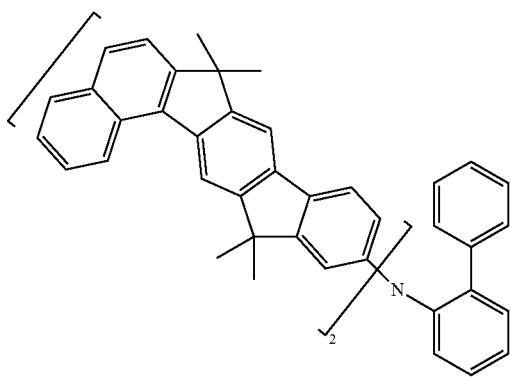
(3)

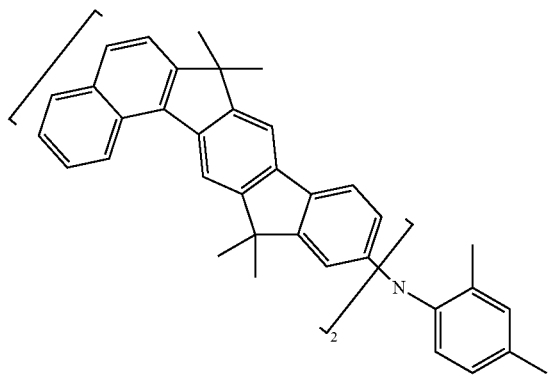
(4)
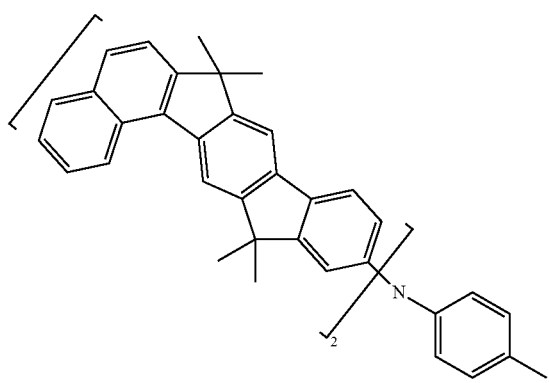
(5)
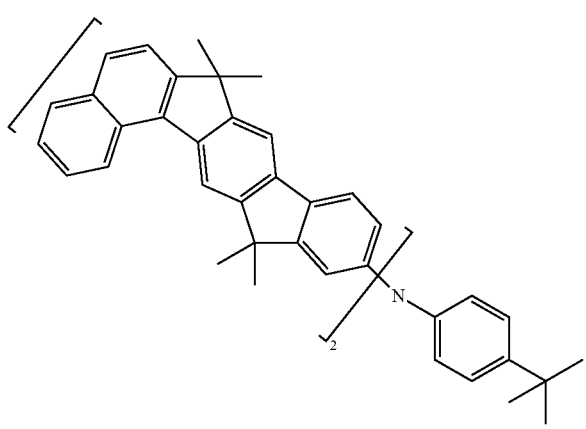
(6)
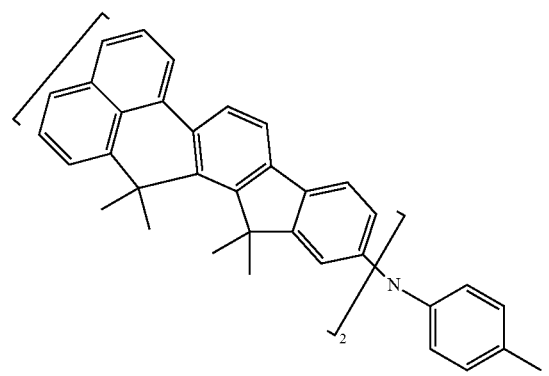
(7)

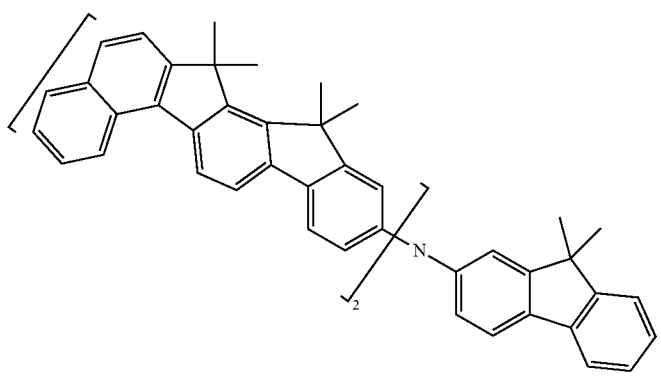
(8)
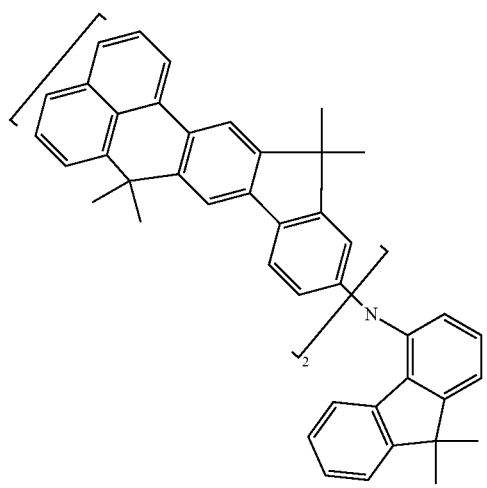
(9)
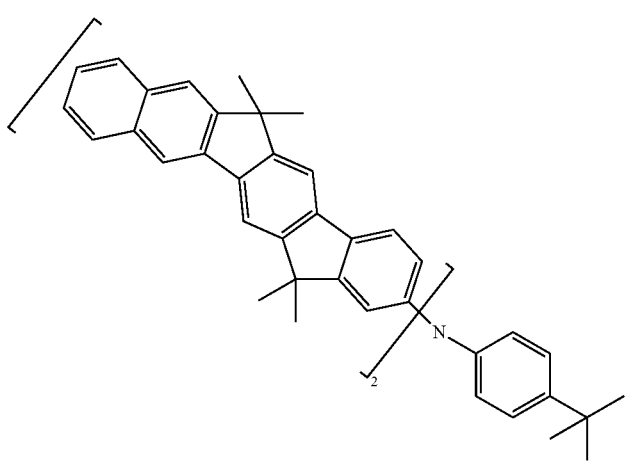
(10)

-continued
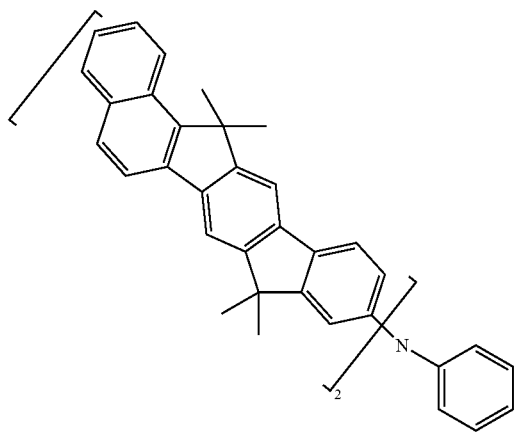
(11)
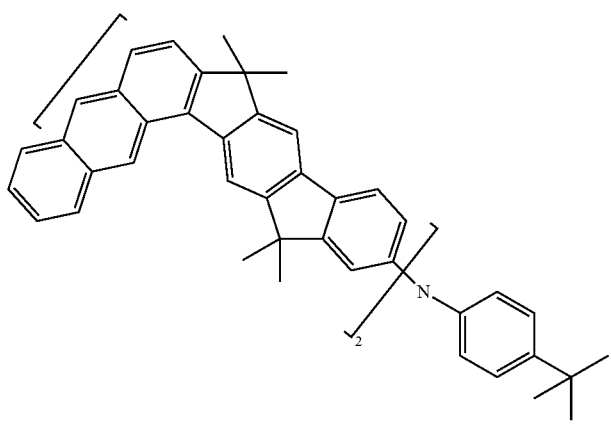
(12)
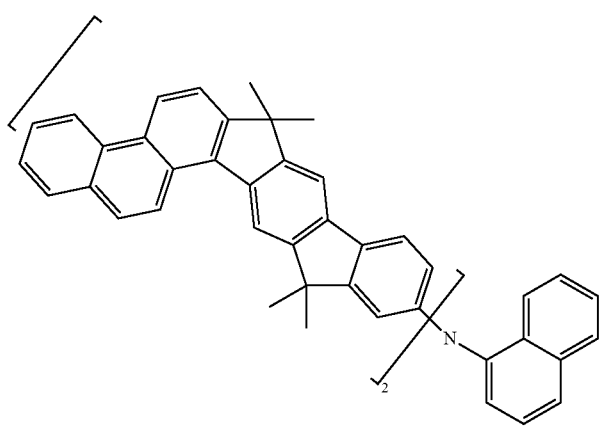
(13)

(14)
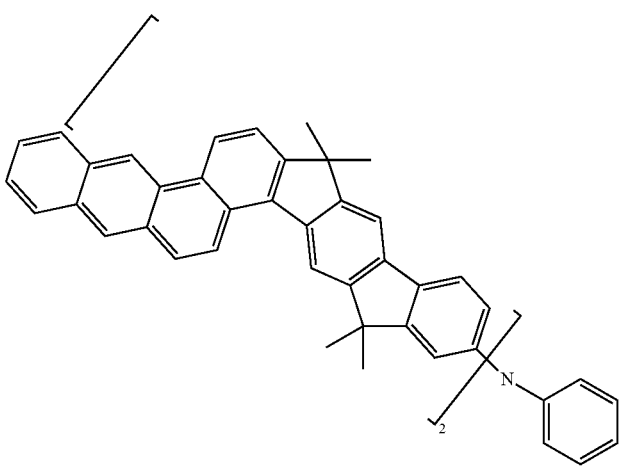
(15)
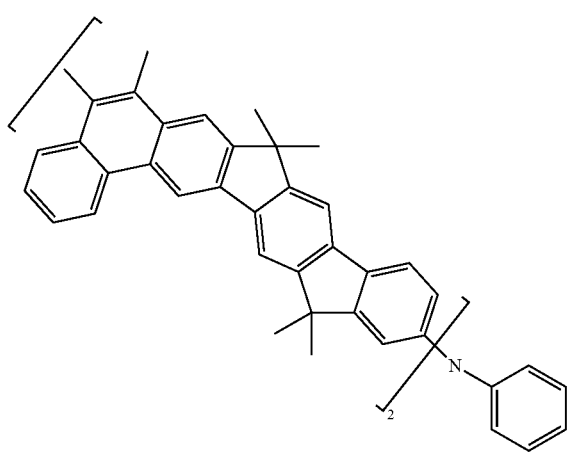
(16)
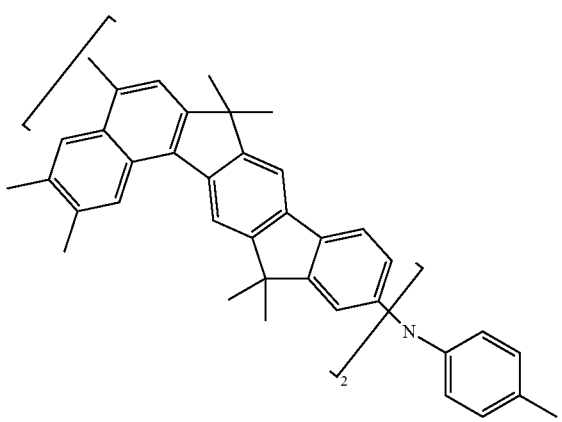

-continued
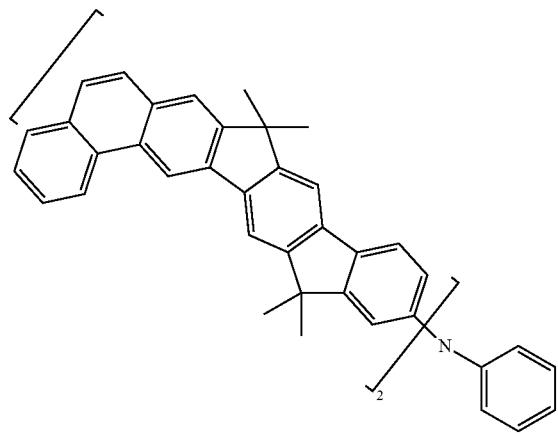
(17)
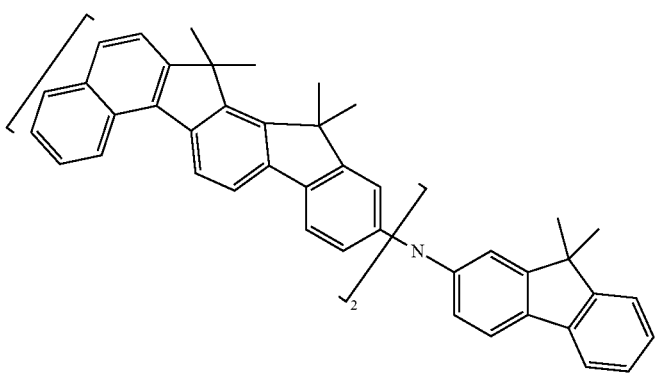
(18)
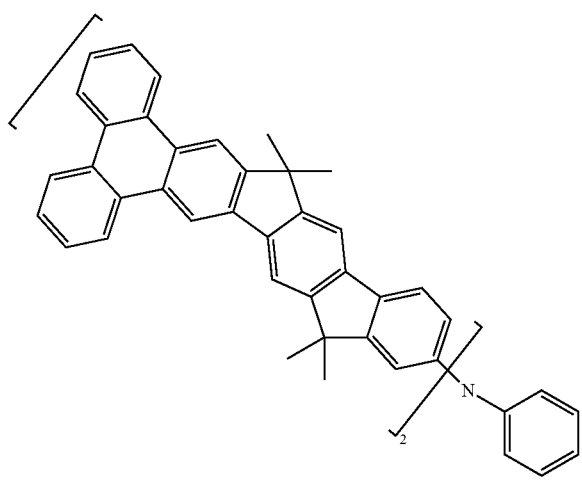
(19)
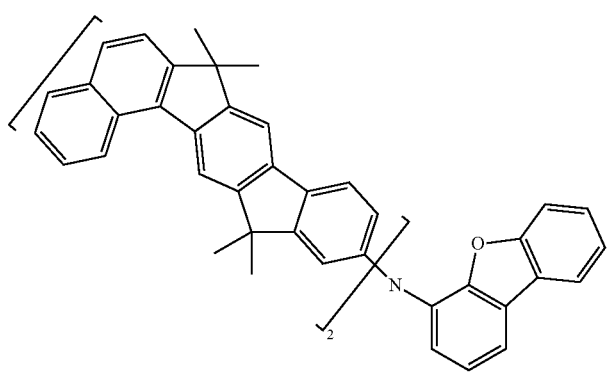
(20)

-continued
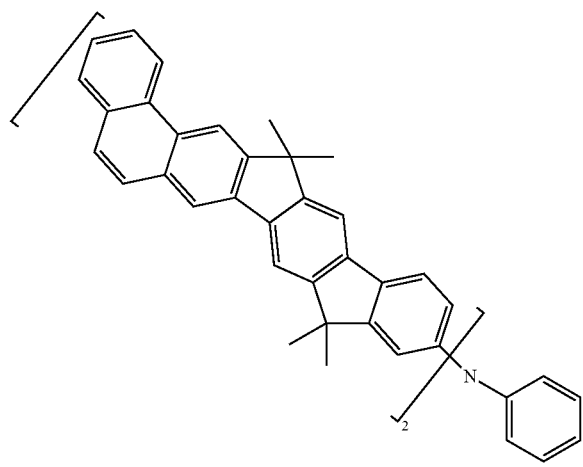
(21)
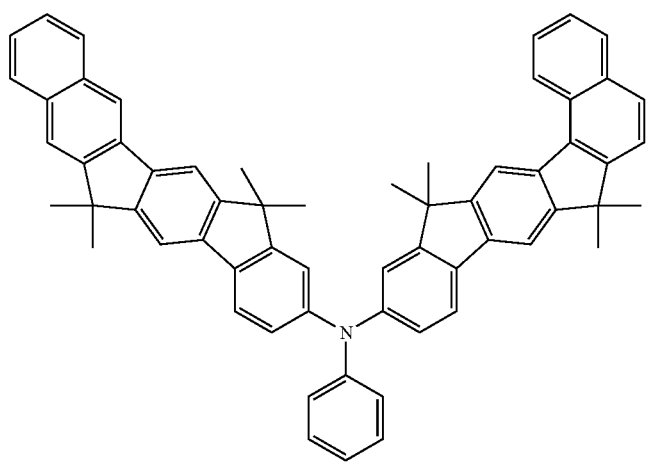 [SMILES: CC1(C)c2cc(N(c3ccccc3)c3ccc4c(c3)C(C)(C)c3cc5c(cc3-4)C(C)(C)c3ccc4ccccc4c3-5)ccc2-c2cc3c(cc21)-c1cc2ccccc2cc1C3(C)C]
(22)
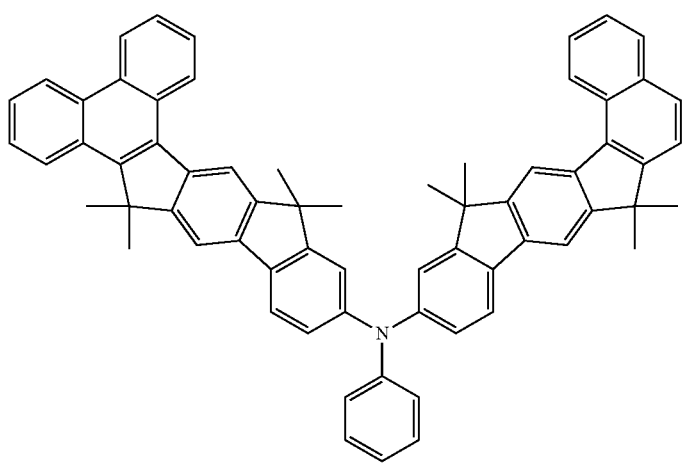 [SMILES: CC1(C)c2cc(N(c3ccccc3)c3ccc4c(c3)C(C)(C)c3cc5c(cc3-4)C(C)(C)c3c-5c4ccccc4c4ccccc34)ccc2-c2cc3c(cc21)-c1c(ccc2ccccc12)C3(C)C]
(23)

-continued
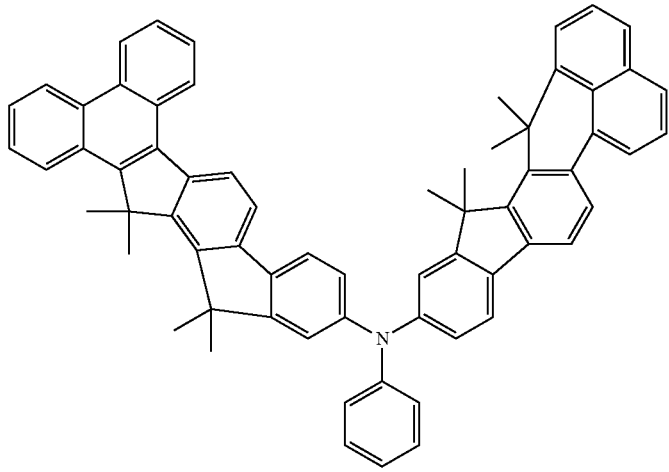 [SMILES: CC1(C)c2cc(N(c3ccccc3)c3ccc4c(c3)C(C)(C)c3c-4ccc4c3C(C)(C)c3cccc5cccc-4c35)ccc2-c2ccc3c(c21)C(C)(C)c1c-3c2ccccc2c2ccccc12]
(24)
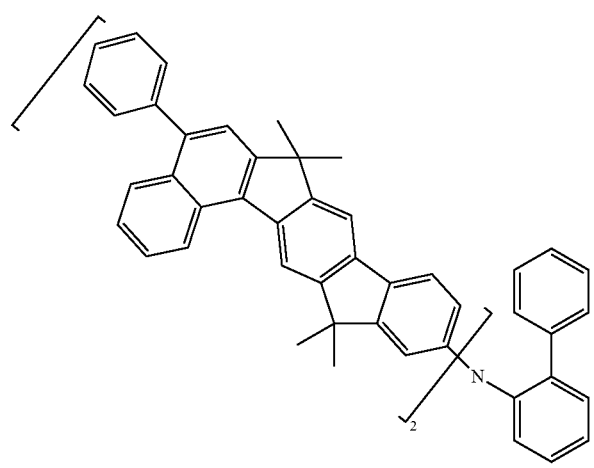
(25)
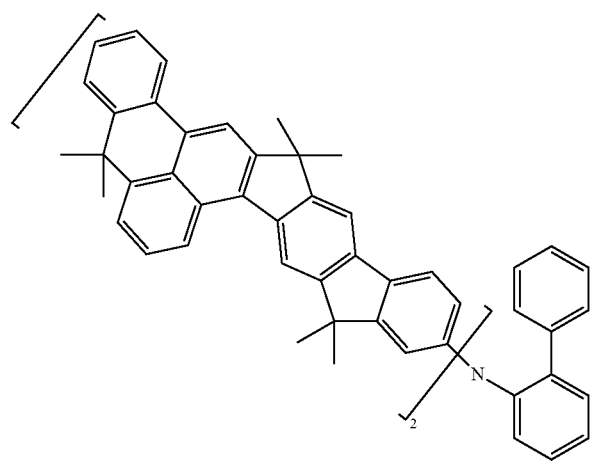
(26)

-continued
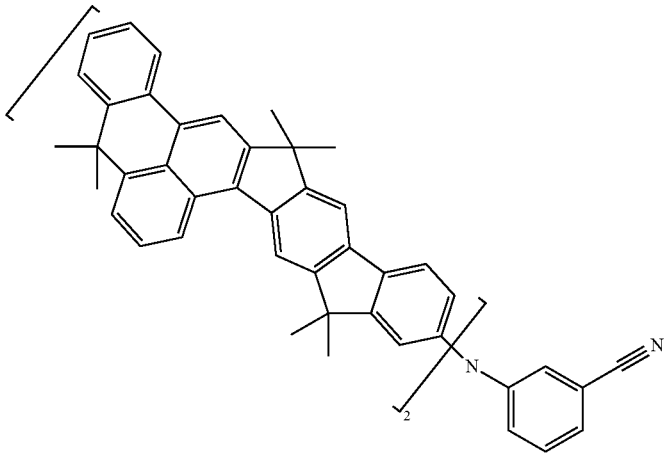
(27)
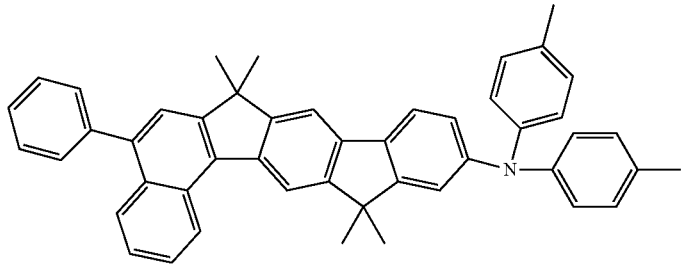 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
(28)
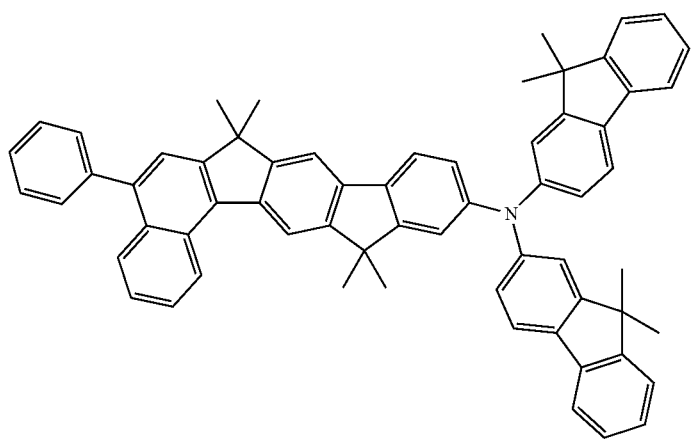 [SMILES: CC1(C)c2ccccc2-c2ccc(N(c3ccc4c(c3)C(C)(C)c3ccccc3-4)c3ccc4c(c3)C(C)(C)c3cc5c(cc3-4)C(C)(C)c3cc(-c4ccccc4)c4ccccc4c3-5)cc21]
(29)
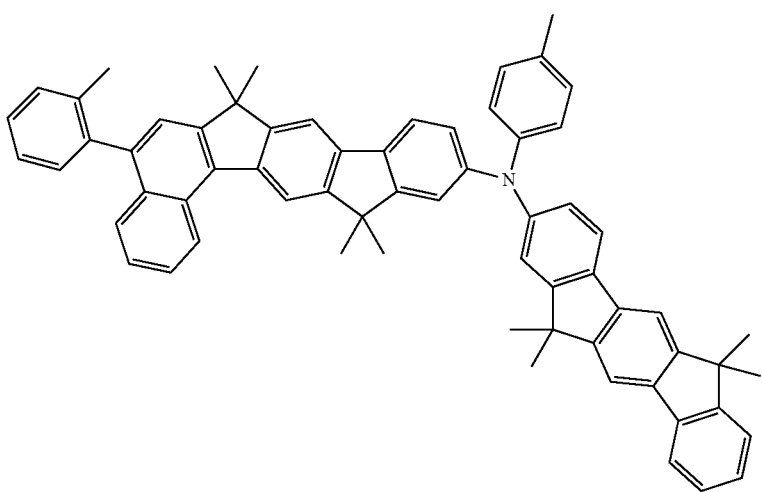 [SMILES: Cc1ccc(N(c2ccc3c(c2)C(C)(C)c2cc4c(cc2-3)C(C)(C)c2ccccc2-4)c2ccc3c(c2)C(C)(C)c2cc4c(cc2-3)C(C)(C)c2cc(-c3ccccc3C)c3ccccc3c2-4)cc1]
(30)

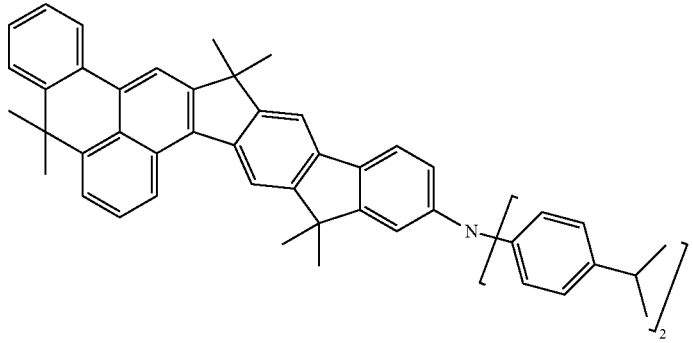
(31)
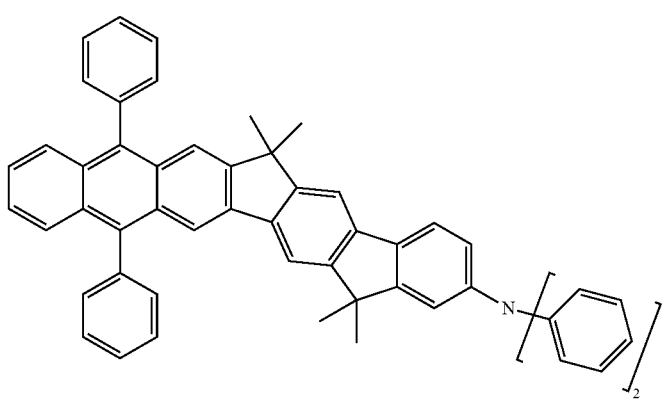
(32)
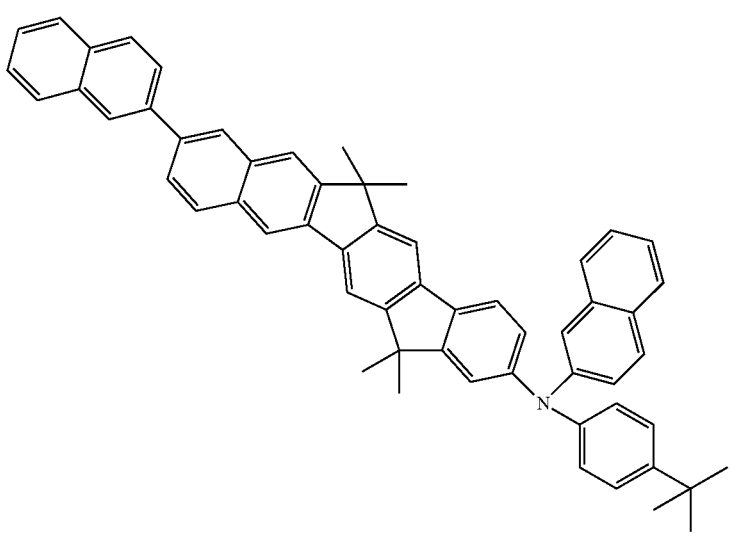 [SMILES: CC(C)(C)c1ccc(N(c2ccc3c(c2)C(C)(C)c2cc4c(cc2-3)C(C)(C)c2cc3cc(-c5ccc6ccccc6c5)ccc3cc2-4)c2ccc3ccccc3c2)cc1]
(33)
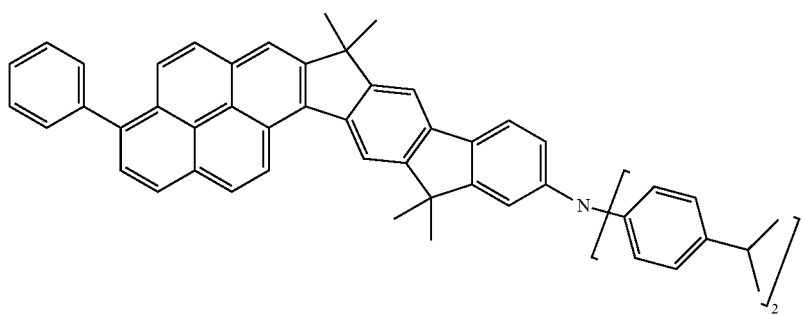
(34)

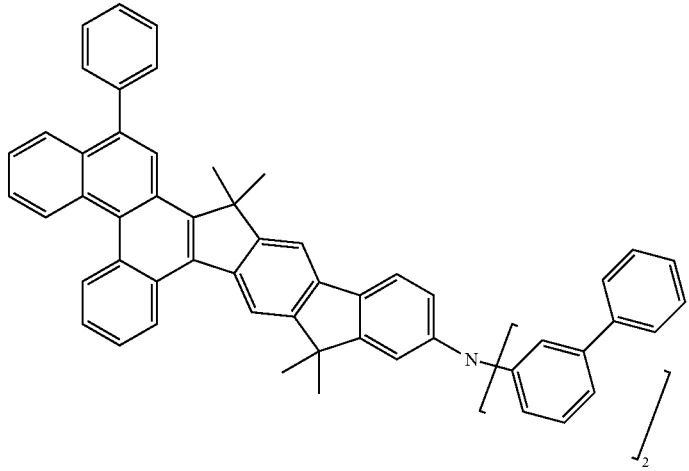
(35)
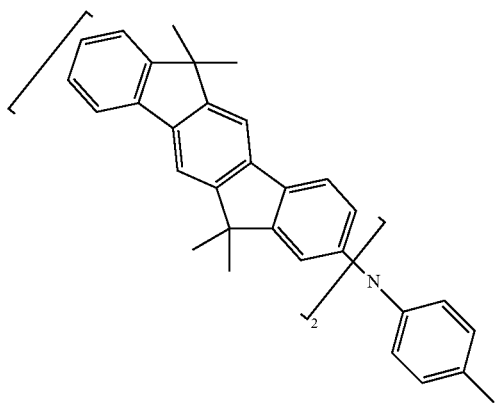
(36)
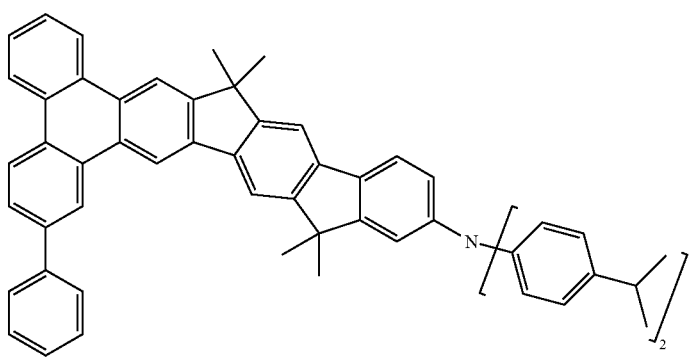
(37)

-continued
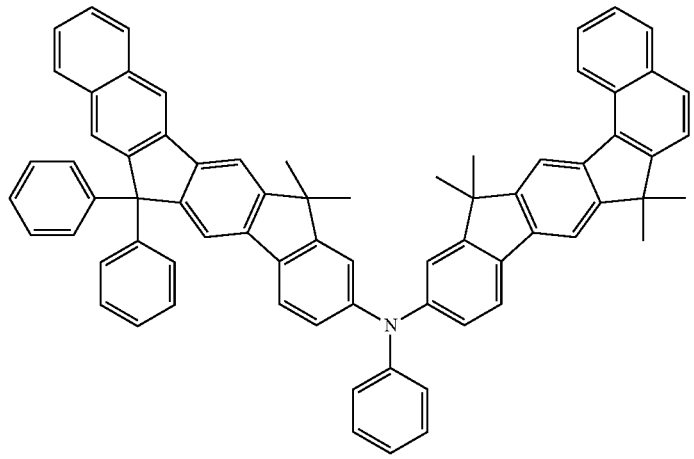 [SMILES: CC1(C)c2cc(N(c3ccccc3)c3ccc4c(c3)C(C)(C)c3cc5c(cc3-4)C(c3ccccc3)(c3ccccc3)c3cc4ccccc4cc3-5)ccc2-c2cc3c(cc21)-c1c(ccc2ccccc12)C3(C)C]
(38)
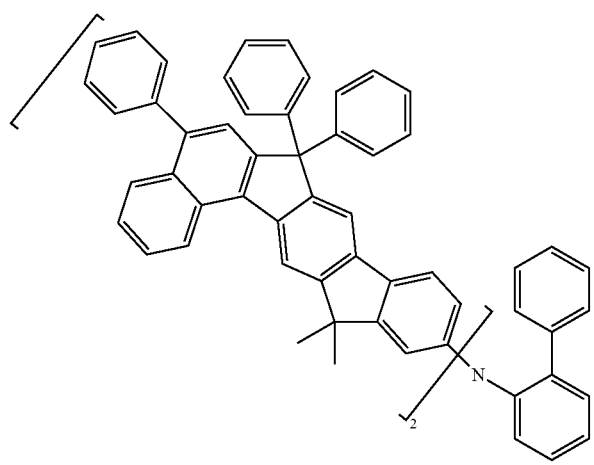
(39)
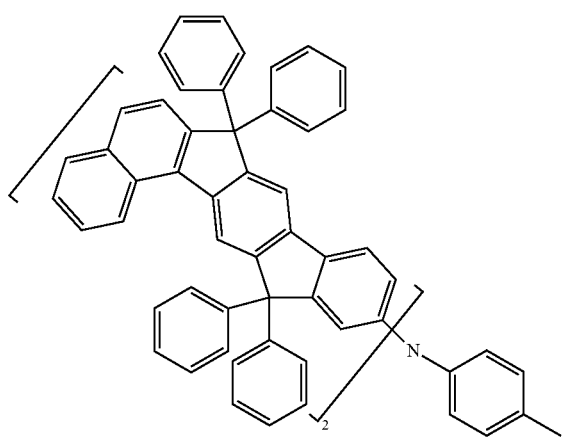
(40)

-continued
(41)
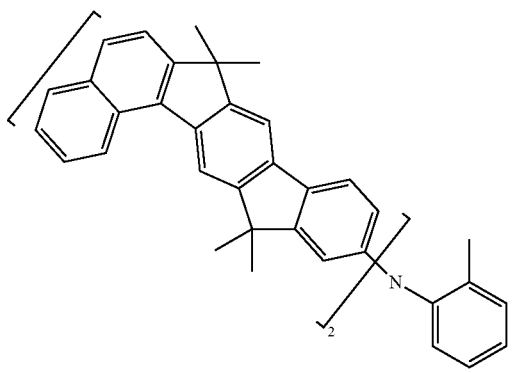
(42)
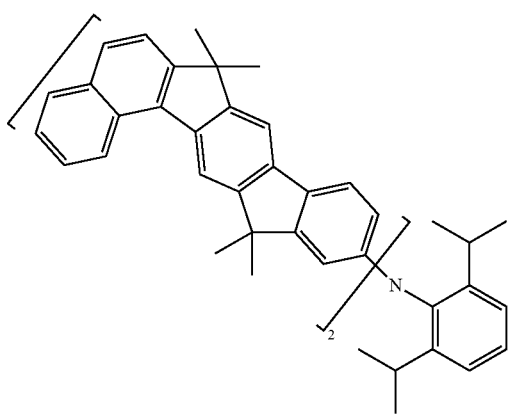
(43)
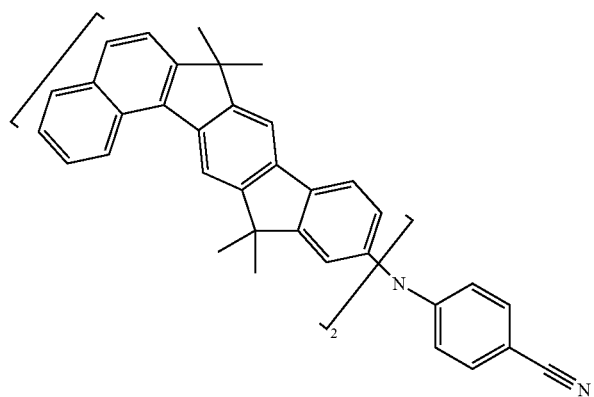
(44)
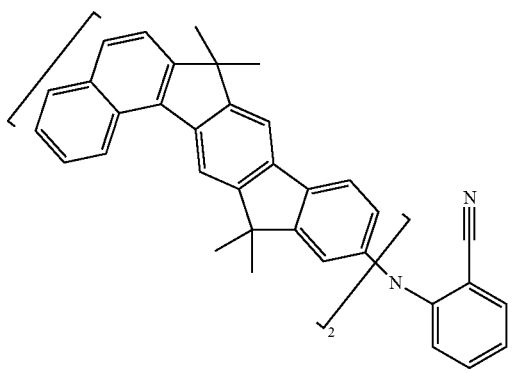

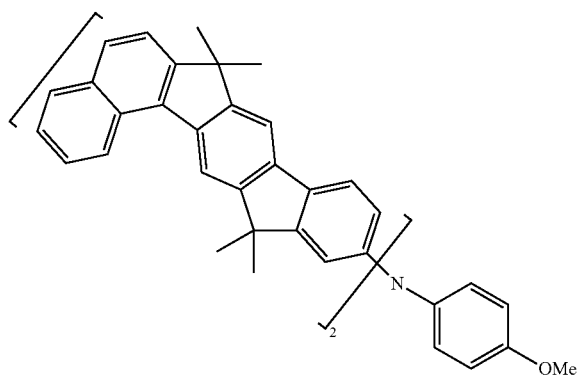
(45)
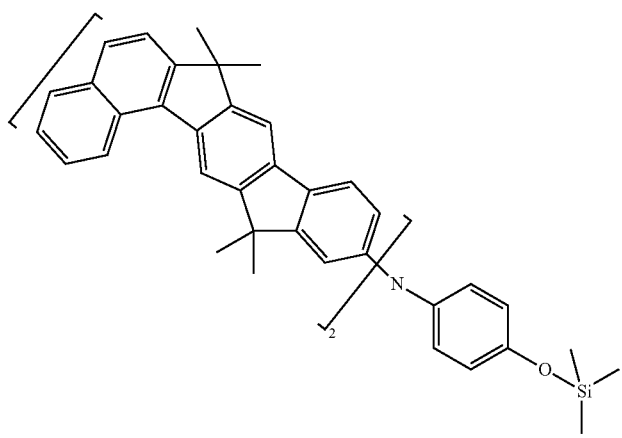
(46)
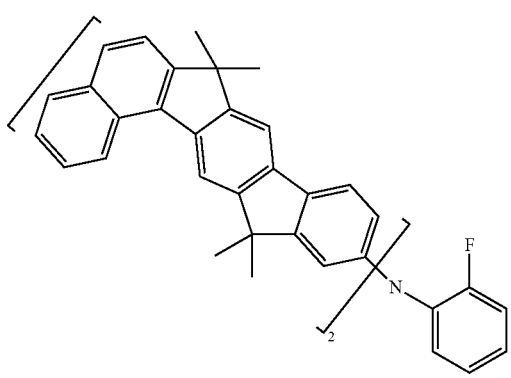
(47)
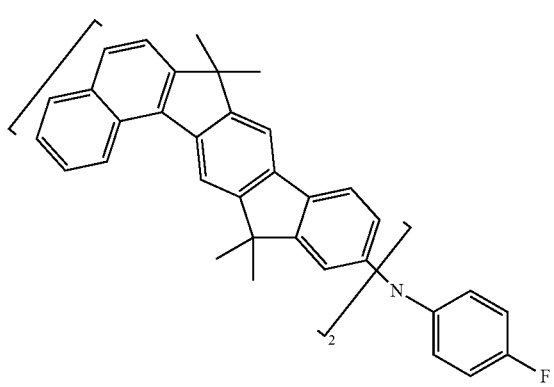
(48)

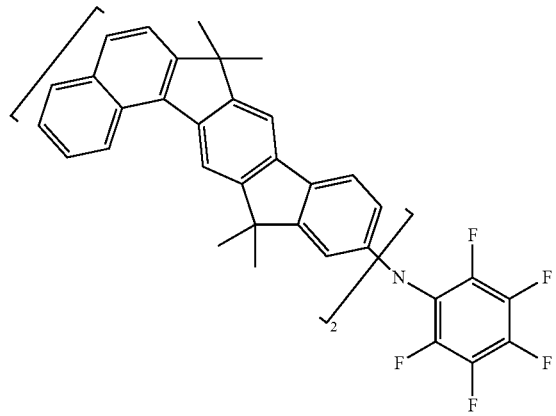
(49)
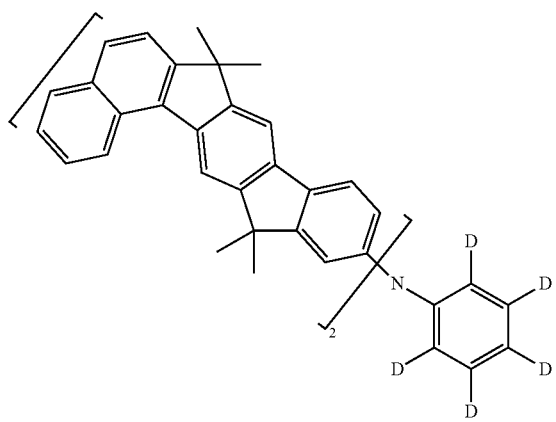
(50)
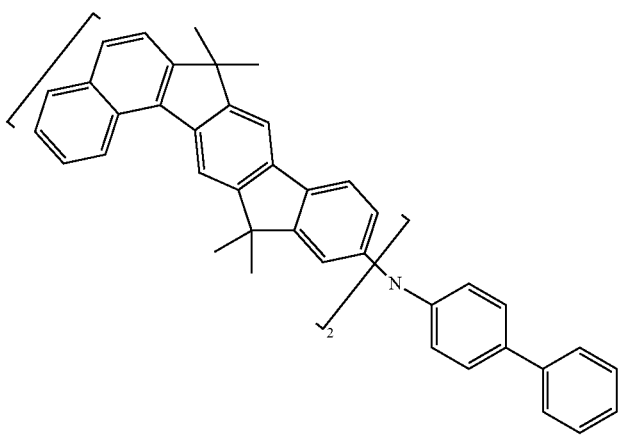
(51)
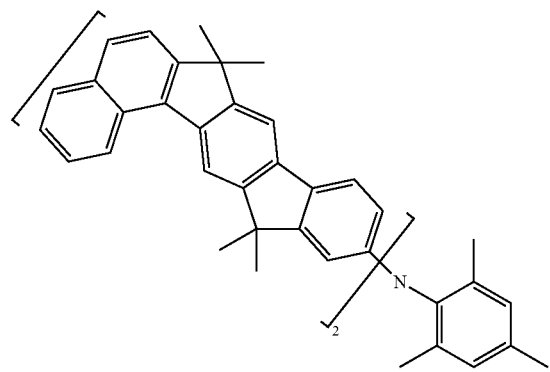
(52)

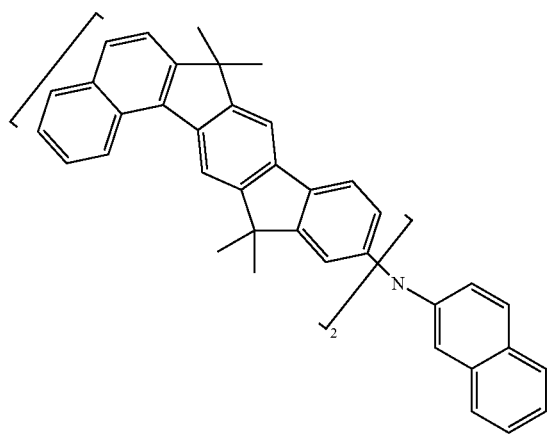
(53)
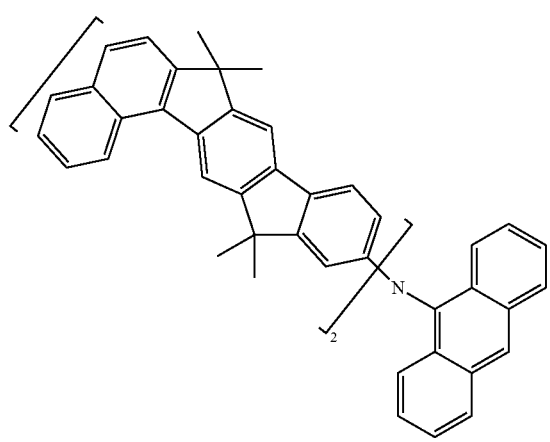
(54)
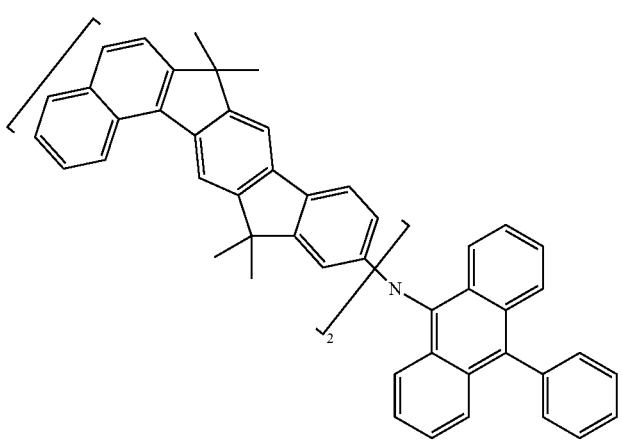
(55)

(56)
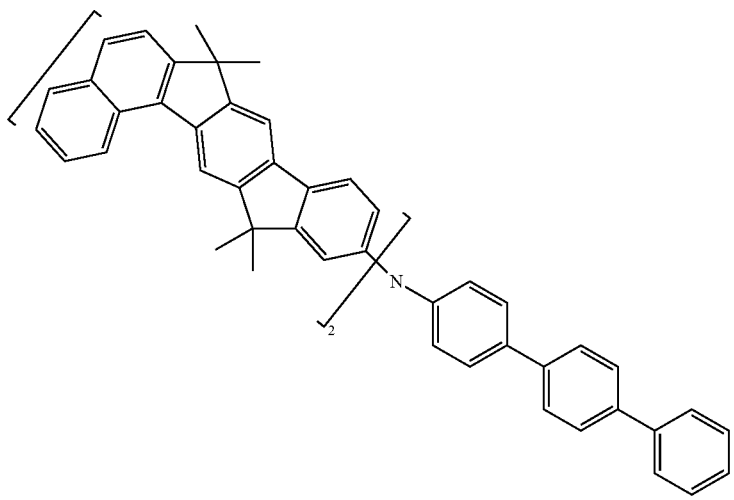
(57)
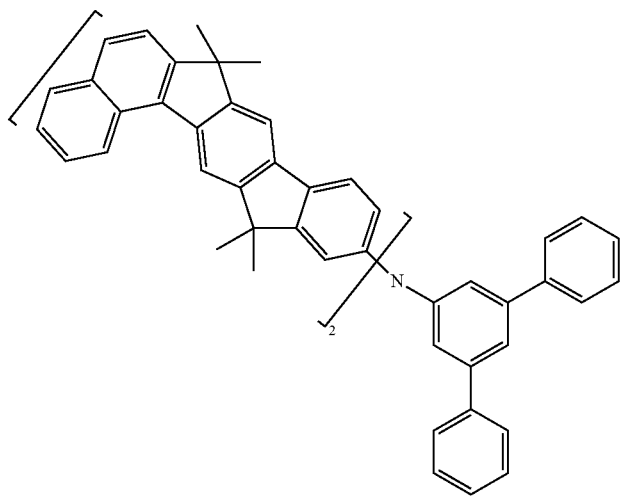
(58)
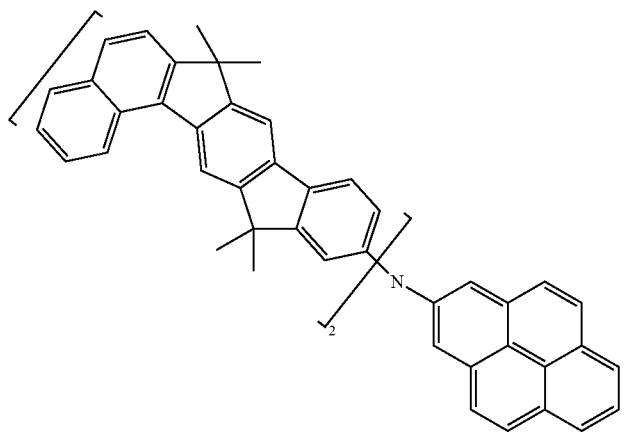

(59)
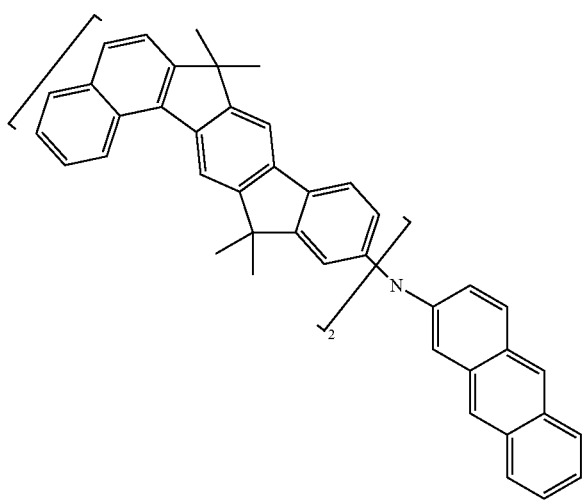
(60)
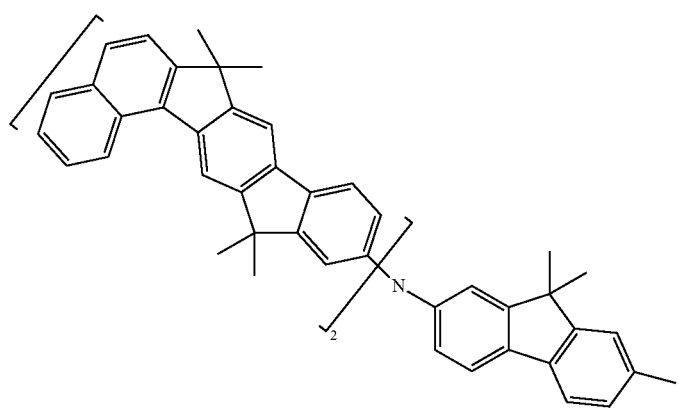
(61)
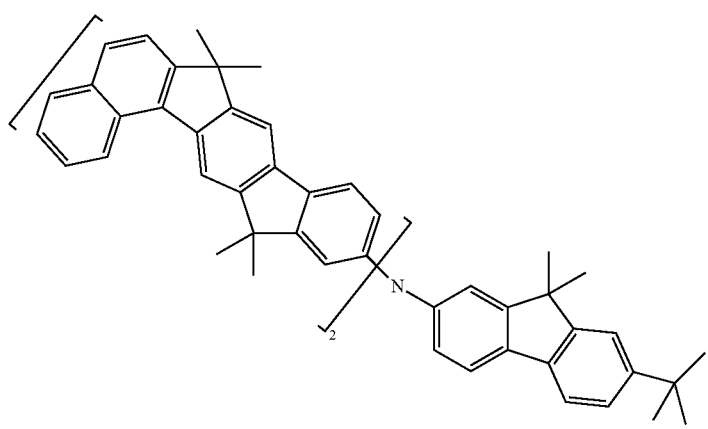

-continued
(62)
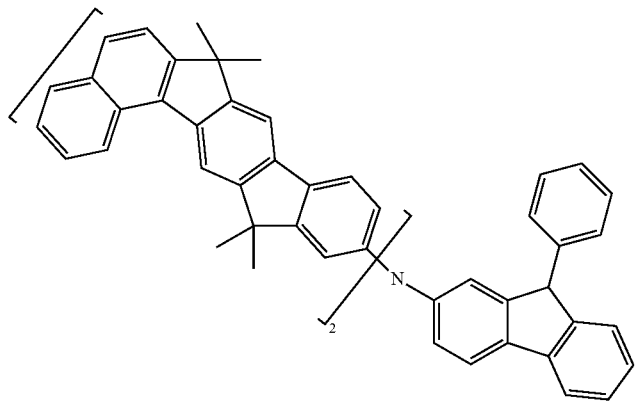
(63)
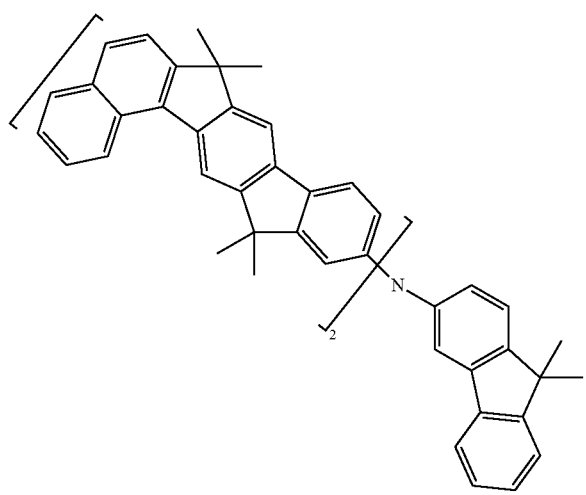
(64)
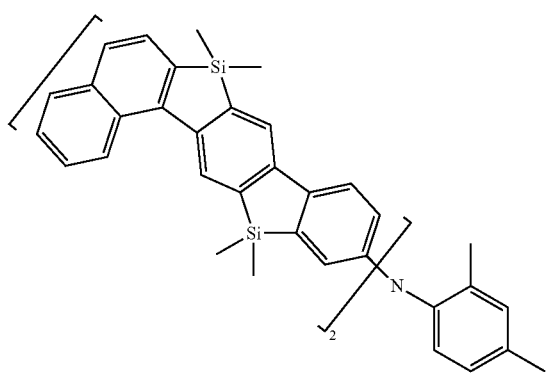
(65)
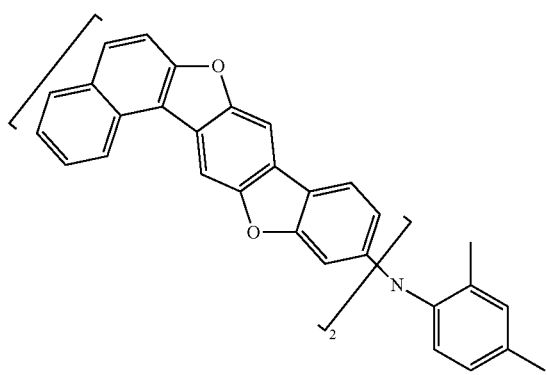

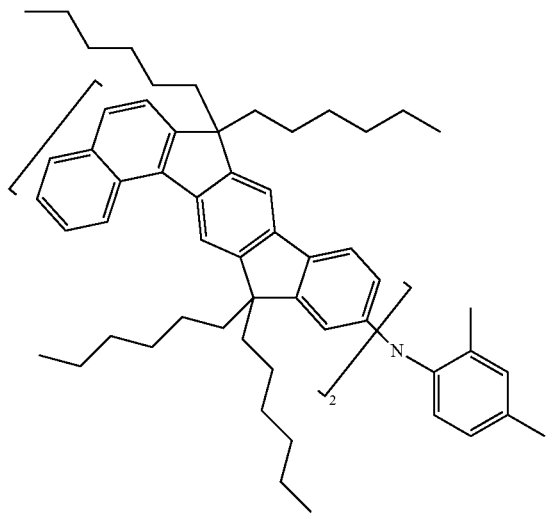
(66)
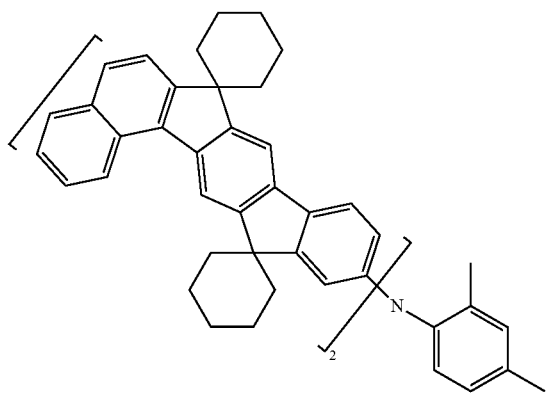
(67)
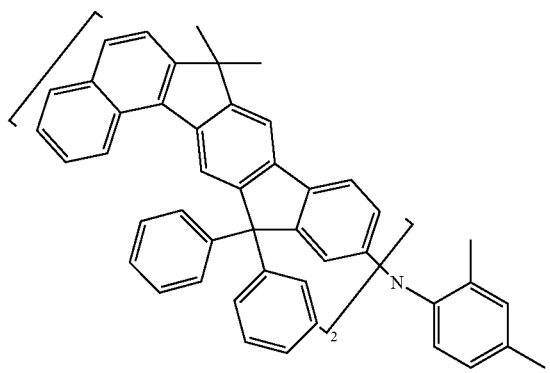
(68)

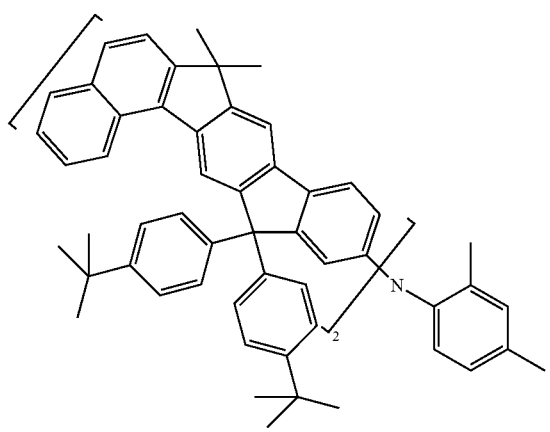
(69)
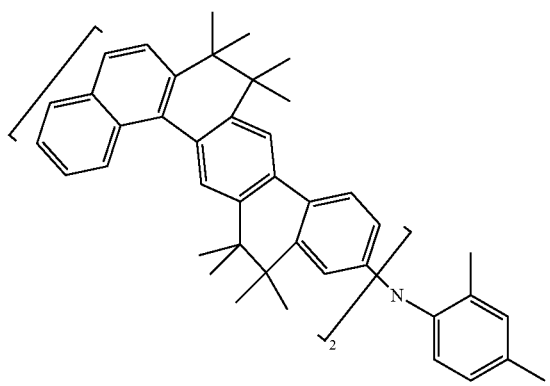
(70)
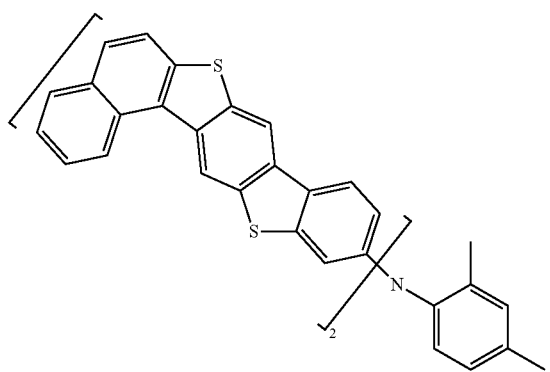
(71)
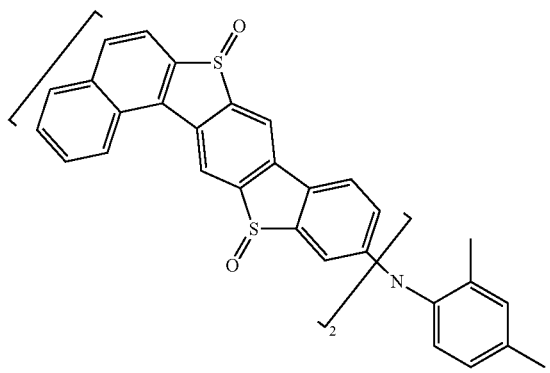
(72)

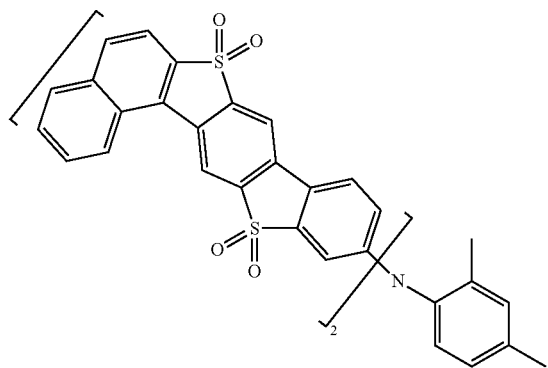
(73)
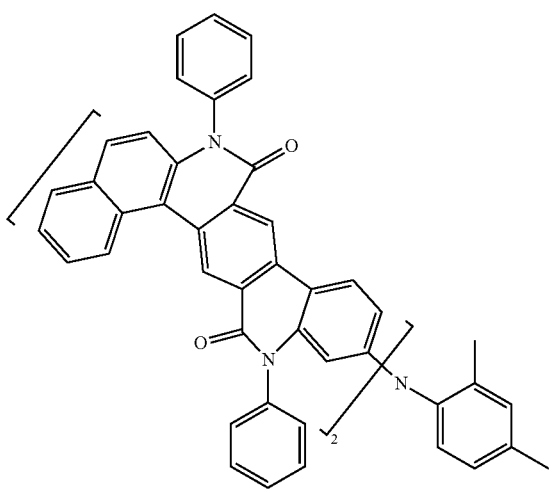
(74)
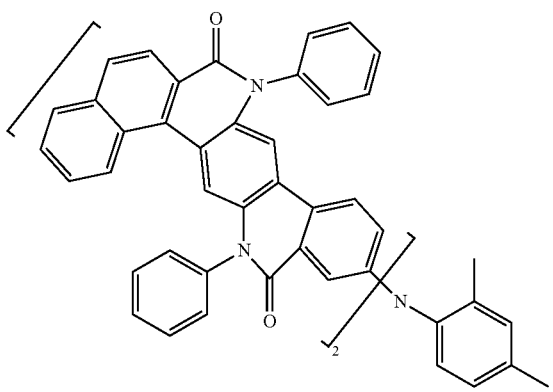
(75)

(76)
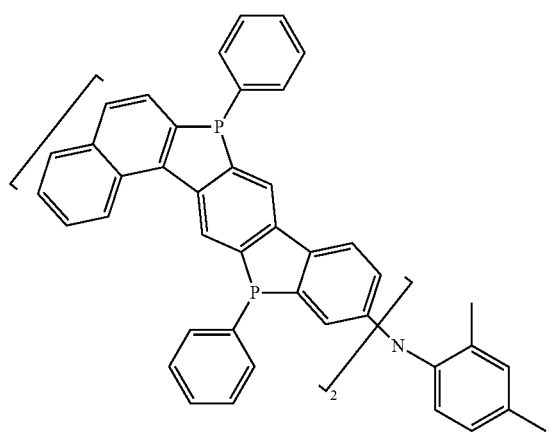
(77)
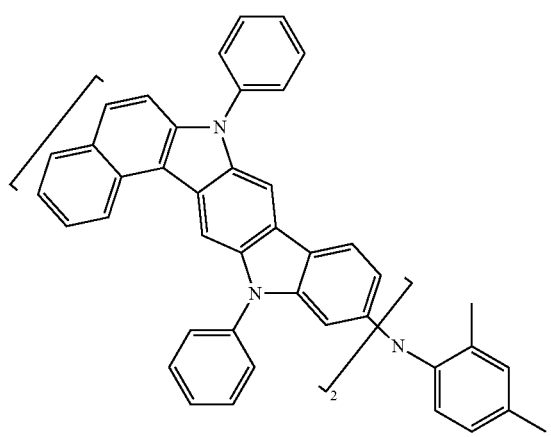
(78)
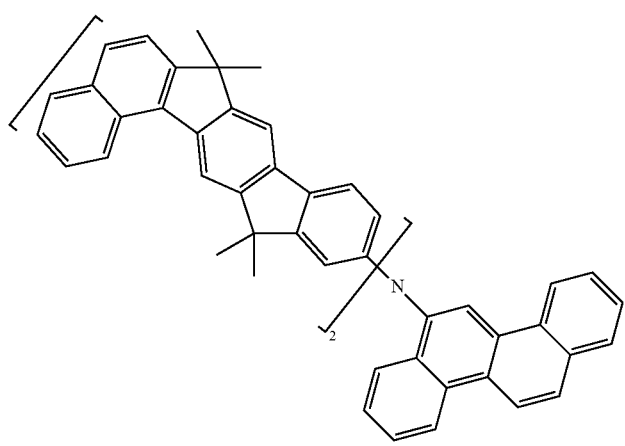

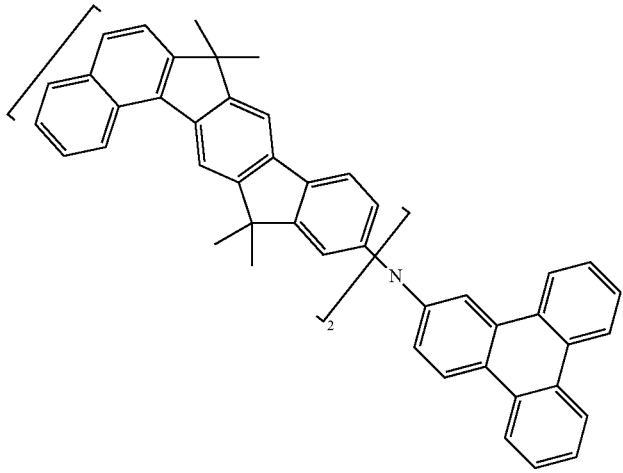
(79)

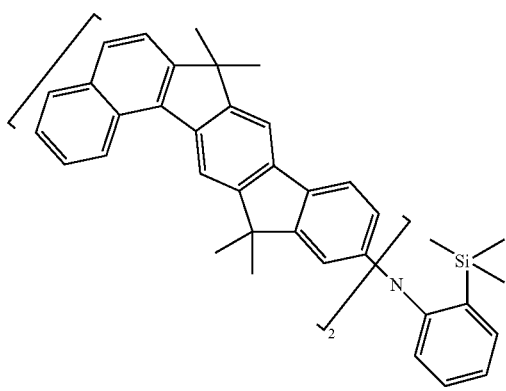
(80)

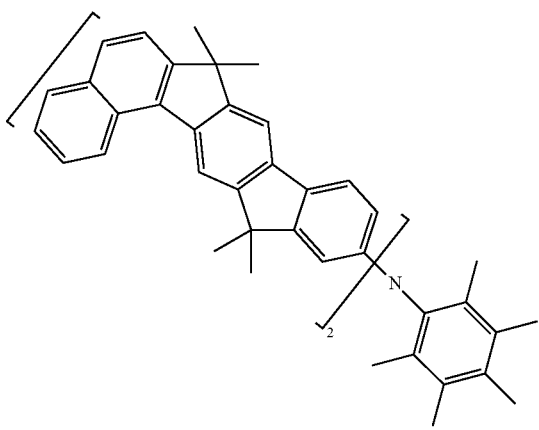
(81)

The compounds according to the invention can be synthesised by processes of organic preparative chemistry which are generally known to the person skilled in the art. Examples of reactions which are preferably employed are halogenations and transition metal-catalysed coupling reactions, preferably Suzuki couplings and Buchwald couplings.

Illustrative general synthetic routes for the preparation of the compounds are shown below.

The process according to Scheme 1 starts from a triarylamino compound which contains reactive groups on two of the three aryl groups. A biaryl compound carrying precursors for the formation of bridges X can be coupled in these positions via a transition metal-catalysed reaction, for example a Suzuki reaction. In a subsequent cyclisation reaction, the bridges X are introduced. Further functionalisation reactions can be carried out in order to reach the final compound according to the invention.

Scheme 1

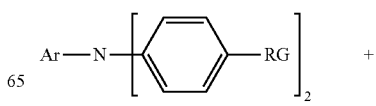

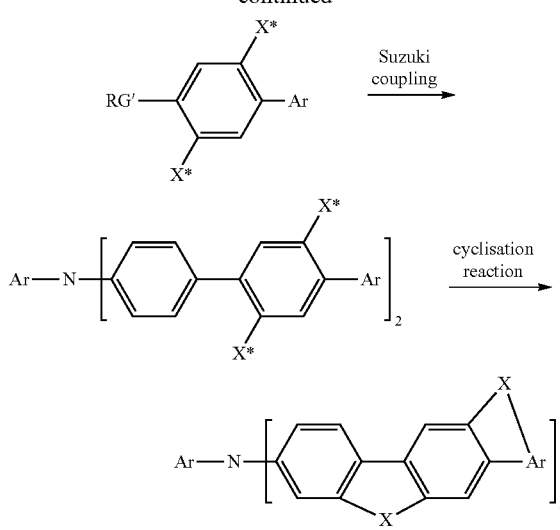

Ar: aryl or heteroaryl group
RG, RG': reactive group
X*: precursor for bridge X
X: defined as above The process according to Scheme 2 starts from a bridged trisaryl compound, preferably an indenofluorene compound. This is functionalised in a first step, for example by bromination. A group Ar is subsequently introduced by a transition metal-catalysed coupling reaction, for example by Suzuki coupling. After further selective functionalisation on the opposite side of the parent structure, a diarylamino group can be introduced via a further coupling reaction, for example a Buchwald coupling. Further functionalisation reactions can be carried out in order to reach the final compound according to the invention.

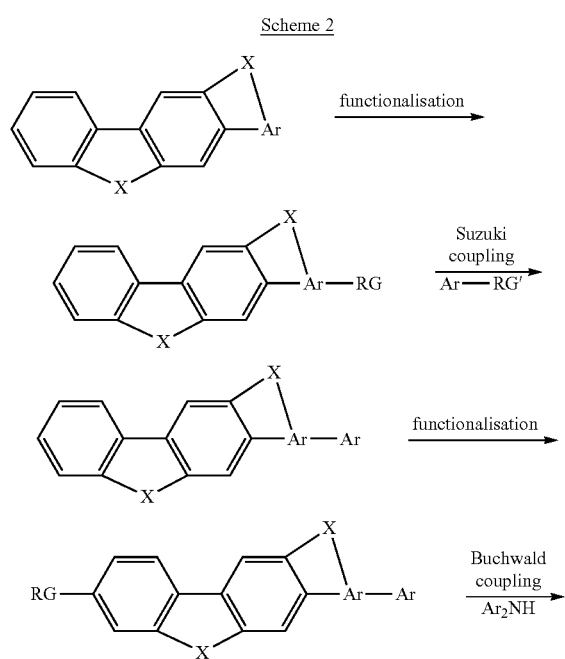

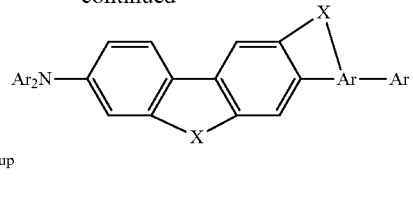

Ar: aryl or heteroaryl group
RG: reactive group
X: defined as above

In a process according to Scheme 3, firstly the indenofluorene derivative is prepared, then functionalised, and subsequently reacted in two Buchwald couplings, using different amine derivatives in each case. In this way, compounds containing three different groups on the central nitrogen atom can be obtained, in particular compounds of the formula (III).

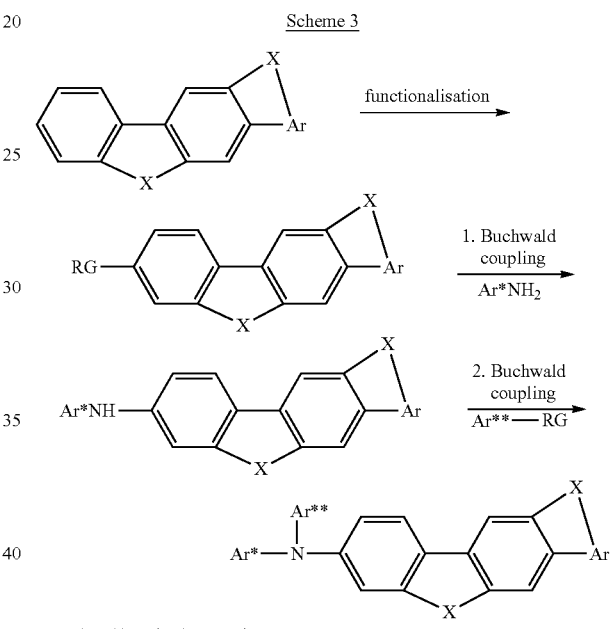

Ar, Ar*, Ar**: aryl or heteroaryl group
RG: reactive group
X: defined as above

The invention thus furthermore relates to a process for the preparation of a compound of the formula (I), (II) or (III), characterised in that one or more organometallic coupling processes are employed.

Preference is given to coupling processes selected from Buchwald couplings and Suzuki couplings.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I), (II) or (III), where the bond(s) to the polymer, oligomer or dendrimer may be localised at any desired positions in formula (I), (II) or (III) which are substituted by $R^1$ or $R^2$. Depending on the linking of the compound of the formula (I), (II) or (III), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I), (II) or (III) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I), (II) or (III) may be linked via a trivalent or polyvalent group, for example via a trivalent or polyvalent aromatic or heteroaromatic group, to form a branched or dendritic oligomer or polymer.

The same preferences as described above for compounds of the formula (I), (II) or (III) apply to the recurring units of the formula (I), (II) or (III) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I), (II) or (III) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I), (II) or (III) or at least one polymer, oligomer or dendrimer containing at least one unit of the formula (I), (II) or (III), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I), (II) or (III) according to the invention are suitable for use in electronic devices, in particular in organic electroluminescent devices (OLEDs). Depending on the substitution, the compounds are employed in different functions and layers.

The invention therefore furthermore relates to the use of the compounds of the formula (I), (II) or (III) in electronic devices and to electronic devices themselves which comprise one or more compounds of the formula (I), (II) or (III). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

Particular preference is given to organic electroluminescent devices comprising anode, cathode and at least one emitting layer, characterised in that at least one organic layer comprises at least one compound of the formula (I), (II) or (III).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably the following:

anode-hole-injection layer-hole-transport layer-emitting layer-electron-transport layer-electron-injection layer-cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I), (II) or (III) and where the three layers exhibit blue, green and orange or red emission (for the basic structure see, for example, WO 2005/011013). The compounds according to the invention may alternatively and/or additionally also be present in the hole-transport layer or in another layer.

It should be noted that, for the generation of white light, an emitter compound used individually which emits in a broad wavelength range may also be suitable instead of a plurality of emitter compounds emitting in colour.

It is preferred for the compound of the formula (I), (II) or (III) to be employed in an emitting layer. In particular, the compound of the formula (I), (II) or (III) is suitable for use as emitting material (dopant).

The compound according to the invention is particularly suitable for use as blue-emitting emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as emitting material in an emitting layer, it is preferably employed in combination with one or more host materials. A host material in a system comprising host and dopant is taken to mean the component which is present in the system in the higher proportion. In the case of a system comprising one host and a plurality of dopants, the host is taken to mean the component whose proportion in the mixture is the highest.

The proportion of the compound according to the invention in the mixture of the emitting layer is between 0.1 and 50.0% by vol., preferably between 0.5 and 20.0% by vol., particularly preferably between 1.0 and 10.0% by vol. Correspondingly, the proportion of the host material or host materials is between 50.0 and 99.9% by vol., preferably between 80.0 and 99.5% by vol., particularly preferably between 90.0 and 99.0% by vol.

Preferred host materials (matrix materials) for use in combination with the materials according to the invention are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Depending on the substitution pattern, the compounds according to the invention can also be employed in other layers, for example as hole-transport materials in a hole-injection or hole-transport layer or as host materials in an emitting layer, preferably as host materials for phosphorescent emitters.

Generally preferred classes of material for use as corresponding functional materials in the organic electroluminescent devices according to the invention are indicated below.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred fluorescent dopants, besides the compounds according to the invention, are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Preferred matrix materials for use with fluorescent dopants are indicated above.

Preferred matrix materials for phosphorescent dopants are aromatic amines, in particular triarylamines, for example in accordance with US 2005/0069729, carbazole derivatives (for example CBP, N,N-biscarbazolyl-biphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAlq.

Besides the compounds according to the invention, suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used in a hole-transport, hole-injection or electron-blocking layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847). Furthermore suitable hole-transport and hole-injection materials are derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I), (II) or (III) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

The following working examples serve to illustrate and explain the invention.

WORKING EXAMPLES

A) Synthesis Examples

4-Bromotoluene and diphenylamine are commercially available. The synthesis of diethyl 2-chloro-5-naphthalen-1-ylterephthalate is described in WO 2010/012328 A1.

A-1) Variant I

Synthesis of 7,7,13,13-tetramethyl-N-(7,7,13,13-tetramethyl-7,13-dihydrobenzo[g]indeno[1,2-b]fluoren-11-yl)-N-(p-tolyl)-7,13-dihydrobenzo[g]indeno[1,2-b]fluoren-11-amine (I)

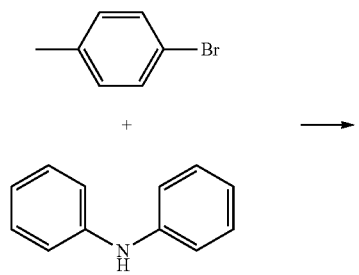

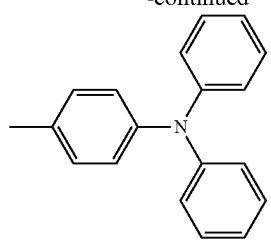

Ia

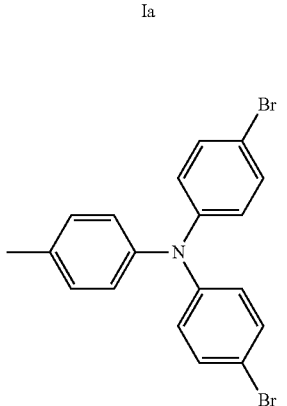

Ib

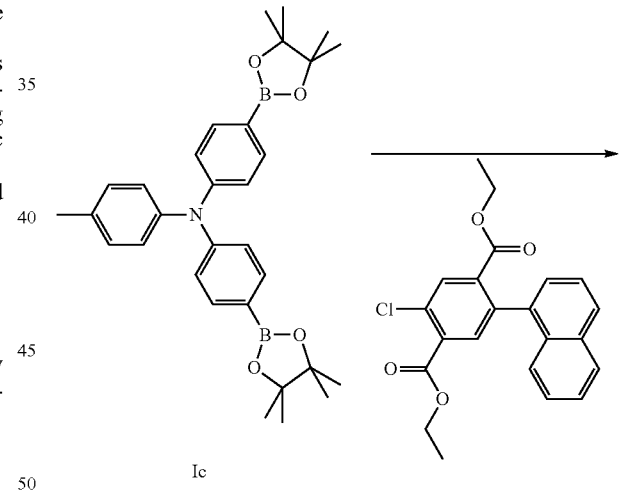

Ic

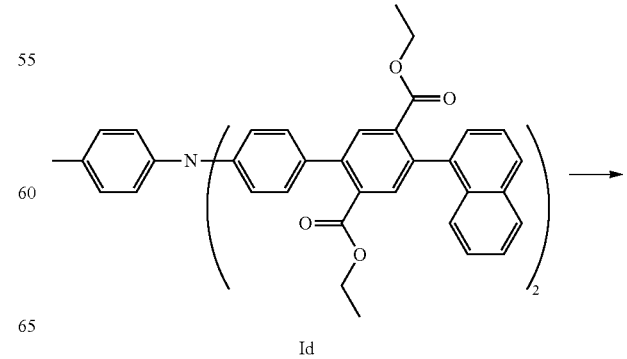

Id

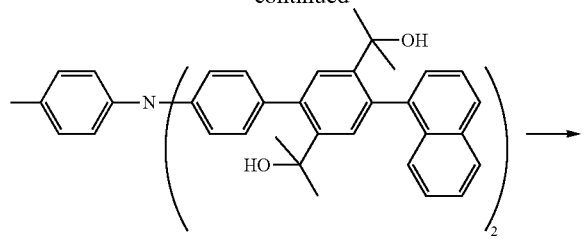

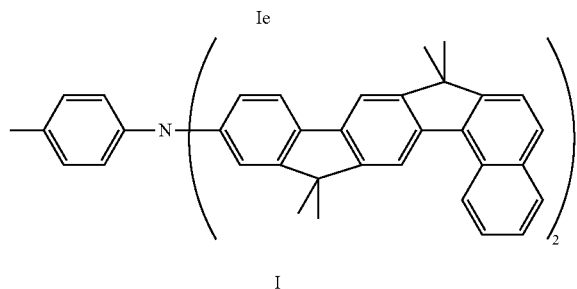

(4-Methylphenyl)diphenylamine (Ia)

Besides the synthesis described here, further syntheses which are described in the literature are available to the person skilled in the art. Diphenylamine (88.34 g, 520 mmol) and 4-bromotoluene (82.0 g, 470 mmol) are dissolved in 900 ml of toluene. Tri-ortho-tolylphosphine (1.46 g, 4.7 mmol), palladium(II) acetate (0.53 g, 2.4 mmol) and sodium tert-butoxide (69.1 g, 700 mmol) are subsequently added to the reaction solution, which is then heated under reflux for 3 days. The mixture is extended with toluene and dist. H$_2$O at room temperature, the organic phase is separated off, and the aqueous phase is extracted a number of times with toluene. The org. phase is dried using MgSO$_4$, filtered through AlOx and evaporated. The residue is brought to precipitation using heptane and recrystallised from isopropanol, giving (4-methylphenyl)diphenylamine as a colourless solid (85.7 g, 70% of theory).

The following compounds are prepared analogously:

-continued

| Amine | Bromoarene | Product | Yield |
|---|---|---|---|
| (diphenylamine structure) | (4-bromodibenzofuran structure) | (N,N-diphenyl-dibenzofuran-4-amine structure) | 68% |

Bis-(4-bromophenyl)-p-tolylamine (Ib)

(4-Methylphenyl)diphenylamine (85.2 g, 330 mmol) is dissolved in 1 l of DCM and cooled to 0° C. N-Bromosuccinimide (117 g, 660 mmol) is added in small portions with stirring at such a rate that the reaction temperature does not exceed 5° C. The reaction mixture is warmed to room temperature in an ice bath overnight. 500 ml of a 10% $Na_2SO_3$ solution are then added, and the phases are separated. The aqueous phase is extracted a number of times with DCM. The organic phase is washed with dist. $H_2O$, dried and freed from solvent. The solid obtained is recrystallised a number of times from 1-butanol, giving 129 g of a colourless solid (94% of theory).

4-Methyl-N,N-bis(4-(4,4,5,5-tetramethyl-1,3,2-dioxaborolan-2-yl)-phenylaniline (Ic)

Bis-(4-bromophenyl)-p-tolylamine (128 g, 310 mmol) and bispinacolatodiborane (195 g, 770 mmol) are dissolved in 1.5 l of THF. Potassium acetate (241 g, 2460 mmol) and 1,1'-bis(diphenylphosphino)ferrocene-palladium(II) dichloride*DCM (7.52 g, 9.2 mmol) are then added to the reaction solution, which is then heated under reflux for six days. After cooling to room temperature, the batch is extended with DCM and dist. $H_2O$, and the aqueous phase is extracted a number of times with DCM. The combined organic phases are washed with dist. $H_2O$ and, after drying using $MgSO_4$, filtered through AlOx. The solvent is removed at atmospheric pressure. The solid obtained is washed with heptane and acetonitrile, giving 110 g of a pale-grey powder (70% of theory).

Tetraethyl 4',4'''-(p-tolylazandiyl)bis(4-(naphthalen-1-yl)-[1,1'-biphenyl]-2,5-dicarboxylate)

4-Methyl-N,N-bis(4-(4,4,5,5-tetramethyl-1,3,2-dioxaborolan-2-yl)phenylaniline (110 g, 215 mmol) and diethyl 2-chloro-5-naphthalen-1-ylterephthalate (189 g, 495 mmol) are dissolved in 1.2 l of toluene, and tetrakis-(triphenylphosphine)palladium (4.97 g, 4.3 mmol) and 2-dicyclohexylphosphino-2',6'-dimethoxybiphenyl (3.53 g, 8.6 mmol) are added. Tetraethylammonium hydroxide (20% in $H_2O$) (450 ml, 645 mmol) is subsequently added to the reaction solution. The batch is heated under reflux for seven hours, cooled to room temperature and extended with dist. $H_2O$. After phase separation, the aqueous phase is extracted a number of times with toluene. The combined organic phases are washed with dist. $H_2O$, dried over $MgSO_4$ and filtered through AlOx. The organic phase is evaporated to give a dark-orange viscous oil and purified by chromatography (silica gel, heptane/THF 85:15), giving 147 g (72% of theory) of tetraethyl 4',4'''-(p-tolylazandiyl)bis(4-(naphthalen-1-yl)-[1,1'-biphenyl]-2,5-dicarboxylate) in the form of an intensely yellow solid.

The following compounds are prepared analogously:

| Boronic acid ester | Terephthalic acid ester derivative | Product | Yield |
|---|---|---|---|
| (bis-pinacolboronate ester of tolyl-diphenylamine) | (diethyl chloro-phenanthrenyl-terephthalate) | (tolylamine bis-biphenyl-phenanthrenyl-dicarboxylate product) | 69% |

-continued

| Boronic acid ester | Terephthalic acid ester derivative | Product | Yield |
|---|---|---|---|
| as above | | | 76% |
| as above | | | 74% |
| as above | | | 68% |

The following compound can be prepared analogously:

| Boronic acid ester | Terephthalic acid ester derivative | Product |
|---|---|---|
| | | |

2-[4'-{[2',5'-Bis-(1-hydroxy-1-methylethyl)-4'-naphthalen-1-ylbiphenyl-4-yl]-p-tolylamino}-5-(1-hydroxy-1-methylethyl)-4-naphthalen-1-yl-biphenyl-2-yl]propan-2-ol (Ie)

Tetraethyl 4',4'''-(p-tolylazandiyl)bis(4-(naphthalen-1-yl)-[1,1'-biphenyl]-2,5-dicarboxylate) (147 g, 154 mmol) is dissolved in 750 ml of THF, and methylmagnesium chloride (20% solution in THF) (617 ml, 1700 mmol) is added at 0° C. The reaction solution is allowed to warm to room temperature in an ice bath overnight. The batch is carefully hydrolysed using saturated NH₄Cl solution and neutralised using 4% hydrochloric acid. The mixture is extended with dist. H₂O and extracted thoroughly with toluene. The combined organic phases are washed a number of times with dist. H₂O and once with NaHCO₃ solution and dried over MgSO₄. After removal of the solvent in vacuo, a pale-beige solid is obtained. This is washed with a heptane/isopropanol mixture, giving 136 g (98% of theory) of 2-[4'-{[2',5'-bis-(1-hydroxy-1-methylethyl)-4'-naphthalen-1-ylbiphenyl-4-yl]-p-tolylamino}-5-(1-hydroxy-1-methylethyl)-4-naphthalen-1-ylbiphenyl-2-yl]propan-2-ol as a colourless solid.

7,7,13,13-Tetramethyl-N-(7,7,13,13-tetramethyl-7,13-dihydrobenzo[g]-indeno[1,2-b]fluoren-11-yl)-N-(p-tolyl)-7,13-dihydrobenzo[g]indeno-[1,2-b]fluoren-11-amine (I) (Synthesis Example 1)

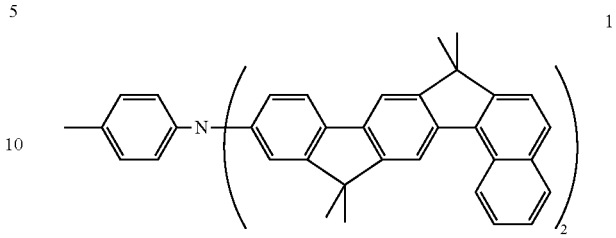

2-[4'-{[2',5'-Bis-(1-hydroxy-1-methylethyl)-4'-naphthalen-1-ylbiphenyl-4-yl]-p-tolylamino}-5-(1-hydroxy-1-methylethyl)-4-naphthalen-1-ylbiphenyl-2-yl]-propan-2-ol (135 g, 151 mmol) is dissolved in 1.3 l of DCM, and methanesulfonic acid (69 ml, 1060 mmol) and polyphosphoric acid (156 g, 1350 mmol) are added at −20° C. The reaction solution is allowed to warm to room temperature overnight. The yellow solid which precipitates is filtered off and purified by Soxhlett extraction and subsequent sublimation, giving 47.4 g of a yellow solid (38% of theory).

The following compounds are prepared analogously:

| Synthesis Example | Structure | Yield |
|---|---|---|
| 2 | 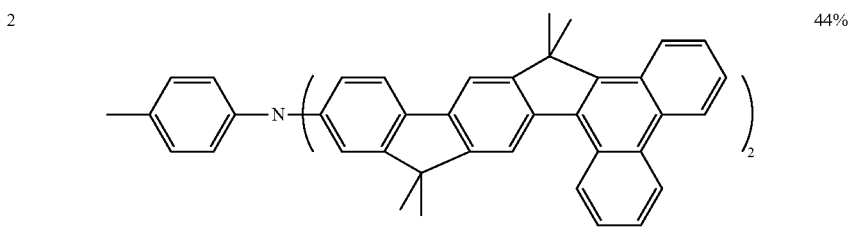 | 44% |
| 3 | 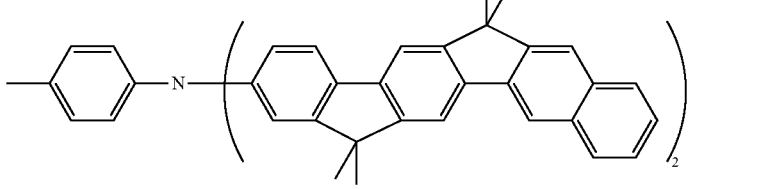 | 42% |
| 4 | 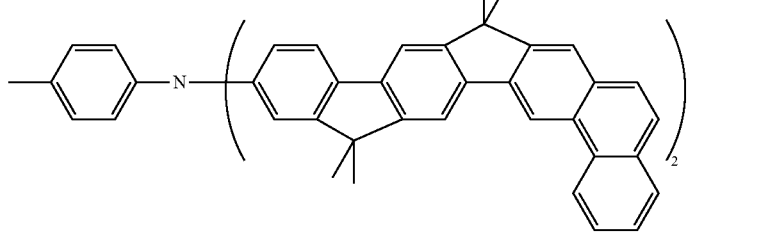 | 39% |

| Synthesis Example | Structure | Yield |
|---|---|---|
| 5 | 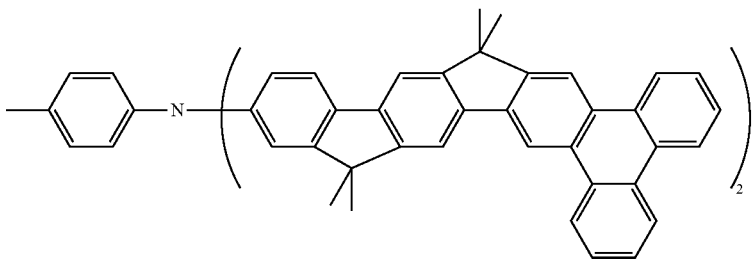 | 34% |

The following compound can be prepared analogously:

| Synthesis Example | Structure |
|---|---|
| 6 | 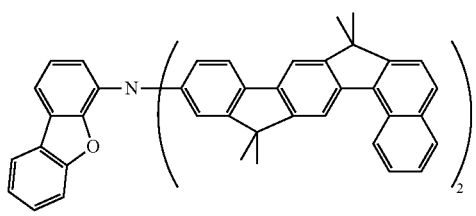 |

A-2) Variant II 7,7,13,13-Tetramethyl-5-phenyl-7,13-dihydrobenzo[g]indeno[1,2-b]-fluorene (IIa)

12.8 g (103 mmol) of benzeneboronic acid, 37.7 g (86 mmol) of 5-bromo-7,7,13,13-tetramethyl-7,13-dihydrobenzo[g]indeno[1,2-b]fluorene and 29.7 g (215 mmol) of $K_2CO_3$ are suspended in 500 ml of toluene/water (1:1). 0.99 g (0.86 mmol) of tetrakis(triphenylphosphine)palladium is added to this suspension, and the reaction mixture is heated under reflux for 16 h. After cooling, the reaction mixture is diluted with ethyl acetate, the organic phase is separated off, washed three times with 100 ml of water and subsequently evaporated to dryness. After filtration of the crude product through silica gel with toluene, the residue which remains is recrystallised from heptane/toluene. The yield is 29.2 g (78% of theory).

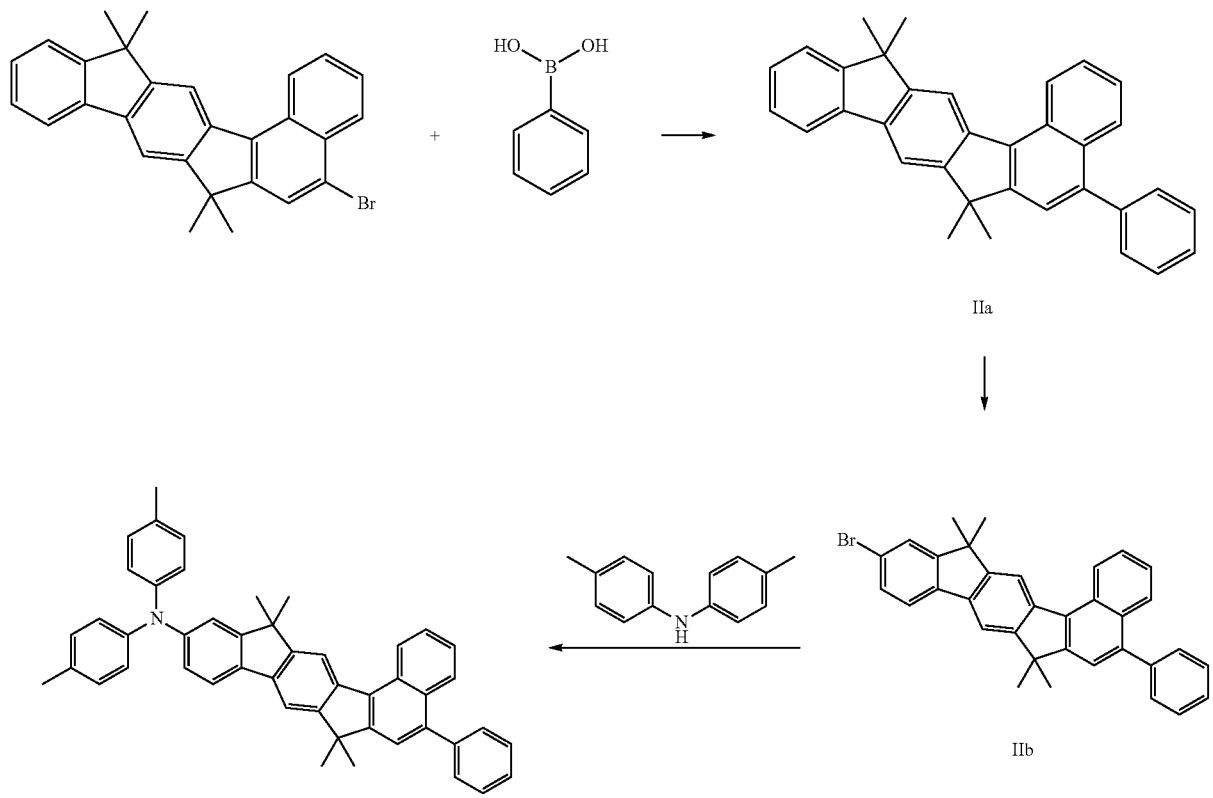

The following compounds are prepared analogously:

| Starting material 1 | Starting material 2 | Product | Yield |
|---|---|---|---|
| | | | 74% |
| | | | 69% |
| | | | 79% |
| | | | 73% |
| | | | 67% |

| Starting material 1 | Starting material 2 | Product | Yield |
|---|---|---|---|
| | | | 59% |
| | | | 81% |

11-Bromo-7,7,13,13-tetramethyl-5-phenyl-7,13-dihydrobenzo[g]-indeno[1,2-b]fluorene (IIb)

29.2 g (67 mmol) of 7,7,13,13-tetramethyl-5-phenyl-7,13-dihydrobenzo-[g]indeno[1,2-b]fluorene (IIa) are dissolved in 500 ml of CHCl₃, and 10.8 g (67 mmol) of bromine, dissolved in 500 ml of CHCl₃, are slowly added at −10° C. When the reaction is complete, water is added, the organic phase is separated off, dried and evaporated. The crude product is subsequently washed by stirring a number of times with hot heptane/toluene (5:1). Yield: 30.5 g (89%) of the product as a white solid.

The following compounds are prepared analogously:

| Starting material 1 | Product | Yield |
|---|---|---|
| | | 83% |
| | | 75% |

-continued

| Starting material 1 | Product | Yield |
|---|---|---|
| | | 81% |
| | | 62% |
| | | 72% |
| | | 44% |
| | | 87% |

7,7,13,13-Tetramethyl-5-phenyl-N,N-di-p-tolyl-7,13-dihydrobenzo-[g]indeno[1,2-b]fluoren-11-amine (II) (Synthesis Example 7)

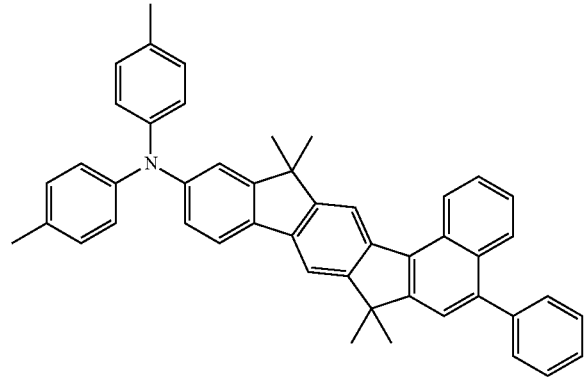 [SMILES: Cc1ccc(N(c2ccc(C)cc2)c2ccc3c(c2)C(C)(C)c2cc4c(cc2-3)C(C)(C)c2cc(-c3ccccc3C)c3ccccc3c2-4)cc1]

(II)

9.74 g of di-p-tolylamine (49.4 mmol), 11-bromo-7,7,13,13-tetramethyl-5-phenyl-7,13-dihydrobenzo[g]indeno[1,2-b]fluorene (IIb) (41.1 mmol) are dissolved in 500 ml of toluene. The solution is degassed and saturated with argon. 2.5 ml (2.5 mmol) of a 1 M tri-tert-butylphosphine solution and 0.355 g (1.23 mmol) of palladium(II) acetate are then added. 11.9 g of sodium tert-butoxide (124 mmol) are subsequently added. The reaction mixture is heated at the boil for 12 h under a protective-gas atmosphere. Water is subsequently added to the mixture, the organic phase is washed three times with water, dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9%. The yield is 15.2 g (58% of theory).

The following compounds are prepared analogously:

| Ex. | Starting material 1 | Starting material 2 | Product | Yield |
|---|---|---|---|---|
| 8 | | | | 69% |
| 9 | | | | 78% |
| 10 | | | | 72% |

-continued

| Ex. | Starting material 1 | Starting material 2 | Product | Yield |
|---|---|---|---|---|
| 11 | | | | 83% |
| 12 | | | | 76% |

| Ex. | Starting material 1 | Starting material 2 | Product | Yield |
|---|---|---|---|---|
| 13 | 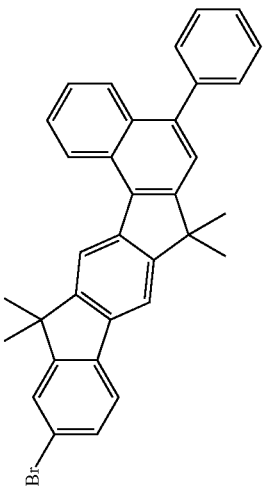 | 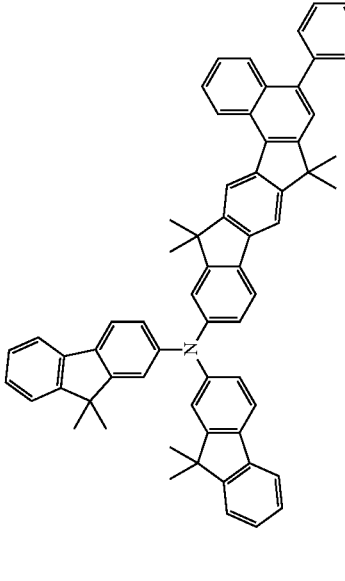 | 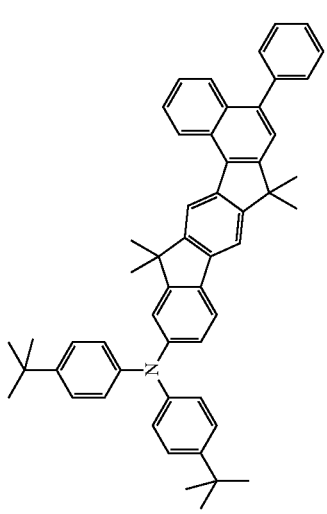 | 67% |
| 14 | 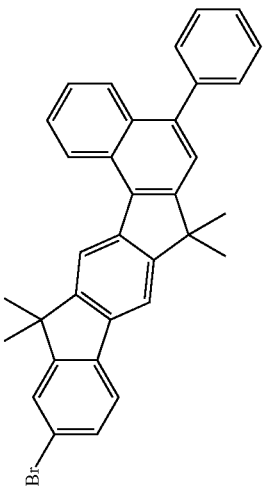 | 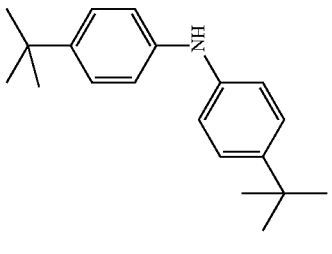 | 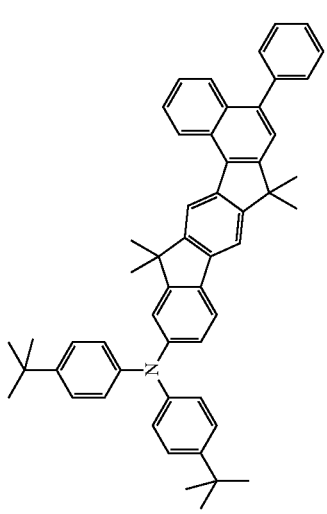 | 75% |

| Ex. | Starting material 1 | Starting material 2 | Product | Yield |
|---|---|---|---|---|
| 15 | | | | 81% |
| 16 | | | | 58% |
| 17 | | | | 73% |

| Ex. | Starting material 1 | Starting material 2 | Product | Yield |
|---|---|---|---|---|
| 18 | 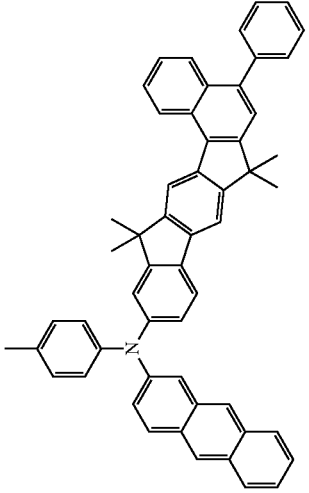 | 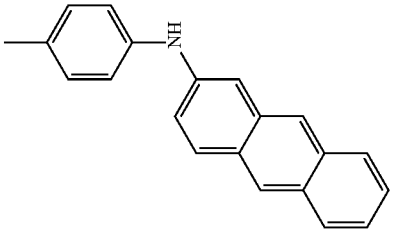 | 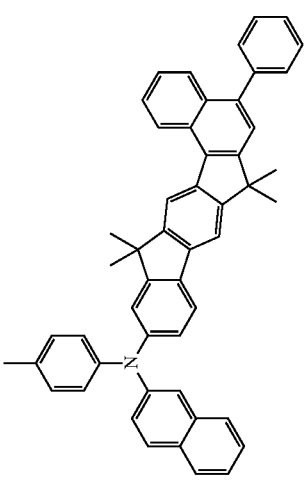 | 61% |
| 19 | 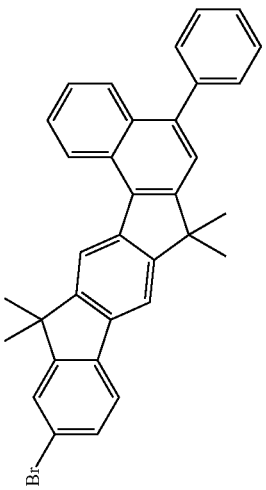 | 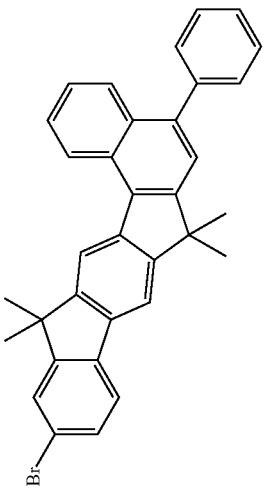 | 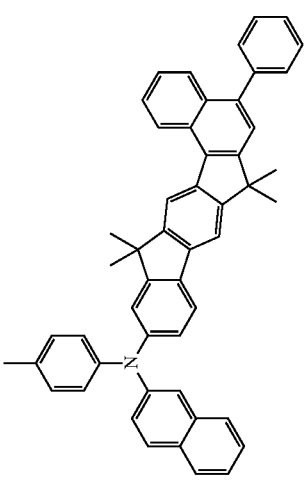 | 68% |

| Ex. | Starting material 1 | Starting material 2 | Product | Yield |
|---|---|---|---|---|
| 20 | | | | 72% |
| 21 | | | | 81% |
| 22 | | | | 79% |

| Ex. | Starting material 1 | Starting material 2 | Product | Yield |
|---|---|---|---|---|
| 23 | 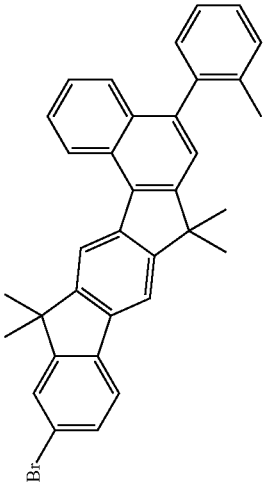 | 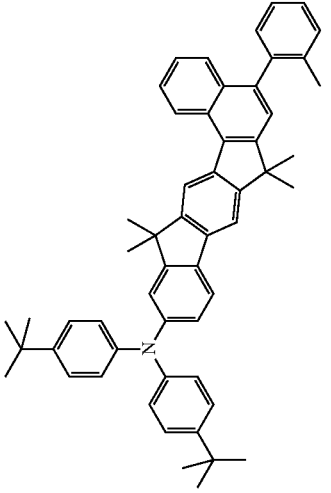 | 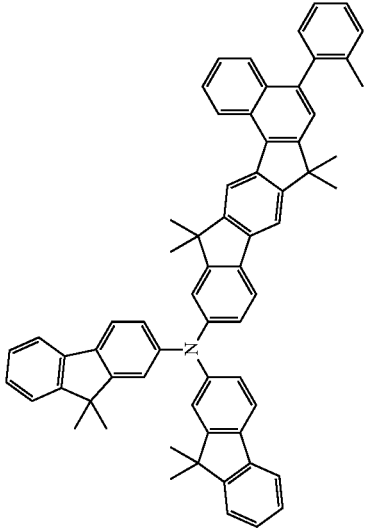 | 77% |
| 24 | 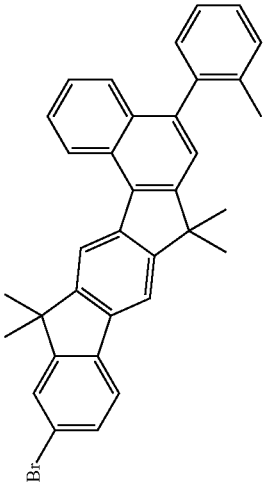 | 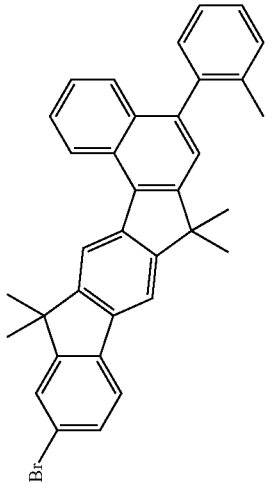 | 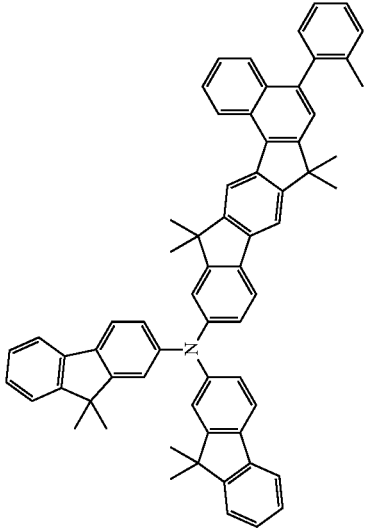 | 64% |

| Ex. | Starting material 1 | Starting material 2 | Product | Yield |
|---|---|---|---|---|
| 25 | 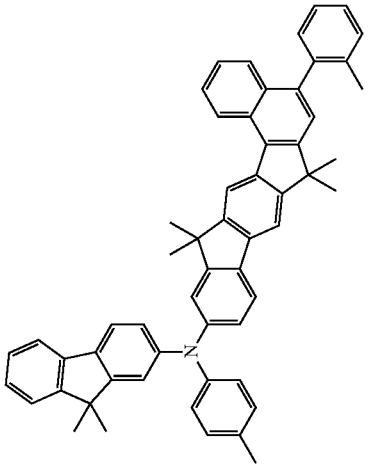 | 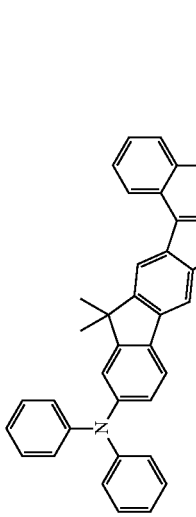 | 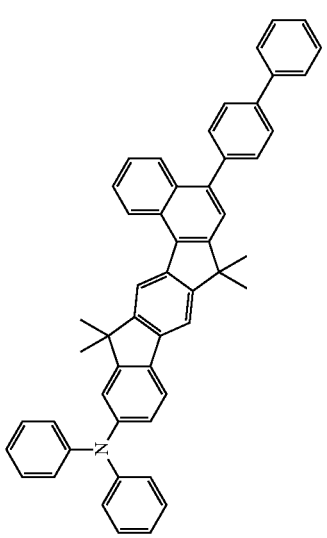 | 77% |
| 26 | 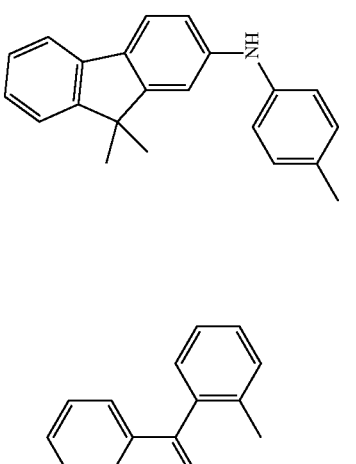 | 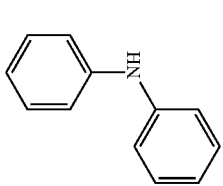 | 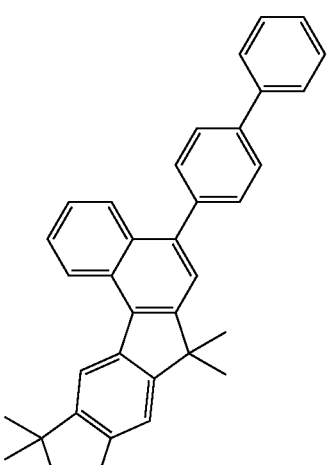 | 84% |

| Ex. | Starting material 1 | Starting material 2 | Product | Yield |
|---|---|---|---|---|
| 27 | 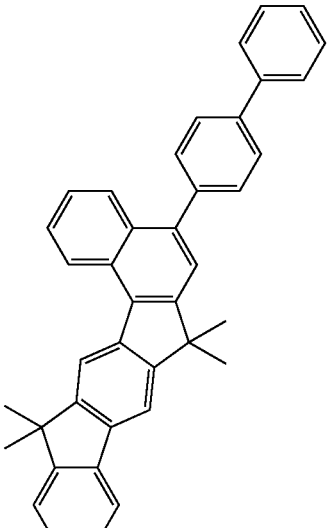 | 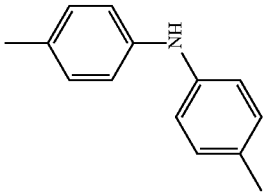 | 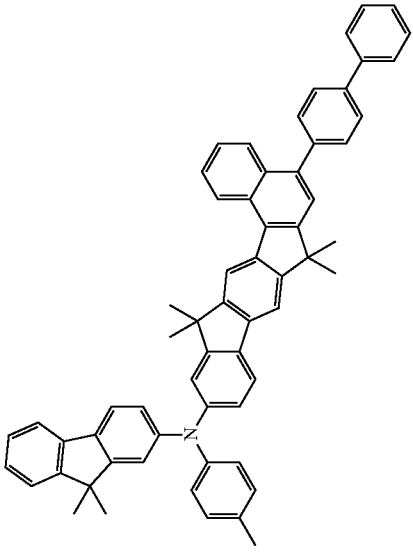 | 72% |
| 28 | 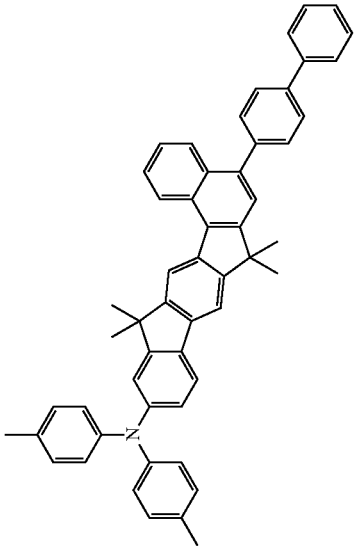 | 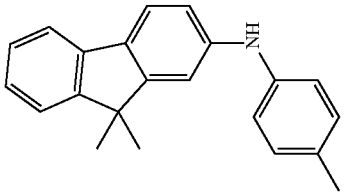 | 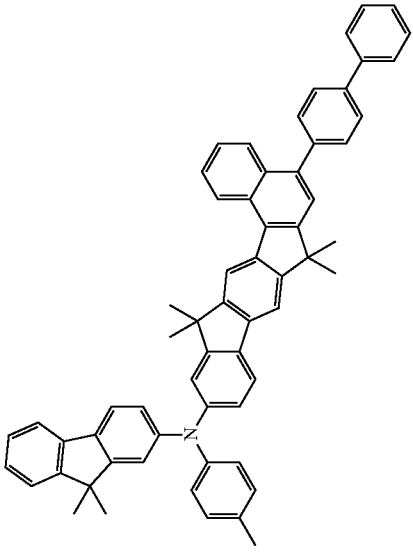 | 68% |

-continued

| Ex. | Starting material 1 | Starting material 2 | Product | Yield |
|---|---|---|---|---|
| 29 | | | | 81% |
| 30 | | | | 79% |

| Ex. | Starting material 1 | Starting material 2 | Product | Yield |
|---|---|---|---|---|
| 31 | 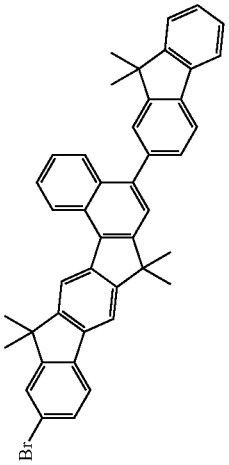 | 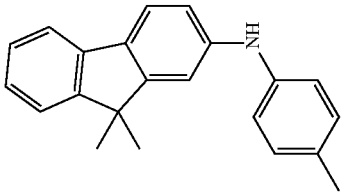 | 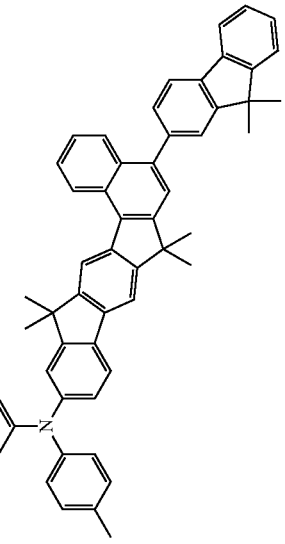 | 73% |
| 32 | 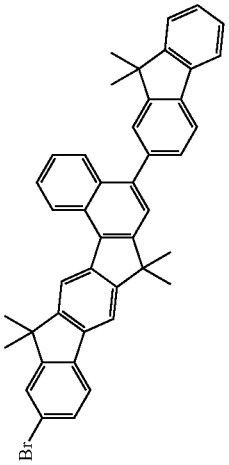 | 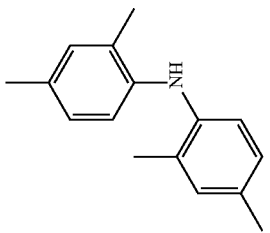 | 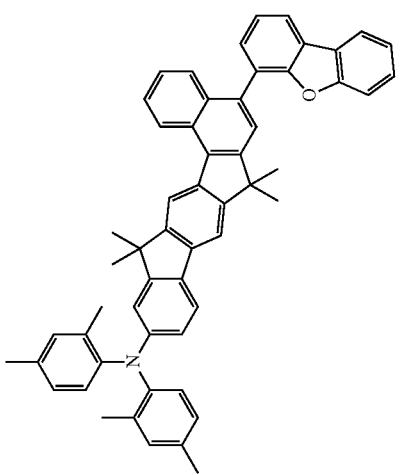 | 77% |

| Ex. | Starting material 1 | Starting material 2 | Product | Yield |
|---|---|---|---|---|
| 33 | | | | 82% |
| 34 | | | | 77% |
| 35 | | | | 65% |

| Ex. | Starting material 1 | Starting material 2 | Product | Yield |
|---|---|---|---|---|
| 36 | | | | 79% |

A-3) Variant III
III-1) Synthesis of Building Blocks (i)
General Reaction Scheme:

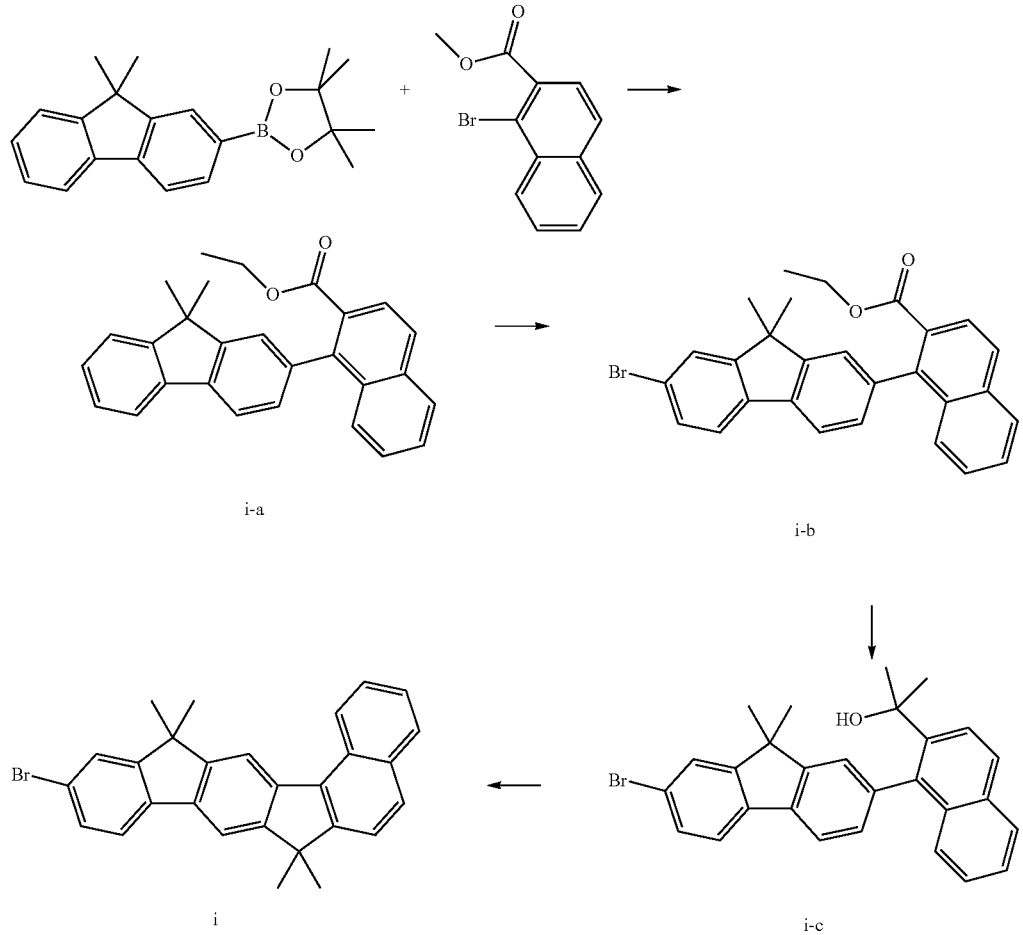

Ethyl 1-(9,9-dimethyl-9H-fluoren-2-yl)-2-naphthoate (i-a)

Methyl 1-bromonaphthalene-2-carboxylate (150 g, 563 mmol), 9,9-dimethyl-9H-fluoren-2-ylboronic ester (148.9 g, 619 mmol) and potassium phosphate monohydrate (286 g, 1.182 mol) are dissolved in a mixture of 1.2 l of toluene and 1 l of water, and palladium acetate (1.28 g, 5.6 mmol) and tri-ortho-tolylphosphine (3.5 g, 11.3 mmol) are added. The batch is heated under reflux overnight, cooled to room temperature and extended with dist. water. After phase separation, the aqueous phase is extracted a number of times with toluene. The combined organic phases are washed with dist. water, dried over magnesium sulfate and filtered through aluminium oxide. The organic phase is evaporated to an orange oil, giving 213 g of product (99% of theory).

Ethyl 1-(7-bromo-9,9-dimethyl-9H-fluoren-2-yl)-2-naphthoate (i-b)

(i-a) (122 g, 295 mmol) is dissolved in 1 l of chloroform and cooled to 0° C. A dibromine solution (14.4 ml, 280 mmol) in 0.5 l of chloroform is added dropwise with stirring at such a rate that the reaction temperature does not exceed 5° C. The reaction mixture is warmed to room temperature in an ice bath overnight. 500 ml of a 10% sodium thiosulfate solution are added, and the phases are separated. After phase separation, the aqueous phase is extracted a number of times with chloroform. The combined organic phases are washed with dist. water, dried over magnesium sulfate and filtered through aluminium oxide. The organic phase is evaporated to a colourless oil, giving 128 g of product (95% of theory).

2-(1-(7-Bromo-9,9-dimethyl-9H-fluoren-2-yl)naphthalen-2-yl)propan-2-ol (i-c)

(i-b) (80 g, 175 mmol) and cerium(III) chloride (48 g, 247 mmol) are dissolved in 800 ml of THF, and methylmagnesium chloride (3 M solution in THF) (146 ml, 437 mmol) is added at 0° C. The reaction solution is allowed to warm to room temperature in an ice bath overnight. The batch is carefully hydrolysed using saturated $NH_4Cl$ solution and neutralised using 4% hydrochloric acid. The mixture is extended with dist. water and extracted thoroughly with toluene. The combined organic phases are washed a number of times with dist. water and once with sodium hydrogencarbonate solution and dried over magnesium sulfate. After removal of the solvent in vacuo, a pale-beige solid is obtained. This is recrystallised from a heptane/toluene mixture, giving 69 g (86% of theory) as a colourless solid.

11-Bromo-7,7,13,13-tetramethyl-7,13-dihydrobenzo[g]indeno[1,2-b]-fluorene (i)

(i-c) (61 g, 133 mmol) is dissolved in 300 ml of DCM, and methanesulfonic acid (60 ml, 933 mmol) and polyphosphoric acid (91 g, 933 mmol) are added at 0° C. The reaction solution is allowed to warm to room temperature overnight. The mixture is extended with ethanol and evaporated. The residue is dissolved in toluene, washed with NaOH solution and dist. water and dried over magnesium sulfate. After removal of the solvent in vacuo, the solid is recrystallised from ethanol, giving 55 g of a yellow solid (93% of theory).

The following compounds are prepared analogously:

| Starting material 1 | Product | Yield (4 steps) |
|---|---|---|
| | | 68% |
| | | 59% |
| | | 64% |
| | | 74% |

III-2) Synthesis of Building Block (ii-1)
General Reaction Scheme:

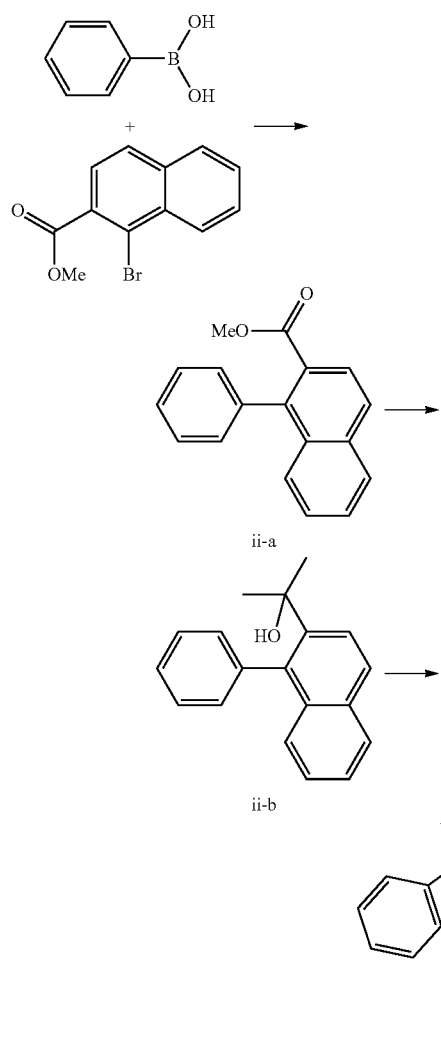

Methyl 1-phenylnaphthalene-2-carboxylate (ii-a)

Methyl 1-bromonaphthalene-2-carboxylate (70.0 g, 264 mmol), phenylboronic acid (38.6 g, 317 mmol) and potassium phosphate monohydrate (182 g, 792 mmol) are dissolved in a mixture of 0.2 l of toluene, 0.2 l of dioxane and 0.2 l of water, and palladium acetate (1.18 g, 5.3 mmol) and tri-ortho-tolylphosphine (3.2 g, 10.6 mmol) are added. The batch is heated under reflux overnight, cooled to room temperature and extended with dist. water. After phase separation, the aqueous phase is extracted a number of times with toluene. The combined organic phases are washed with dist. water, dried over magnesium sulfate and filtered through aluminium oxide. The organic phase is evaporated to an orange oil, giving 69 g of product (99% of theory).

2-(1-Phenylnaphthalen-2-yl)propan-2-ol (ii-b)

(ii-a) (69 g, 264 mmol) and cerium(III) chloride (71 g, 291 mmol) are dissolved in 500 ml of THF, and methylmagnesium chloride (3 M solution in THF) (308 ml, 925 mmol) is added at 0° C. The reaction solution is allowed to warm to room temperature in an ice bath overnight. The batch is carefully hydrolysed using saturated $NH_4Cl$ solution and neutralised using 4% hydrochloric acid. The mixture is extended with dist. water and extracted thoroughly with toluene. The combined organic phases are washed a number of times with dist. water and once with sodium hydrogencarbonate solution and dried over magnesium sulfate. After removal of the solvent in vacuo, a pale-beige solid is obtained. This is recrystallised from a heptane/toluene mixture, giving 52 g (75% of theory) as a colourless solid.

7,7-Dimethyl-7H-benzo[c]fluorene (ii-1)

(ii-b) (52 g, 198 mmol) is dissolved in 500 ml of DCM, and methanesulfonic acid (64 ml, 991 mmol) and polyphosphoric acid (77 g, 793 mmol) are added at 0° C. The reaction solution is allowed to warm to room temperature overnight. The mixture is extended with ethanol and evaporated. The residue is dissolved in toluene, washed with NaOH solution and dist. water and dried over magnesium sulfate. After removal of the solvent in vacuo, the solid is recrystallised from ethanol, giving 44 g of a yellow solid (91% of theory).

III-3) Synthesis of Building Block (ii-2)

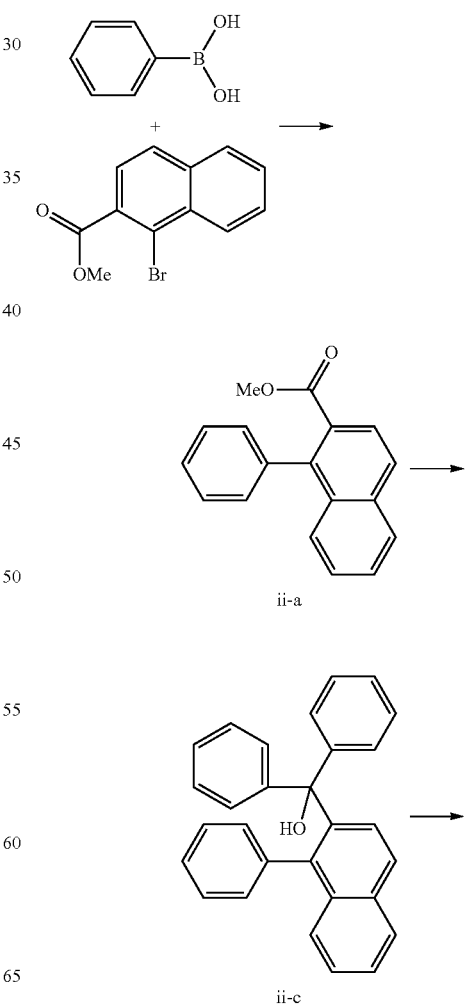

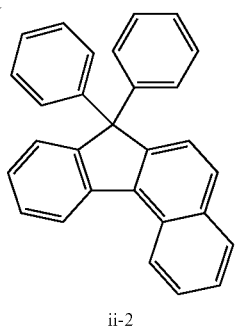

ii-2

Diphenyl(1-phenylnaphthalen-2-yl)methanol (ii-c)

(ii-a) (35 g, 133 mmol) and cerium(III) chloride (36 g, 146 mmol) are dissolved in 250 ml of THF, and phenylmagnesium chloride (3 M solution in THF) (150 ml, 450 mmol) is added at 0° C. The reaction solution is allowed to warm to room temperature in an ice bath overnight. The batch is carefully hydrolysed using saturated $NH_4Cl$ solution and neutralised using 4% hydrochloric acid. The mixture is extended with dist. water and extracted thoroughly with toluene. The combined organic phases are washed a number of times with dist. water and once with sodium hydrogencarbonate solution and dried over magnesium sulfate. After removal of the solvent in vacuo, a pale-beige solid is obtained. This is recrystallised from heptane/toluene, giving 41 g (80% of theory) as a colourless solid.

Building block (ii-2) is synthesised analogously to (ii-1), with a yield of 88%.

III-4) Synthesis of Building Block (ii-3)

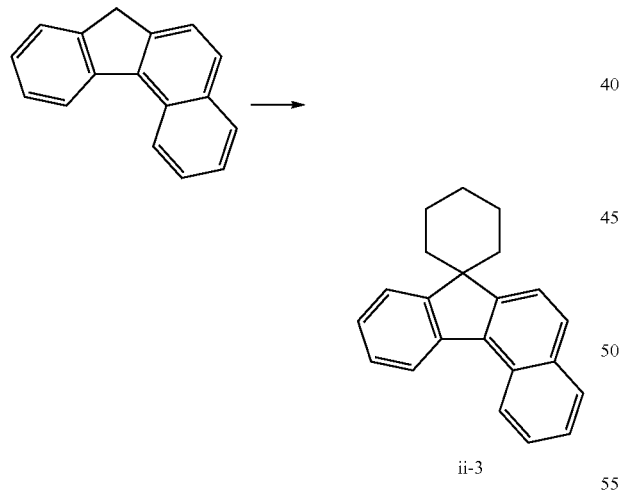

ii-3

7H-Benzo[c]fluorene is synthesised in accordance with the following literature procedure: Organic Letters, 2009, Vol. 11, No. 20, 4588-4591

Synthesis of (ii-3)

7H-Benzo[c]fluorene (38 g, 176 mmol), 1,5-dibromopentane (40.5 g, 176 mmol) and tetrabutylammonium bromide (32.3 g, 100 mmol) are dissolved in 0.5 l of toluene. 0.5 l of 3 M NaOH solution is added, and the reaction mixture is boiled under reflux overnight. The reaction mixture is cooled to room temperature, the phases are separated, the aqueous phase is extracted three times with toluene. The organic phase is washed with dist. water, dried and freed from solvent. The solid obtained is recrystallised from toluene/heptane, giving 31 g of a colourless solid (62% of theory).

III-5) Synthesis of Building Block (iii)

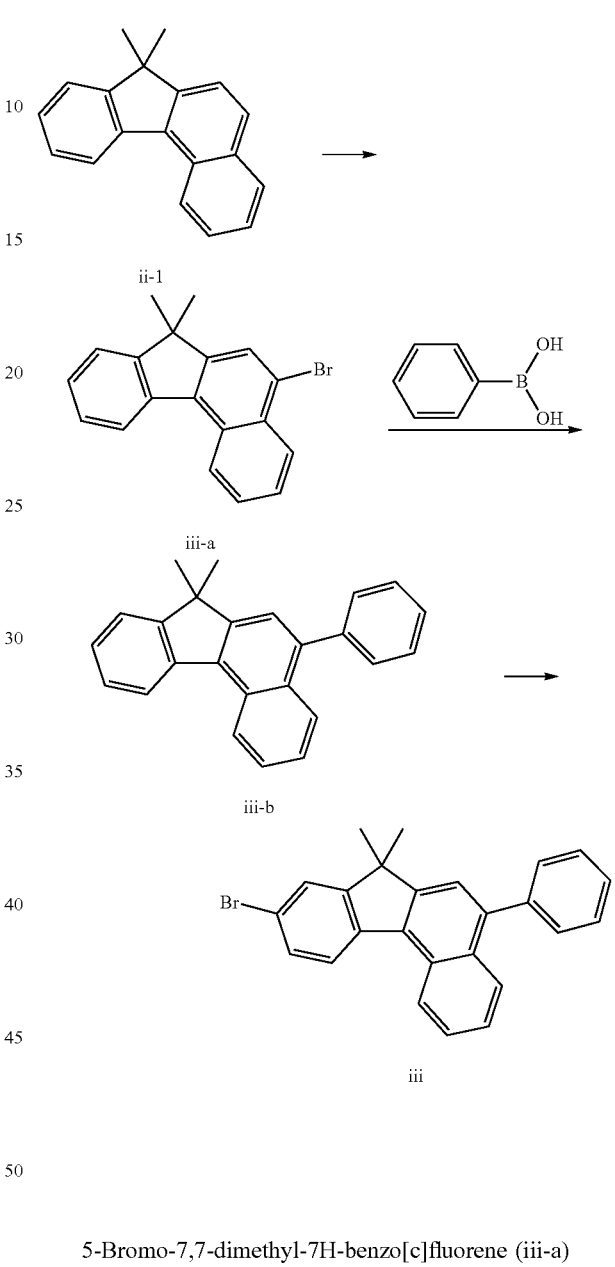

5-Bromo-7,7-dimethyl-7H-benzo[c]fluorene (iii-a)

(ii-1) (38.2 g, 156 mmol) is dissolved in 0.3 l of chloroform and cooled to 0° C. A dibromine solution (117 g, 660 mmol) in 0.2 l of chloroform is added dropwise with stirring at such a rate that the reaction temperature does not exceed 5° C. The reaction mixture is warmed to room temperature in an ice bath overnight. 200 ml of a 10% sodium thiosulfate solution are added, and the phases are separated. The aqueous phase is extracted a number of times with DCM. The organic phase is washed with dist. water, dried and freed from solvent. The solid obtained is recrystallised from toluene/heptane, giving 50 g of a colourless solid (99% of theory).

149

7,7-Dimethyl-5-phenyl-7H-benzo[c]fluorene (iii-b)

(ii-a) (28.5 g, 88 mmol), phenylboronic acid (13.2 g, 106 mmol) and potassium carbonate (30.5 g, 220 mmol) are dissolved in a mixture of 150 ml of toluene and 150 ml of water, and tetrakis(triphenylphosphine)palladium (1.02 g, 0.9 mmol) is added. The batch is heated under reflux overnight, cooled to room temperature and extended with dist. water. After phase separation, the aqueous phase is extracted a number of times with toluene. The combined organic phases are washed with dist. water, dried over magnesium sulfate and filtered through AlOx and silica gel. The organic phase is evaporated, and the resultant solid is washed with ethanol, giving 25.9 g (92% of theory) of product.

150

9-Bromo-7,7-dimethyl-5-phenyl-7H-benzo[c]fluorene (iii)

(iii-b) (25.8 g, 81 mmol) is dissolved in 0.15 l of chloroform and cooled to 0° C. A dibromine solution (13.6 g, 85 mmol) in 0.1 l of chloroform is added dropwise with stirring at such a rate that the reaction temperature does not exceed 5° C. The reaction mixture is warmed to room temperature in an ice bath overnight. 100 ml of a 10% sodium thiosulfate solution are added, and the phases are separated. The aqueous phase is extracted a number of times with DCM. The organic phase is washed with dist. water, dried and freed from solvent. The solid obtained is recrystallised from toluene/heptane, giving 22 g of a colourless solid (62% of theory).

The following compounds are prepared analogously:

| Starting material ii or analogue | Boronic acid Ar—B(OH)$_2$ | Product (iii analogue) | Yield (3 steps) |
|---|---|---|---|
| [structure] | [structure] | [structure] | 66% |
| [structure] | [structure] | [structure] | 65% |
| [structure] | [structure] | [structure] | 70% |
| [structure] | [structure] | [structure] | 61% |

-continued

| Starting material ii or analogue | Boronic acid Ar—B(OH)$_2$ | Product (iii analogue) | Yield (3 steps) |
|---|---|---|---|
| | | | 53% |
| | | | 61% |
| | | | 37% |
| | | | 64% |
| | | | 31% |

| Starting material ii or analogue | Boronic acid Ar—B(OH)$_2$ | Product (iii analogue) | Yield (3 steps) |
|---|---|---|---|
| | | | 50% |
| | | | 54% |
| | | | 34% |
| | | | 58% |
III-6) Synthesis of Building Blocks (iv)
General Reaction Scheme:
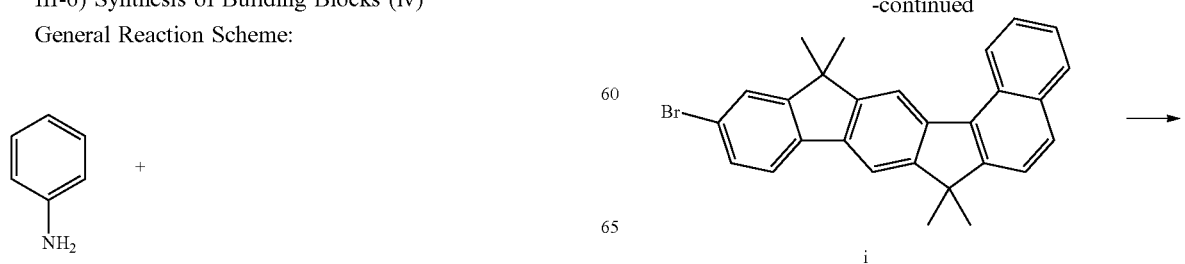

-continued

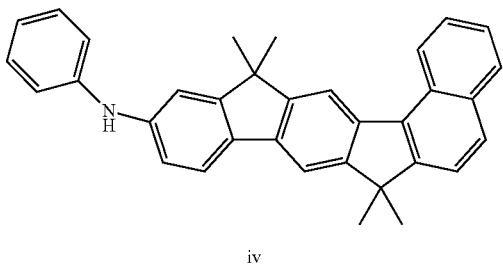

iv

N-Phenyl-7,7,13,13-tetramethyl-7,13-dihydrobenzo[g]indeno[1,2-b]-fluoren-11-amine (iv)

i (37 g, 84.2 mmol) and aniline (8.6 g, 92.6 mmol) are dissolved in 500 ml of toluene. The solution is degassed and saturated with argon. 4.1 g (5.1 mmol) of Pd(dppf)Cl$_2$ are then added. 24.3 g of sodium tert-butoxide (253 mmol) are subsequently added. The reaction mixture is heated at the boil for 12 h under a protective-gas atmosphere. Water is subsequently added to the mixture, the organic phase is washed three times with water, dried over Na$_2$SO$_4$ and evaporated in a rotary evaporator. After filtration of the crude product through silica gel with toluene, the residue which remains is recrystallised from heptane/toluene. The yield is 31 g (77% of theory).

| Starting material i or analogue | Amine | Product iv analogue | Yield |
|---|---|---|---|
|  |  |  | 58% |
|  |  |  | 72% |
|  |  |  | 62% |

-continued

| Starting material i or analogue | Amine | Product iv analogue | Yield |
|---|---|---|---|
| | | | 51% |
| | | | 63% |
| | | | 39% |
| | | | 57% |

-continued

| Starting material i or analogue | Amine | Product iv analogue | Yield |
|---|---|---|---|
| | | | 59% |
| | | | 64% |
| | | | 32% |
| | | | 61% |
| | | | 64% |

-continued

| Starting material i or analogue | Amine | Product iv analogue | Yield |
|---|---|---|---|
| | | | 68% |
| | | | 39% |
| | | | 65% |
| | | | 58% |

-continued
| Starting material i or analogue | Amine | Product iv analogue | Yield |
|---|---|---|---|
| 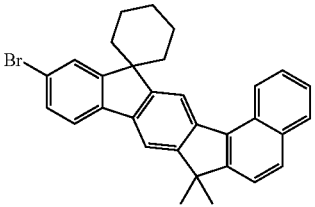 [SMILES: CC1(C)c2cc3c(cc2-c2c1ccc1ccccc21)C1(CCCCC1)c1cc(Br)ccc1-3] | 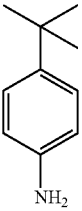 | 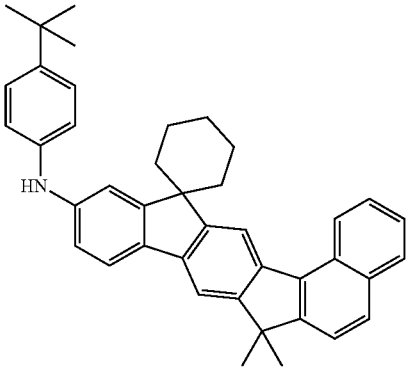 [SMILES: CC(C)(C)c1ccc(Nc2ccc3c(c2)C2(CCCCC2)c2cc4c(cc2-3)C(C)(C)c2ccc3ccccc3c2-4)cc1] | 52% |
| 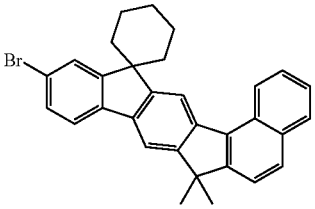 [SMILES: CC1(C)c2cc3c(cc2-c2c1ccc1ccccc21)C1(CCCCC1)c1cc(Br)ccc1-3] | 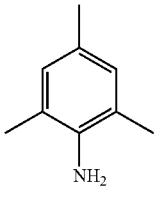 | 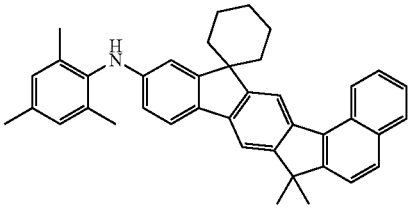 [SMILES: Cc1cc(C)c(Nc2ccc3c(c2)C2(CCCCC2)c2cc4c(cc2-3)C(C)(C)c2ccc3ccccc3c2-4)c(C)c1] | 66% |
| 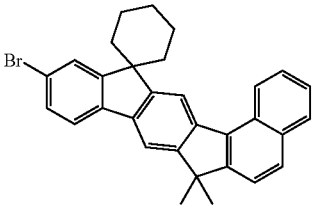 | 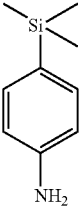 | 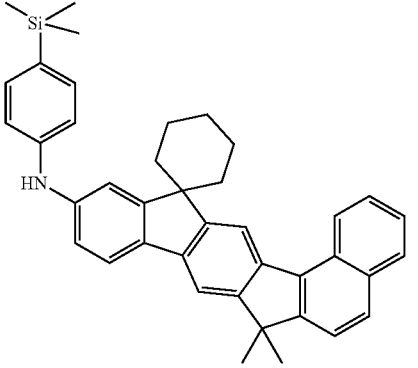 [SMILES: CC1(C)c2cc3c(cc2-c2c1ccc1ccccc21)C1(CCCCC1)c1cc(Nc2ccc([Si](C)(C)C)cc2)ccc1-3] | 46% |
| 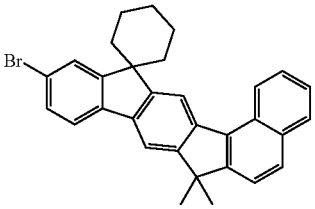 [SMILES: CC1(C)c2cc3c(cc2-c2c1ccc1ccccc21)C1(CCCCC1)c1cc(Br)ccc1-3] | 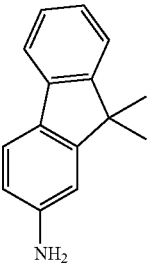 [SMILES: CC1(C)c2ccccc2-c2ccc(N)cc21] | 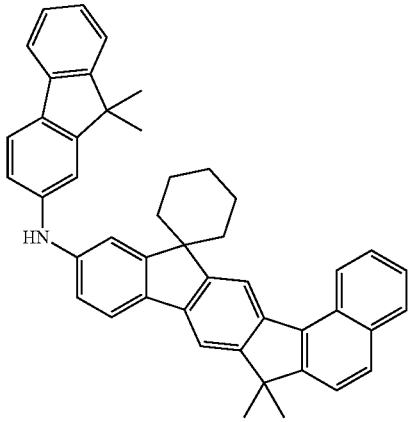 [SMILES: CC1(C)c2ccccc2-c2ccc(Nc3ccc4c(c3)C3(CCCCC3)c3cc5c(cc3-4)C(C)(C)c3ccc4ccccc4c3-5)cc21] | 72% |

-continued

| Starting material i or analogue | Amine | Product iv analogue | Yield |
|---|---|---|---|
| | | | 64% |
| | | | 33% |
| | | | 54% |
| | | | 47% |
| | | | 41% |

III-7) Synthesis of Target Compounds (III)
General Reaction Scheme:

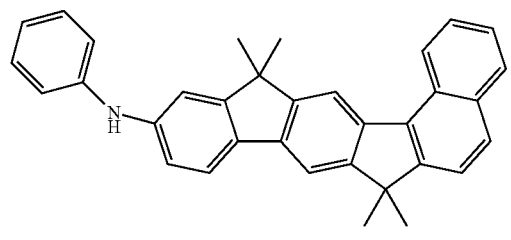
iv

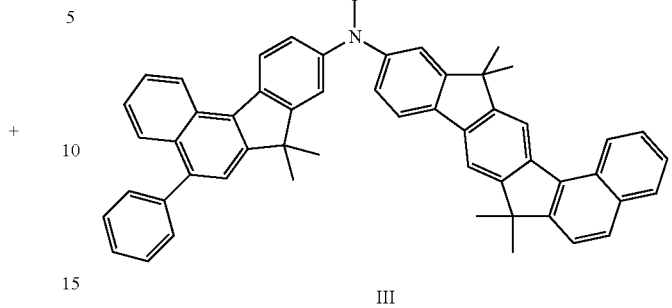
III 7,7,13,13-Tetramethyl-N-(7,7-dimethyl-5-phenyl-7H-benzo[c]fluoren-9-yl)-N-phenyl-7,13-dihydrobenzo[g]indeno[1,2-b]fluoren-11-amine (III)

Synthesis Example 37 iv (20 g, 44.3 mmol) and iii (18.6 g, 46.5 mmol) are dissolved in 500 ml of toluene. The solution is degassed and saturated with argon. 2.5 ml (2.5 mmol) of a 1 M tri-tert-butylphosphine solution and 0.355 g (1.23 mmol) of palladium(II) acetate are then added. 11.9 g of sodium tert-butoxide (124 mmol) are subsequently added. The reaction mixture is heated at the boil for 12 h under a protective-gas atmosphere. Water is subsequently added to the mixture, the organic phase is washed three times with water, dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9%. The yield is 21 g (62% of theory).

The following compounds are prepared analogously:

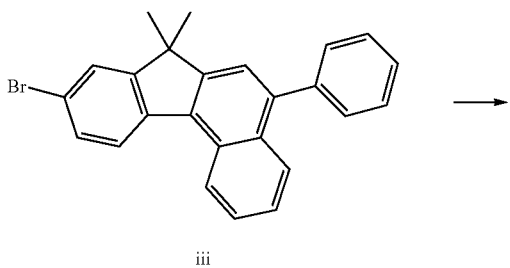
iii

| Ex. | Starting material iv or analogue | Starting material iii or analogue |
|---|---|---|
| 38 | | |

| | | |
|---|---|---|
| 39 | 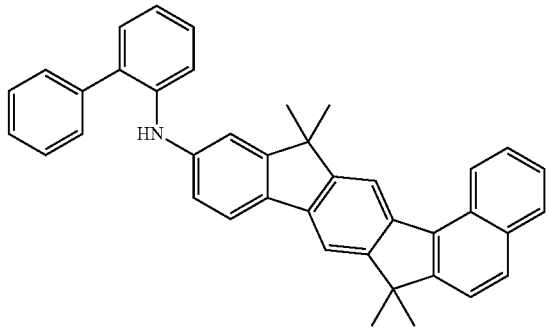 [SMILES: CC1(C)c2cc(Nc3ccccc3-c3ccccc3)ccc2-c2cc3c(cc21)-c1c(ccc2ccccc12)C3(C)C] | 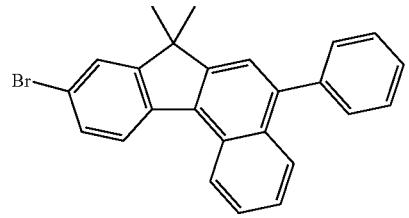 [SMILES: CC1(C)c2cc(Br)ccc2-c2c1cc(-c1ccccc1)c1ccccc21] |
| 40 | 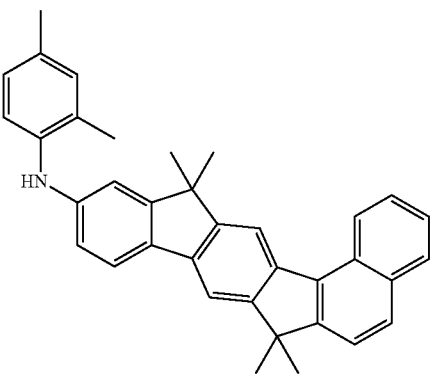 [SMILES: Cc1ccc(Nc2ccc3c(c2)C(C)(C)c2cc4c(cc2-3)C(C)(C)c2ccc3ccccc3c2-4)c(C)c1] | 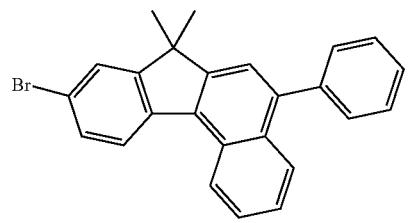 [SMILES: CC1(C)c2cc(Br)ccc2-c2c1cc(-c1ccccc1)c1ccccc21] |
| 41 | 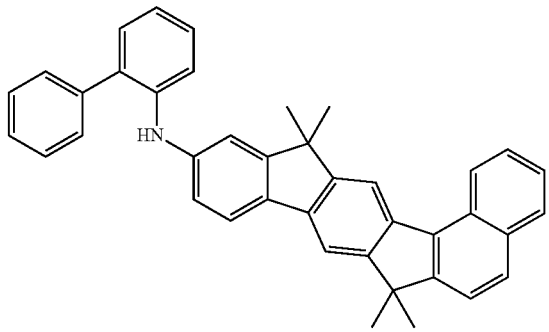 [SMILES: CC1(C)c2cc(Nc3ccccc3-c3ccccc3)ccc2-c2cc3c(cc21)-c1c(ccc2ccccc12)C3(C)C] | 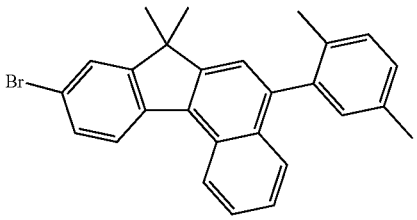 [SMILES: Cc1ccc(C)c(-c2cc3c(c4ccccc24)-c2ccc(Br)cc2C3(C)C)c1] |
| 42 | 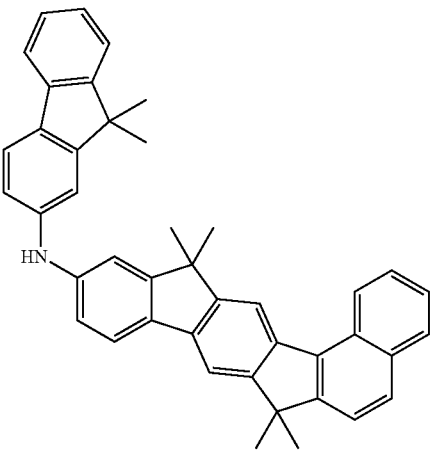 [SMILES: CC1(C)c2ccccc2-c2ccc(Nc3ccc4c(c3)C(C)(C)c3cc5c(cc3-4)C(C)(C)c3ccc4ccccc4c3-5)cc21] | 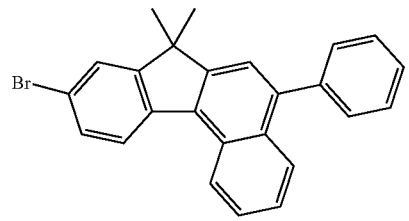 [SMILES: CC1(C)c2cc(Br)ccc2-c2c1cc(-c1ccccc1)c1ccccc21] |

-continued
| | 171 | 172 |
|---|---|---|
| 43 | 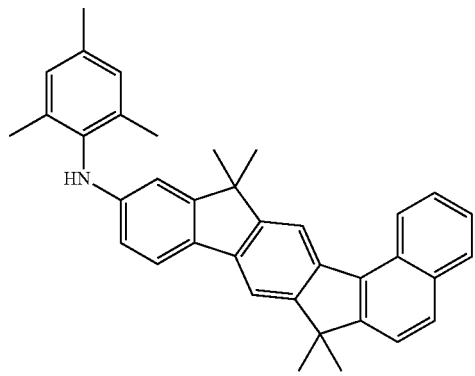 [SMILES: Cc1cc(C)c(Nc2ccc3c(c2)C(C)(C)c2cc4c(cc2-3)C(C)(C)c2ccc3ccccc3c2-4)c(C)c1] | 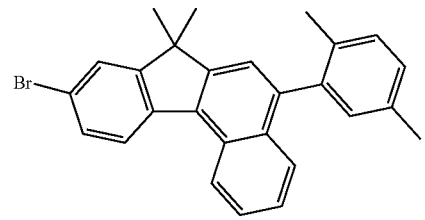 [SMILES: Cc1ccc(C)c(-c2cc3c(c4ccccc24)-c2ccc(Br)cc2C3(C)C)c1] |
| 44 | 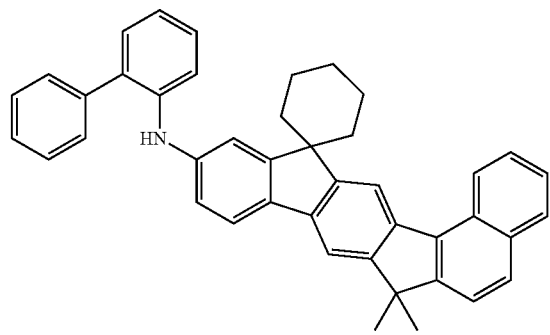 [SMILES: CC1(C)c2cc3c(cc2-c2c1ccc1ccccc21)C1(CCCCC1)c1cc(Nc2ccccc2-c2ccccc2)ccc1-3] | 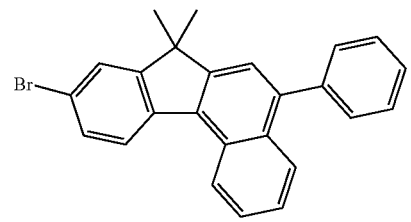 [SMILES: CC1(C)c2cc(Br)ccc2-c2c1cc(-c1ccccc1)c1ccccc21] |
| 45 | 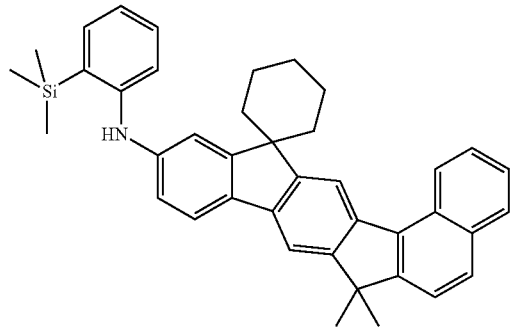 [SMILES: CC1(C)c2cc3c(cc2-c2c1ccc1ccccc21)C1(CCCCC1)c1cc(Nc2ccccc2[Si](C)(C)C)ccc1-3] | 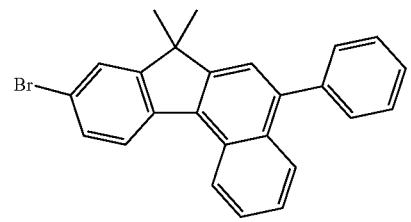 [SMILES: CC1(C)c2cc(Br)ccc2-c2c1cc(-c1ccccc1)c1ccccc21] |
| 46 | 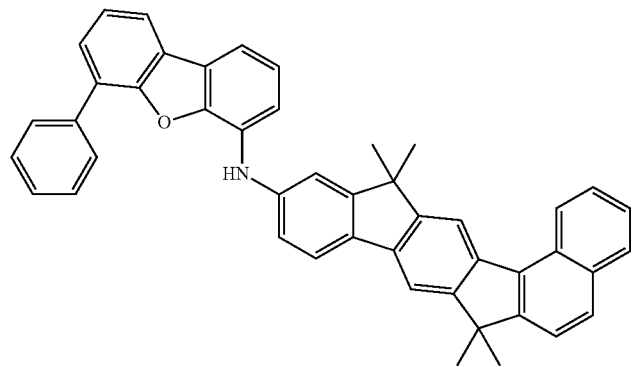 [SMILES: CC1(C)c2cc(Nc3cccc4c3oc3c(-c5ccccc5)cccc34)ccc2-c2cc3c(cc21)-c1c(ccc2ccccc12)C3(C)C] | 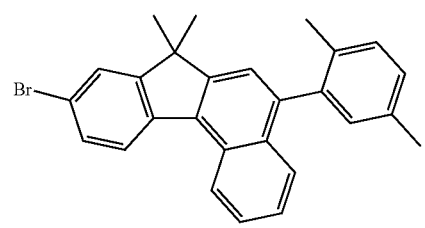 [SMILES: Cc1ccc(C)c(-c2cc3c(c4ccccc24)-c2ccc(Br)cc2C3(C)C)c1] |

| 47 | 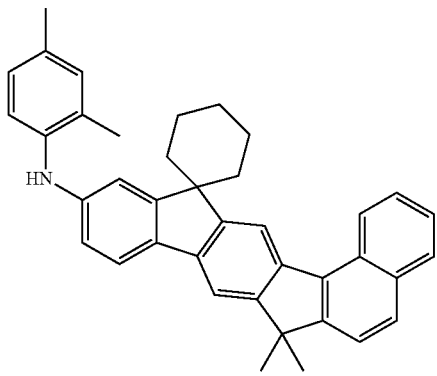 [SMILES: Cc1ccc(Nc2ccc3c(c2)C2(CCCCC2)c2cc4c(cc2-3)C(C)(C)c2ccc3ccccc3c2-4)c(C)c1] | 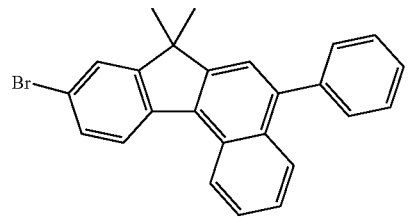 [SMILES: CC1(C)c2cc(Br)ccc2-c2c1cc(-c1ccccc1)c1ccccc21] |
| 48 | 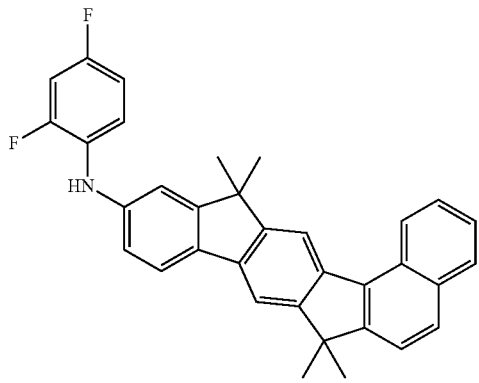 [SMILES: CC1(C)c2cc(Nc3ccc(F)cc3F)ccc2-c2cc3c(cc21)-c1c(ccc2ccccc12)C3(C)C] | 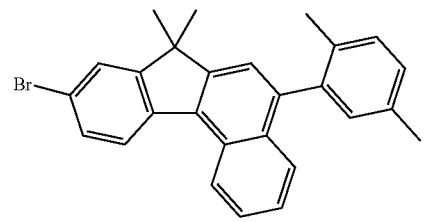 [SMILES: Cc1ccc(C)c(-c2cc3c(c4ccccc24)-c2ccc(Br)cc2C3(C)C)c1] |
| 49 | 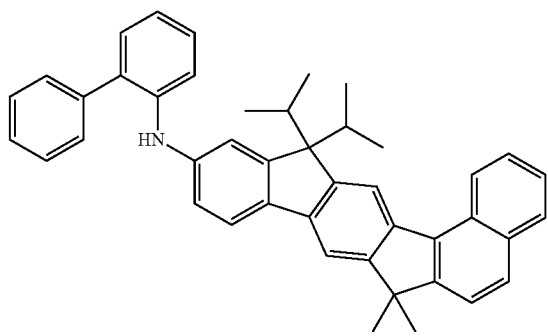 [SMILES: CC(C)C1(C(C)C)c2cc(Nc3ccccc3-c3ccccc3)ccc2-c2cc3c(cc21)-c1c(ccc2ccccc12)C3(C)C] | 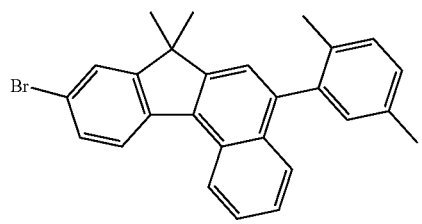 [SMILES: Cc1ccc(C)c(-c2cc3c(c4ccccc24)-c2ccc(Br)cc2C3(C)C)c1] |
| 50 | 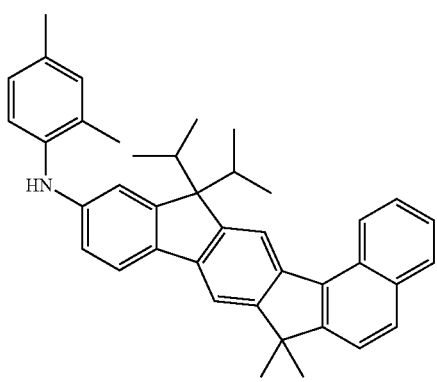 [SMILES: Cc1ccc(Nc2ccc3c(c2)C(C(C)C)(C(C)C)c2cc4c(cc2-3)C(C)(C)c2ccc3ccccc3c2-4)c(C)c1] | 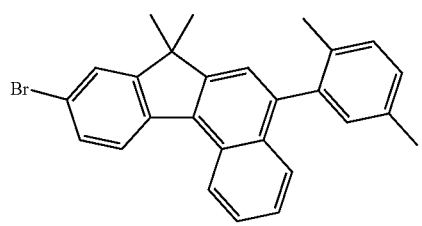 [SMILES: Cc1ccc(C)c(-c2cc3c(c4ccccc24)-c2ccc(Br)cc2C3(C)C)c1] |

-continued

| Ex. | Product III analogue | Yield |
|---|---|---|
| 38 | | 74% |
| 39 | | 81% |
| 40 | | 69% |

| 41 | 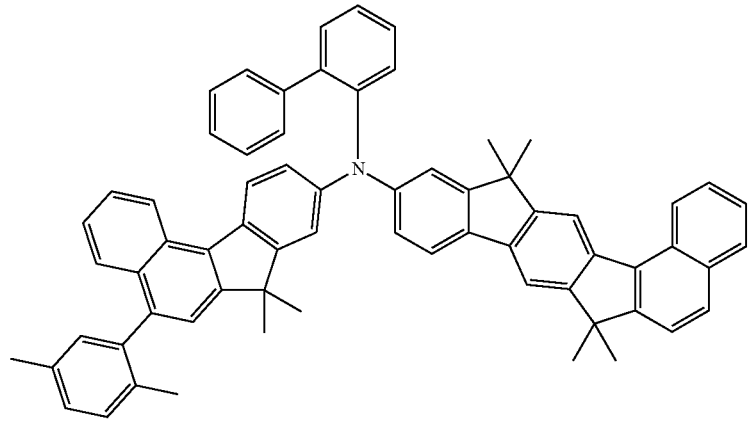 [SMILES: Cc1ccc(C)c(-c2cc3c(c4ccccc24)-c2ccc(N(c4ccc5c(c4)C(C)(C)c4cc6c(cc4-5)C(C)(C)c4ccc5ccccc5c4-6)c4ccccc4-c4ccccc4)cc2C3(C)C)c1] | 75% |
| 42 | 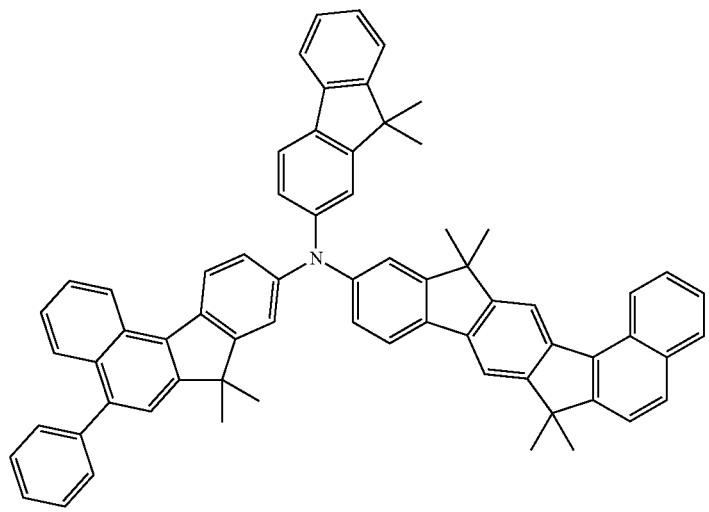 [SMILES: CC1(C)c2ccccc2-c2ccc(N(c3ccc4c(c3)C(C)(C)c3cc5c(cc3-4)C(C)(C)c3ccc4ccccc4c3-5)c3ccc4c(c3)C(C)(C)c3cc(-c5ccccc5)c5ccccc5c3-4)cc21] | 52% |
| 43 | 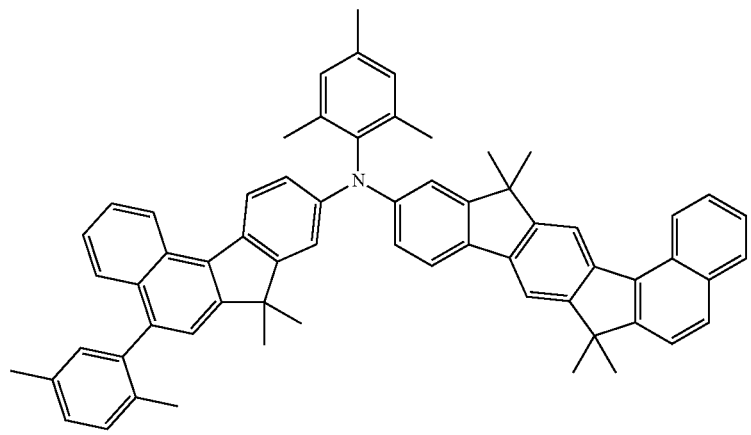 [SMILES: Cc1cc(C)c(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1] | 58% |

| 44 | 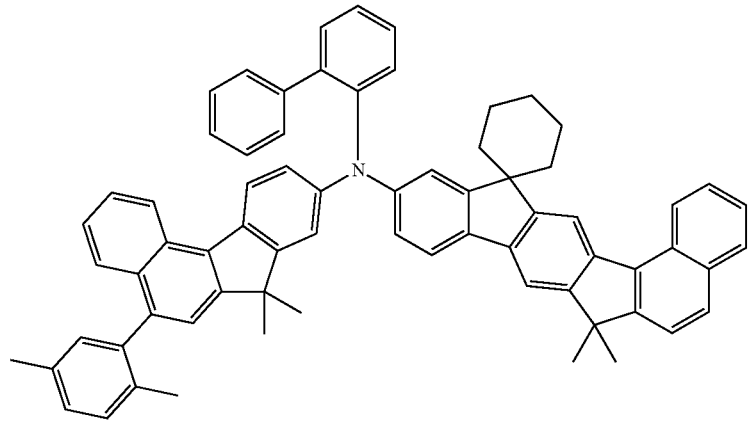 [SMILES: Cc1ccc(C)c(-c2cc3c(c4ccccc24)-c2ccc(N(c4ccc5c(c4)C4(CCCCC4)c4cc6c(cc4-5)C(C)(C)c4ccc5ccccc5c4-6)c4ccccc4-c4ccccc4)cc2C3(C)C)c1] | 33% |
| 45 | 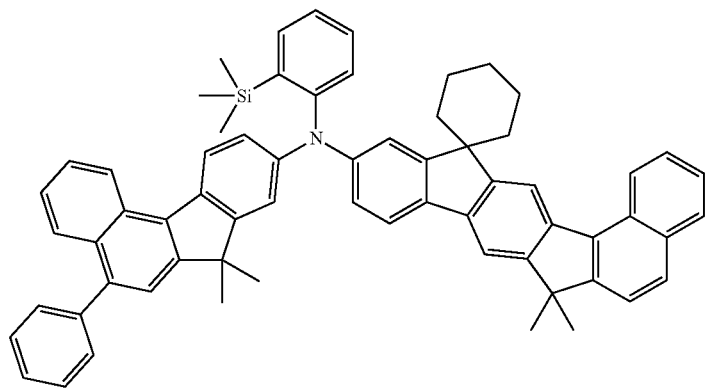 [SMILES: CC1(C)c2cc3c(cc2-c2c1ccc1ccccc21)C1(CCCCC1)c1cc(N(c2ccc4c(c2)C(C)(C)c2cc(-c5ccccc5)c5ccccc5c2-4)c2ccccc2[Si](C)(C)C)ccc1-3] | 79% |
| 46 | 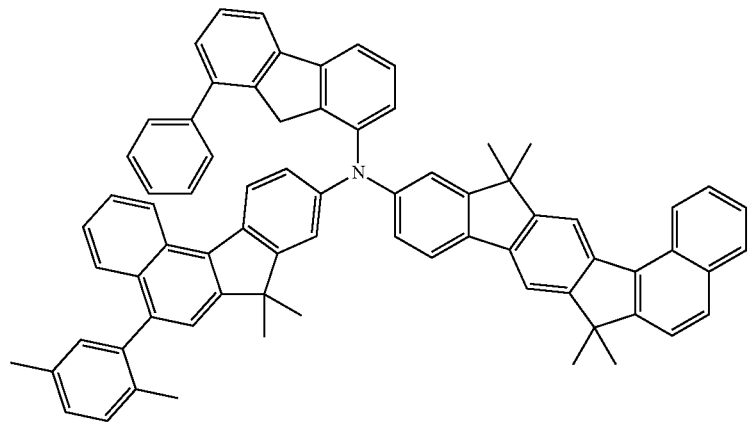 [SMILES: Cc1ccc(C)c(-c2cc3c(c4ccccc24)-c2ccc(N(c4ccc5c(c4)C(C)(C)c4cc6c(cc4-5)C(C)(C)c4ccc5ccccc5c4-6)c4cccc5c4Cc4c(-c6ccccc6)cccc4-5)cc2C3(C)C)c1] | 54% |

47 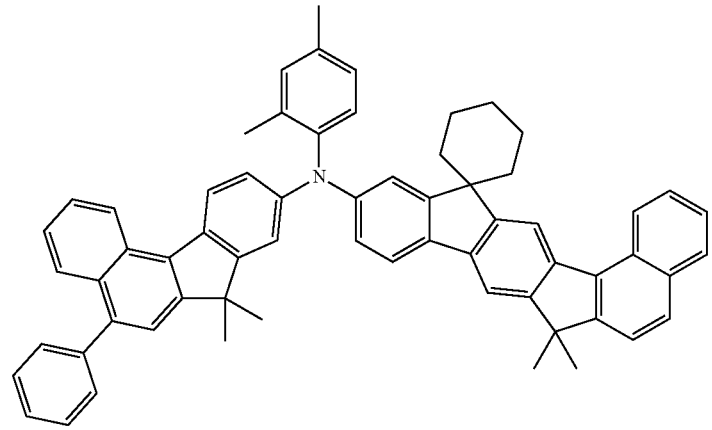 [SMILES: Cc1ccc(N(c2ccc3c(c2)C(C)(C)c2cc(-c4ccccc4)c4ccccc4c2-3)c2ccc3c(c2)C2(CCCCC2)c2cc4c(cc2-3)C(C)(C)c2ccc3ccccc3c2-4)c(C)c1] 81%
48 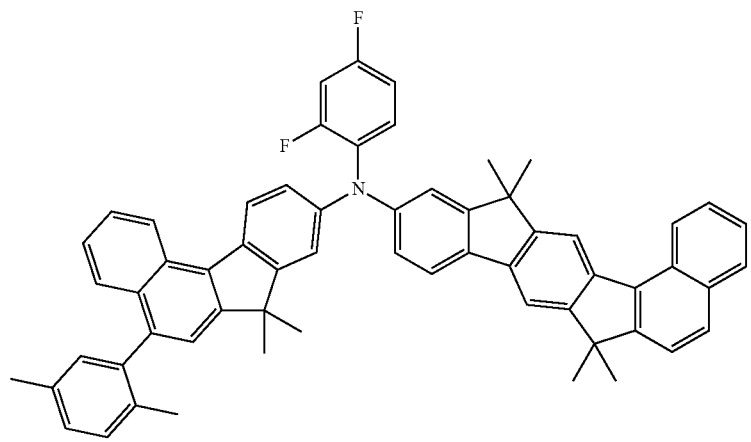 [SMILES: Cc1ccc(C)c(-c2cc3c(c4ccccc24)-c2ccc(N(c4ccc5c(c4)C(C)(C)c4cc6c(cc4-5)C(C)(C)c4ccc5ccccc5c4-6)c4ccc(F)cc4F)cc2C3(C)C)c1] 44%
49 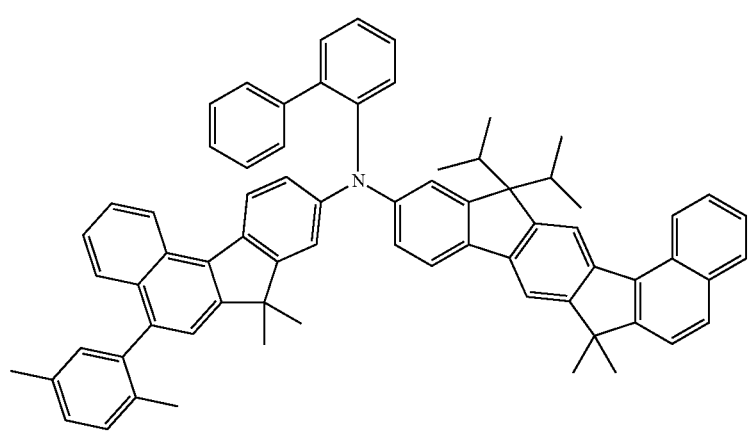 [SMILES: Cc1ccc(C)c(-c2cc3c(c4ccccc24)-c2ccc(N(c4ccc5c(c4)C(C(C)C)(C(C)C)c4cc6c(cc4-5)C(C)(C)c4ccc5ccccc5c4-6)c4ccccc4-c4ccccc4)cc2C3(C)C)c1] 63%

-continued

50
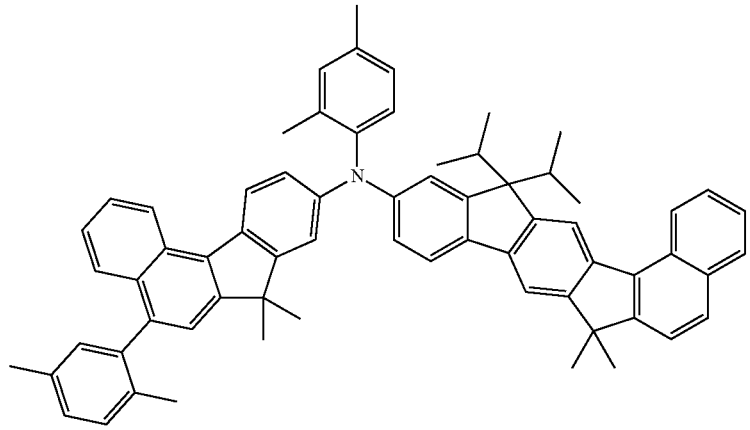 [SMILES: Cc1ccc(N(c2ccc3c(c2)C(C)(C)c2cc(-c4cc(C)ccc4C)c4ccccc4c2-3)c2ccc3c(c2)C(C(C)C)(C(C)C)c2cc4c(cc2-3)C(C)(C)c2ccc3ccccc3c2-4)c(C)c1]
71%

B) Device Examples: Production of OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in the following examples (see Tables 1 to 3). The substrates used are glass plates coated with structured ITO (indium tin oxide) in a thickness of 50 nm. The OLEDs have in principle the following layer structure: substrate/buffer (20 nm)/hole-injection layer (HIL, 5 nm)/hole-transport layer (HTL, 30 nm)/emission layer (EML, 20 nm)/electron-transport layer (ETL, 30 nm)/electron-injection layer (LiQ 1 nm) and finally a cathode. The cathode is formed by an aluminium layer with a thickness of 100 nm. A layer of Clevios P VP AI 4083 (purchased from Heraeus Clevios GmbH, Leverkusen) with a thickness of 20 nm is applied as buffer by spin coating. All remaining materials are applied by thermal vapour deposition in a vacuum chamber. The structure of EML and ETL of the OLEDs is shown in Table 1. The materials used are shown in Table 3.

The emission layer (EML) always consists of at least one matrix material (host=H) and an emitting dopant (dopant=D), which is admixed with the matrix material in a certain proportion by volume by co-evaporation. An expression such as H1:D1 (95%:5%) here means that material H1 is present in the layer in a proportion by volume of 95% and D1 is present in the layer in a proportion of 5%. Analogously, the electron-transport layer may also consist of a mixture of two materials.

The OLEDs are characterised by standard methods. For this purpose, the electroluminescence spectra are recorded, the current efficiency (measured in cd/A) and the external quantum efficiency (EQE, measured in percent) as a function of the luminous density are calculated from current/voltage/luminous density characteristic lines (IUL characteristic lines) assuming Lambert emission characteristics, and finally the lifetime of the components is determined. The electroluminescence spectra are recorded at a luminous density of 1000 cd/m$^2$, and the CIE 1931 x and y colour coordinates are calculated therefrom. The expression EQE @ 1000 cd/m$^2$ denotes the external quantum efficiency at an operating luminous density of 1000 cd/m$^2$. The lifetime LT50 @ 60 mA/cm$^2$ is the time which passes until the initial luminance (cd/m$^2$) at a current density of 60 mA/cm$^2$ has dropped to half. The data obtained for the various OLEDs are summarised in Table 2.

Use of Compounds According to the Invention as Dopants in Fluorescent OLEDs

Compounds according to the invention are particularly suitable as blue fluorescent dopants. The comparative dopants used are dopants V-D1 and V-D2 known from the prior art (WO 2006/108497 and WO 2008/006449). Dopants D3, D4, D5, D6 and D7 are measured as examples according to the invention.

TABLE 1

Structure of the OLEDs

| Ex. | EML Thickness/nm | ETL Thickness /nm |
|---|---|---|
| V1 | H1(95%):V-D1(5%) 20 nm | ETM1(50%):LiQ(50%) 30 nm |
| V2 | H3(95%):V-D1(5%) 20 nm | ETM1(50%):LiQ(50%) 30 nm |
| V3 | H1(95%):V-D2(5%) 20 nm | ETM1(50%):LiQ(50%) 30 nm |
| V4 | H3(95%):V-D2(5%) 20 nm | ETM1(50%):LiQ(50%) 30 nm |
| E5 | H1(95%):D3(5%) 20 nm | ETM1(50%):LiQ(50%) 30 nm |
| E6 | H2(95%)D3(5%) 20 nm | ETM1(50%):LiQ(50%) 30 nm |
| E7 | H1(95%):D4(5%) 20 nm | ETM1(50%):LiQ(50%) 30 nm |
| E8 | H3(95%):D4(5%) 20 nm | ETM1(50%):LiQ(50%) 30 nm |
| E9 | H1(95%):D5(5%) 20 nm | ETM1(50%):LiQ(50%) 30 nm |
| E10 | H2(95%)D5(5%) 20 nm | ETM1(50%):LiQ(50%) 30 nm |
| E11 | H1(95%):D6(5%) 20 nm | ETM1(50%):LiQ(50%) 30 nm |
| E12 | H3(95%):VD6(5%) 20 nm | ETM1(50%):LiQ(50%) 30 nm |
| E13 | H1(95%):D7(5%) 20 nm | ETM1(50%):LiQ(50%) 30 nm |

TABLE 2

Data for the OLEDs

| Ex. | EQE @ 1000 cd/m$^2$ % | LT50 @ 60 mA/cm$^2$ [h] | CIE x | CIE y |
|---|---|---|---|---|
| V1 | 2.4 | 110 | 0.16 | 0.09 |
| V2 | 2.3 | 120 | 0.16 | 0.10 |
| V3 | 2.6 | 260 | 0.15 | 0.17 |
| V4 | 2.5 | 280 | 0.15 | 0.18 |
| E5 | 6.2 | 560 | 0.14 | 0.10 |
| E6 | 6.4 | 620 | 0.14 | 0.11 |
| E7 | 6.9 | 580 | 0.14 | 0.12 |
| E8 | 7.1 | 600 | 0.14 | 0.13 |

TABLE 2-continued
Data for the OLEDs
| Ex. | EQE @ 1000 cd/m² % | LT50 @ 60 mA/cm² [h] | CIE x | y |
|---|---|---|---|---|
| E9  | 6.5 | 560 | 0.13 | 0.10 |
| E10 | 6.8 | 610 | 0.13 | 0.11 |
| E11 | 5.2 | 450 | 0.13 | 0.08 |
| E12 | 5.6 | 510 | 0.14 | 0.09 |
| E13 | 6.7 | 420 | 0.14 | 0.08 |
TABLE 3
Structures of the materials used
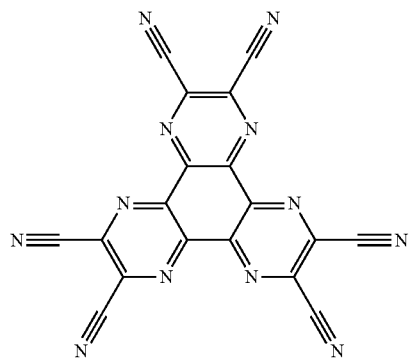 [SMILES: N#Cc1nc2c3nc(C#N)c(C#N)nc3c3nc(C#N)c(C#N)nc3c2nc1C#N]
HIL1
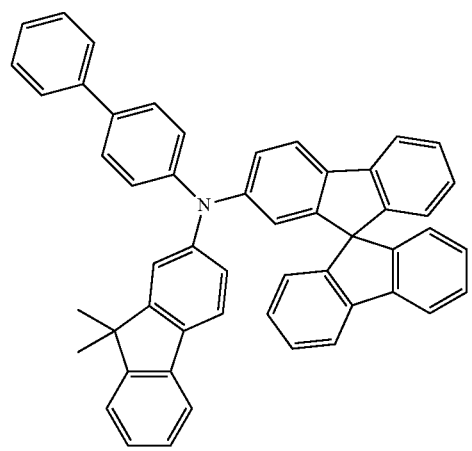 [SMILES: CC1(C)c2ccccc2-c2ccc(N(c3ccc(-c4ccccc4)cc3)c3ccc4c(c3)C3(c5ccccc5-c5ccccc53)c3ccccc3-4)cc21]
HTL
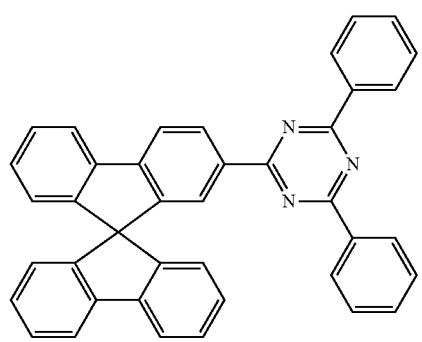 [SMILES: c1ccc(-c2nc(-c3ccccc3)nc(-c3ccc4c(c3)C3(c5ccccc5-c5ccccc53)c3ccccc3-4)n2)cc1]
ETM1

TABLE 3-continued
Structures of the materials used
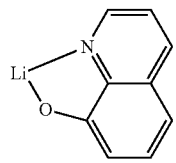
LiQ
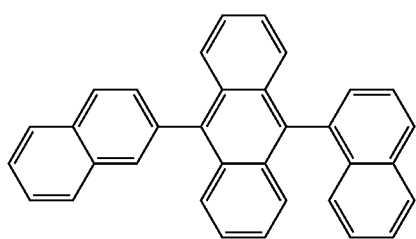 [SMILES: c1ccc2cc(-c3c4ccccc4c(-c4cccc5ccccc45)c4ccccc34)ccc2c1]
H1
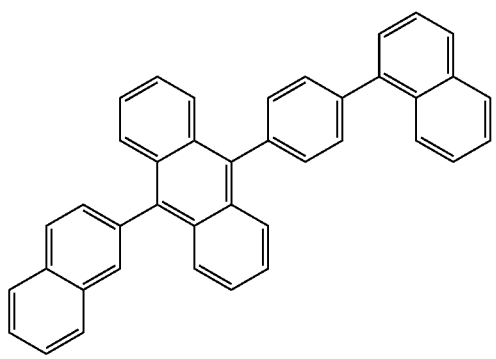 [SMILES: c1ccc2cc(-c3c4ccccc4c(-c4ccc(-c5cccc6ccccc56)cc4)c4ccccc34)ccc2c1]
H2
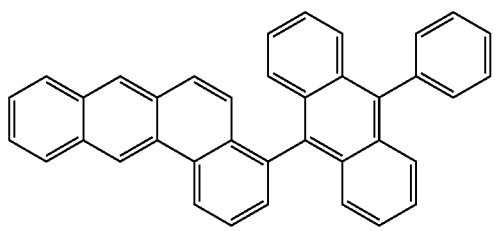 [SMILES: c1ccc(-c2c3ccccc3c(-c3cccc4c3ccc3cc5ccccc5cc34)c3ccccc23)cc1]
H3
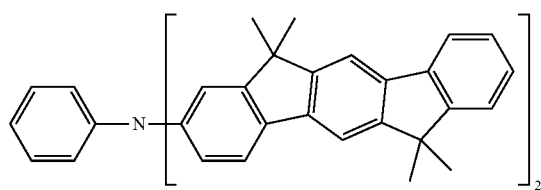
V-D1

TABLE 3-continued
Structures of the materials used
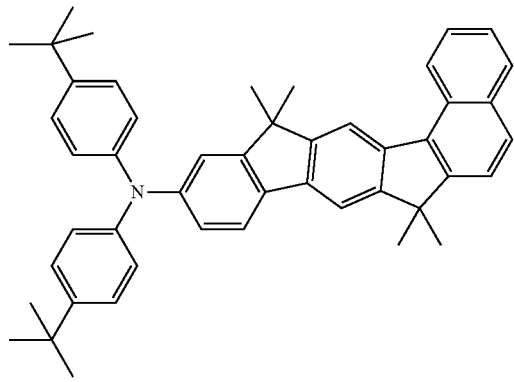 [SMILES: CC(C)(C)c1ccc(N(c2ccc(C(C)(C)C)cc2)c2ccc3c(c2)C(C)(C)c2cc4c(cc2-3)C(C)(C)c2ccc3ccccc3c2-4)cc1]
V-D2
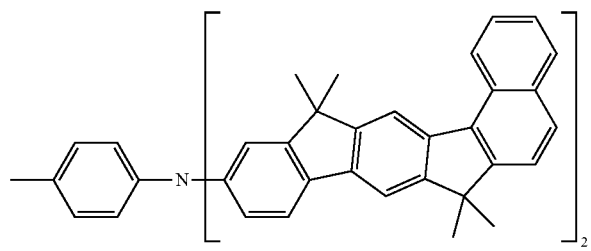
D3
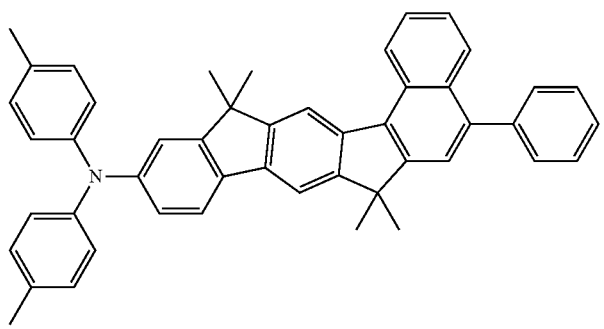 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
D4
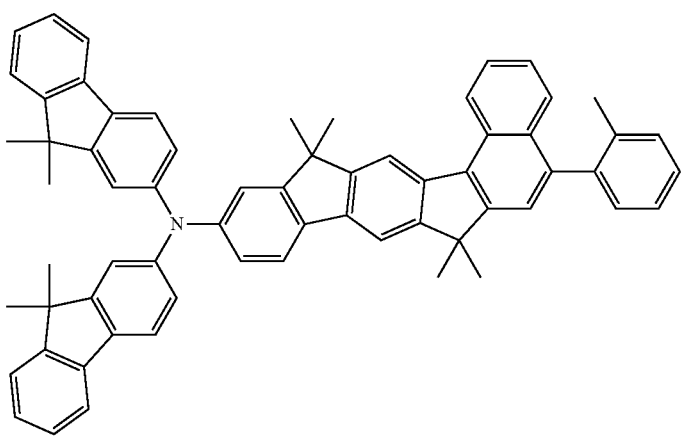 [SMILES: Cc1ccccc1-c1cc2c(c3ccccc13)-c1cc3c(cc1C2(C)C)-c1ccc(N(c2ccc4c(c2)C(C)(C)c2ccccc2-4)c2ccc4c(c2)C(C)(C)c2ccccc2-4)cc1C3(C)C]
D5

TABLE 3-continued

Structures of the materials used

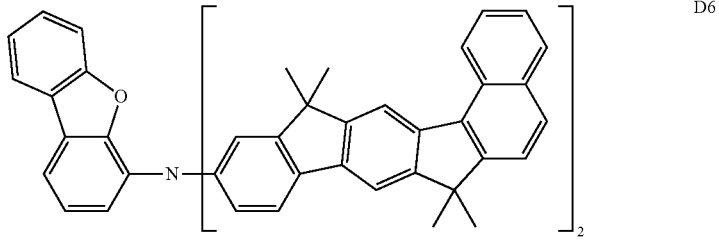
D6

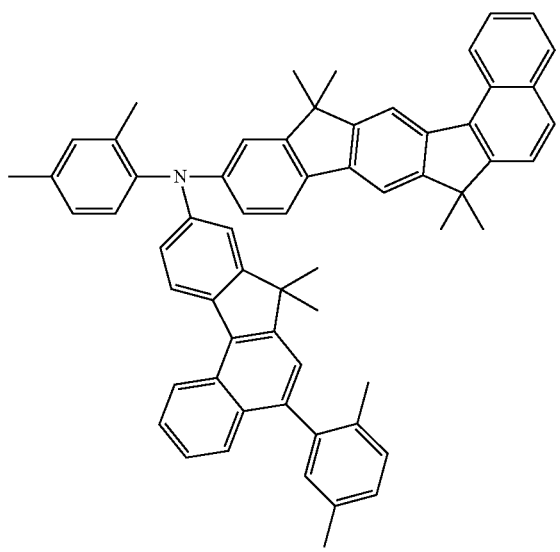 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1]
D7

The results show that efficient OLEDs (external quantum efficiency) having a long lifetime (LT50) can be obtained with the compounds according to the invention, with deep-blue emission.

By comparison, dopants V-D1 and V-D2 known from the prior art exhibit significantly worse values for the efficiency and the lifetime.

The invention claimed is:

1. A compound of formula (I-1) or (III-1):

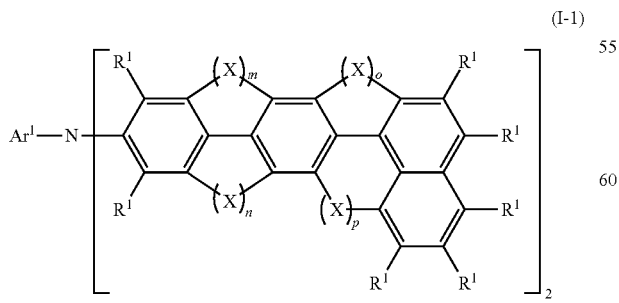
(I-1)

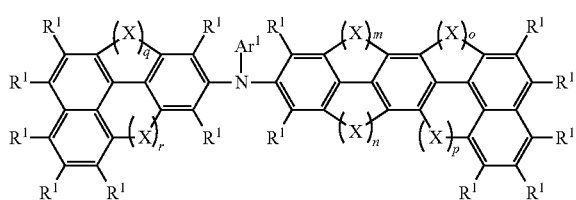
(III-1)

wherein $Ar^1$ is on each occurrence, identically or differently, selected from the group consisting of phenyl, naphthyl, anthracenyl, phenanthrenyl, pyrenyl, triphenylenyl, chrysenyl, biphenyl, terphenyl, fluorenyl, spirobifluorenyl, carbazolyl, dibenzofuranyl, dibenzothiophenyl or silafluorenyl, each of which is optionally substituted by one or more radicals $R^1$;

$R^1$ is on each occurrence, identically or differently, H, D, F, Cl, Br, I, C(=O)$R^2$, CN, Si($R^2$)$_3$, N($R^2$)$_2$, NO$_2$, P(=O)($R^2$)$_2$, S(=O)$R^2$, S(=O)$_2R^2$, a straight-chain alkyl, alkoxy, or thioalkyl group having 1 to 20 C atoms or a branched or cyclic alkyl, alkoxy, or thioalkyl group having 3 to 20 C atoms or an alkenyl or alkynyl group having 2 to 20 C atoms, each of which is optionally substituted by one or more radicals $R^2$ and wherein one or more $CH_2$ groups is optionally replaced by —$R^2C$=$CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO, or $SO_2$ and wherein one or more H atoms is optionally replaced by D, F, Cl, Br, I, CN, or $NO_2$, an aromatic or heteroaromatic ring system having 5 to 30 aromatic ring atoms optionally substituted by one or more radicals $R^2$, or an aryloxy or heteroaryloxy group having 5 to 30 aromatic ring atoms optionally substituted by one or more radicals $R^2$, and wherein two or more radicals $R^1$ optionally define a ring with one another;

$R^2$ is on each occurrence, identically or differently, H, D, F, Cl, Br, I, C(=O)$R^3$, CN, $Si(R^3)_3$, $N(R^3)_2$, $NO_2$, P(=O)($R^3$)$_2$, S(=O)$R^3$, S(=O)$_2R^3$, a straight-chain alkyl, alkoxy, or thioalkyl group having 1 to 20 C atoms or a branched or cyclic alkyl, alkoxy, or thioalkyl group having 3 to 20 C atoms or an alkenyl or alkynyl group having 2 to 20 C atoms, each of which is optionally substituted by one or more radicals $R^3$ and wherein one or more $CH_2$ groups is optionally replaced by —$R^3C$=$CR^3$—, —C≡C—, $Si(R^3)_2$, C=O, C=S, C=$NR^3$, —C(=O)O—, —C(=O)$NR^3$—, $NR^3$, P(=O)($R^3$), —O—, —S—, SO, or $SO_2$ and wherein one or more H atoms in the above-mentioned groups is optionally replaced by D, F, Cl, Br, I, CN, or $NO_2$, an aromatic or heteroaromatic ring system having 5 to 30 aromatic ring atoms optionally substituted by one or more radicals $R^3$, or an aryloxy or heteroaryloxy group having 5 to 30 aromatic ring atoms optionally substituted by one or more radicals $R^3$, and wherein two or more radicals $R^2$ optionally define a ring system with one another;

$R^3$ is on each occurrence, identically or differently, H, D, F, or an aliphatic, aromatic, or heteroaromatic organic radical having 1 to 20 C atoms, wherein one or more H atoms is optionally replaced by D or F; and wherein two or more radicals $R^3$ optionally define a ring system with one another;

X is $C(R^1)_2$; and m, n, o, p, q, and r are on each occurrence, identically or differently, 0 or 1; wherein when any one of m, n, o, p, q and r is 0, a group $R^1$ is bonded instead at the relevant positions to which the corresponding group X is bonded; and wherein the sum of m and n is 1, and the sum of o and p is 1, and the sum of q and r is 1.

2. The compound of claim 1, wherein $R^1$ is on each occurrence, identically or differently, H, D, F, CN, $Si(R^2)_3$, a straight-chain alkyl group having 1 to 8 C atoms, or a branched or cyclic alkyl group having 3 to 8 C atoms, wherein the alkyl groups are optionally substituted by one or more radicals $R^2$ and wherein one or more $CH_2$ groups is optionally replaced by —C≡C—, —$R^2C$=$CR^2$—, $Si(R^2)_2$, C=O, or —O—, or an aryl or heteroaryl group having 6 to 16 aromatic ring atoms optionally substituted by one or more radicals $R^2$.

3. An oligomer, polymer, or dendrimer comprising one or more compounds of claim 1, wherein the bond(s) to the polymer, oligomer or dendrimer are located at any desired positions in formulae (I-1) or (III-1) which are substituted by $R^1$ or $R^2$.

4. A formulation comprising at least one polymer, oligomer, or dendrimer of claim 3 and at least one solvent.

5. An electronic device selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices, wherein said electronic device comprises at least one polymer, oligomer or dendrimer of claim 3.

6. The electronic device of claim 5, wherein said electronic device is an organic electroluminescent device and said at least one polymer, oligomer or dendrimer is employed as emitting material in an emitting layer.

7. A formulation comprising at least one compound of claim 1 and at least one solvent.

8. An electronic device selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes, and organic electroluminescent devices, wherein said electronic device comprises at least one compound of claim 1.

9. The electronic device of claim 8, wherein said electronic device is an organic electroluminescent devices and said at least one compound is employed as emitting material in an emitting layer.

10. A process for preparing the compound of claim 1, wherein one or more organometallic coupling processes is employed.

* * * * *